US008148154B2

(12) United States Patent  
Cheung et al.

(10) Patent No.: US 8,148,154 B2
(45) Date of Patent: Apr. 3, 2012

(54) METHOD FOR PREPARATION OF SINGLE CHAIN ANTIBODIES

(75) Inventors: Nai-Kong V. Cheung, New York, NY (US); Hong-fen Guo, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 12/709,848

(22) Filed: Feb. 22, 2010

(65) Prior Publication Data

US 2010/0226914 A1 Sep. 9, 2010

Related U.S. Application Data

(62) Division of application No. 10/273,762, filed on Oct. 17, 2002, now Pat. No. 7,666,424.

(60) Provisional application No. 60/330,396, filed on Oct. 17, 2001.

(51) Int. Cl.
*G01N 33/53* (2006.01)
*C12N 15/12* (2006.01)

(52) U.S. Cl. ............ 435/455; 424/130.1; 435/7.1

(58) Field of Classification Search .............. None
See application file for complete search history.

(56) References Cited

U.S. PATENT DOCUMENTS

| 5,270,202 | A | | 12/1993 | Raychaudhuri |
| 5,618,920 | A | * | 4/1997 | Robinson et al. ......... 530/387.1 |
| 5,693,762 | A | | 12/1997 | Queen |
| 6,132,718 | A | | 10/2000 | Hansen |
| 6,326,471 | B1 | | 12/2001 | Kokolus et al. |
| 6,632,431 | B2 | | 10/2003 | Wu |
| 2003/0149998 | A1 | | 8/2003 | Blatcher et al. |

FOREIGN PATENT DOCUMENTS

WO  WO 02/32375  4/2002

OTHER PUBLICATIONS

Paul, Fundamental Immunology, 3rd Edition, 1993, pp. 292-295.*
Rudikoff et al, Proc. Natl. Acad. Sci. USA, 79(6):1979-1983, Mar. 1982.*
MacCallum et al, J. Mol. Biol., 262, 732-745, 1996.*
Casset et al, Biochemical and Biophysical Research Communications, 2003, vol. 307, pp. 198-205.*
Holm et al, Molecular Immunology, 2007, vol. 44, pp. 1075-1084.*
McGuiness et al, Human Gene Therapy 10:165-173, 1999.*
Huston JS, Levinson D, Mudgett-Hunter M, Tai MS, Novotny J, Margolies MN, Ridge RJ, Bruccoleri RE, Haber E, Crea R., "Protein engineering of antibody binding sites: recovery of specific activity in an anti-digoxin single-chain Fv analogue produced in *Escherichia coli*," Proceedings of the National Academy of Sciences of the United States of America 85, 5879-5883 (1988).
Bird RE, Hardman KD, Jacobson JW, Johnson S, Kaufman BM, Lee SM, Lee T, Pope SH, Riordan GS, Whitlow M., "Single-chain antigen-binding proteins," Science 242, 423-426 (1988).
Winter G, Griffiths AD, Hawkins RE, Hoogenboom HR., "Making antibodies by phage display technology," Annual Review of Immunology 12, 433-455 (1994).
Shu L, Qi CF, Schlom J, Kashmiri SV., "Secretion of a single-gene-encoded immunoglobulin from myeloma cells," Proceedings of the National Academy of Sciences of the United States of America 90, 7995-7999 (1993).
Alt M, Muller R, Kontermann RE., "Novel tetravalent and bispecific IgG-like antibody molecules combining single-chain diabodies with the immunoglobulin γ1 Fc or CH3 region," FEBS Letters 454, 90-94 (1999).
Santos AD, Kashmiri SV, Hand PH, Schiom J, Padlan EA., "Generation and characterization of a single gene-encoded single-chain-tetravalent antitumor antibody," Clinical Cancer Research 5, 3118s-3123s (1999).
Eshhar Z, Waks T, Gross G, Schindler DG., "Specific activation and targeting of cytotoxic lymphocytes through chimeric single chains consisting of antibody-binding domains and the gamma or zeta subunits of the immunoglobulin and T-cell receptors," Proceedings of the National Academy of Sciences of the United States of America 90, 720-724 (1993).
Koprowski H, Herlyn D, Lubeck M, DeFreitas E, Sears HF., "Human anti-idiotype antibodies in cancer patients: Is the modulation of the immune response beneficial for the patient?" Proc. Natl Acad Sci, USA 81, 216-219 (1984).
Wagner U, Schlebusch H, Kohler S, Schmolling J, Grunn U, Krebs D., "Immunological responses to the tumor-associated antigen CA125 in patients with advanced ovarian cancer induced by the murine monoclonal anti-idiotype vaccine ACA125," Hybridoma 16, 33-40 (1997). Hombach A, Pohl C, Heuser C, Sircar R, Diehl V, Abken H., "Isolation of single chain antibody fragments with specificity for cell surface antigens by phage display utilizing internal image anti-idiotypic antibodies," J Immunol Methods 218, 53-61 (1998).
Modak S, Kramer K, Humayun G, Guo HF, Cheung NKV., "Monoclonal antibody 8H9 targets a novel cell surface antigen expressed by a wide spectrum of human solid tumors," Cancer Research 61, 4048-4054 (2001).
Powers DB, Amersdorfer P, Poul MA, Nielsen UB, Shalaby R, Adams GP, Weiner LM, Marks JD., "Expression of single-chain Fv-Fc fusions in *Pichia pastoris*," Journal of Immunological Methods 251, 123-135 (2001).

(Continued)

Primary Examiner — Misook Yu
Assistant Examiner — Mark Halvorson
(74) Attorney, Agent, or Firm — Law Offices of Albert Wai-Kit Chan, PLLC

(57) ABSTRACT

This invention provides a method for identifying cells expressing a target single chain antibody (scFv) directed against a target antigen from a collection of cells that includes cells that do not express the target scFv, comprising the step of combining the collection of cells with an anti-idiotype directed to an antibody specific for the target antigen and detecting interaction, if any, of the anti-idiotype with the cells, wherein the occurrence of an interaction identifies the cell as one which expresses the target scFv. This invention also provides a method for making a single chain antibody (scFv) directed against an antigen, wherein the selection of clones is made based upon interaction of those clones with an appropriate anti-idiotype, and heretofore inaccessible scFv so made. This invention provides the above methods or any combination thereof. Finally, this invention provides various uses of these methods.

7 Claims, 16 Drawing Sheets

OTHER PUBLICATIONS

Figure 1:
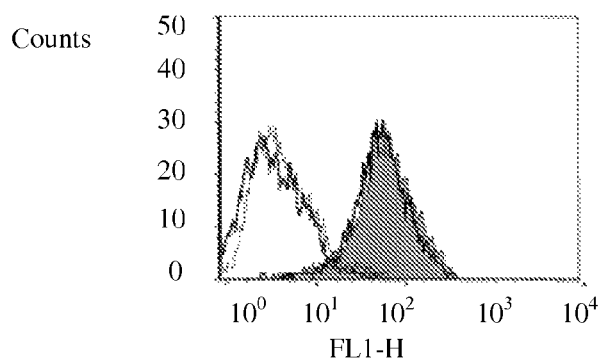
Figure 1:
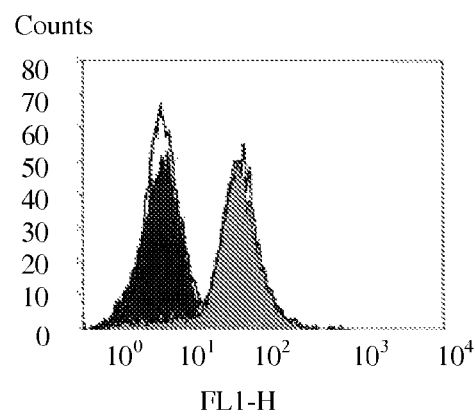
Figure 1:
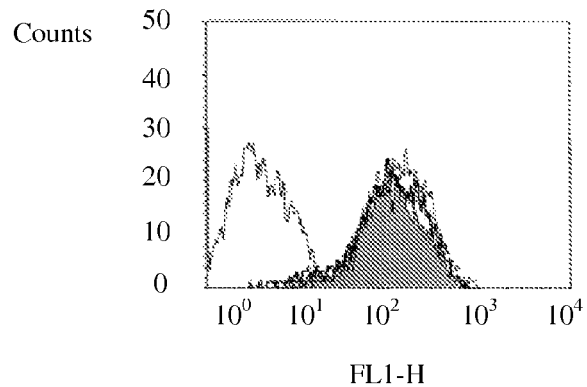

Adams GP, McGartney JE, Tai M-S, Oppermann H, Huston JS, Stafford WF, Bookman MA, Fand I, Houston LL, Weiner LW., "Highly specific in vivo tumor targeting by monovalent and divalent forms of 741F8 anti-c-erbB-2 single-chain Fv." Cancer Research 53, 4026-4034 (1993).

Wu AM, Chen W, Raubitschek A, Williams LE, Neumaier M, Fischer R, Hu SZ, Odom-Maryon T, Wong JY, Shively JE., "Tumor localization of anti-CEA single-chain Fvs: improved targeting by non-covalent dimers," Immunotechnology 2, 21-36 (1996).

Ghetie MA, Podar EM, Ilgen A, Gordon BE, Uhr JW, Vitetta ES., "Homodimerization of tumor-reactive monoclonal antibodies markedly increases their ability to induce growth arrest or apoptosis of tumor cells," Proceedings of the National Academy of Sciences of the United States of America 94: 7509-7514 (1997).

Wright A, Morrison SL., "Effect of glycosylation on antibody function: implications for genetic engineering," Trends in Biotechnology 15, 26-31 (1997).

Umana P, Jean-Mairet J, Moudry R, Amstutz H, Bailey JE., "Engineered glycoforms of an antineuroblastoma IgG1 with optimized antibody-dependent cellular cytotoxic activity," Nature Biotechnology 17, 176-180 (1999).

Ruymann FB, Groves AC., "Progress in the diagnosis and treatment of rhabdomyosarcoma and related soft tissue sarcomas," Cancer Invest 18, 223-41 (2000).

Riddell SR, Watanabe KS, Goodrich JM, et al., "Restoration of viral immunity in immunodeficient humans by the adoptive transfer of T cell clones," Science 257, 238-241 1992).

Walter EA, Greenberg PD, Gilbert MJ, et al., "Reconstitution of cellular immunity against cytomegalovirus in recipients of allogeneic bone marrow by transfer of T-cell clones from the donor," N Engl J Med 333, 1038-1044 (1995).

Heslop HE, Ng CYC, Li C, et al., "Long-term restoration of immunity against Epstein-Barr virus infection by adoptive transfer of gene-modified virus-specific T lymphocytes," Nature Med 2, 551-555 (1996).

Papadopoulos EB, Ladanyi M, Emanuel D, et al., "Infusions of donor leukocytes to treat Epstein-Barr virus-associated lymphoproliferative disorders after allogeneic bone marrow transplantation," N Engl J Med 330, 1185-1191 (1994).

Rosenberg S, Lotze M, Muul L, et al., "A progress report on the treatment of 157 patients with advanced cancer using lymphokine-activated killer cells and interleukin-2 or high-dose interleukin-2 alone," N Engl J Med 316, 889-897 (1988).

Heslop HE, Rooney CM., "Adoptive cellular immunotherapy for EBV lymphoproliferative diseases," Immunological Reviews 157, 217-222 (1997).

Botti et al., "Comparison of three different methods for radiolabelling human activated T lymphocytes," Eur J Nucl Med 24, 497-504 (1997).

Stancovski I, Schindler DG, Waks T, et al., "Targeting of T lymphocytes to Neu/HERe-expressing cells using chimeric single chain Fv receptors," J Immunol 151, 6577-6582 (1993).

Moritz D, Weis W, Mattern J, et al., "Cytotoxic T lymphocytes with a grafted recognition specificity for ERBB2-expressing tumor cells," Proc. Natl Acad Sci, USA 91, 4318-4322 (1994).

Hwu P, Shafer GE, Treisman J, et al., "Lysis of ovarian cancer cells by human lymphocytes redirected with a chimeric gene composed of an antibody variable region and the Fc-receptor gamma-chain," J. Exp. Med. 178, 361-369 (1993).

Eshhar Z, Waks T, Bendavid A, et al., "Functional expression of chimeric receptor genes in human T cells," J Immunol Methods 248, 67-76 (2001).

Rossig C. Bollard CM, Nuchtern JG, et al., Targeting of G(D2)-positive tumor cells by human T lymphocytes engineered to express chimeric T-cell receptor genes. Int J Cancer 94, 228-36 (2001).

Ma Q, Gonzalo-Daganzo RM, Junghans RP., "Genetically engineered T cell as adoptive immunotherapy of cancer," in Giaccone G, Schilsky, R, Sondel, P. (ed),Cancer Chemotherapy and Biological Response Modifiers. Amsterdam, Elsevier Science B.V., (2002).

Fisher B. et al., "Tumor localization of adoptively transferred indium-111 labeled tumor infiltrating lymphocytes in patients with metastatic melanoma," J Clin Oncol 7, 250-261 (1989).

Lacerda JF, Ladanyi M, Louie DC, et al., "Human Epstein-Barr Virus (EBV)-specific cytotoxic T lymphocytes home preferentially to and induce selective regressions of autologous EBV-induced B cell lymphoproliferations in xenografted C.B—17 Scid/Scid mice," J. Exp. Med. 183, 1215-1228 (1996).

Krause A, Guo HF, Tan C, et al., Antigen-dependent CD-28 signaling enhances survival and proliferation in genetically modified activated human primary T lymphocytes. J. Exp. Med. 188, 619-626 (1998).

Finney HM, Lawson ADG, Bebbington CR, et al., "Chimeric receptors providing both primary and costimulatory signaling in T cells from a single gene product," J Immunol 161, 2791-2797 (1998).

Maher J, Brentjens RJ, Gunset G, et al., "Human T-lymphocyte cytotoxicity and proliferation directed by a single chimeric TCRzeta /CD28 receptor," Nat Biotechnol 20, 70-5 (2002).

Mackall C, Berzofsky J, Helman LJ., "Targeting tumor specific translocations in sarcomas in pediatric patients for immunotherapy," Clin Orthop, 25-31 (2000).

Reinhold U, Liu L, Ludtke-Handjery H-C, et al., "Specific lysis of melanoma cells by receptor grafted T cells is enhanced by anti-idiotypic monoclonal antibodies directed to scFv domain of the receptor," Journal of Investigative Dermatology 112, 744-750 (1999).

Koehne G. Gallardo HF, Sadelain M, et al., "Rapid selection of antigen-specific T lymphocytes by retroviral transduction," Blood 96, 109-117 (2000).

Gong JH, Maki G, Klingemann HG., "Characterization of a human cell line (NK-92) with phenotypical and functional characteristics of activated natural killer cells," Leukemia 8, 652-8 (1994).

Tonn T, Becker S, Esser R, et al., Cellular immunotherapy of malignancies using the clonal natural killer cell line NK-92. J Hematother Stem Cell Res 10, 535-44 (2001).

Maki G, Klingernann HG, Martinson JA, et al., "Factors regulating the cytotoxic activity of the human natural killer cell line, NK-92," J Hematother Stem Cell Res 10, 369-83 (2001).

Ugur O, Kothari PJ, Finn RD, et al., "Ga-66 labeled somatostatin analogue DOTA-DPhe1-Tyr3-octreotide as a potential agent for positron emission tomography imaging and receptor mediated internal radiotherapy of somatostatin receptor positive tumors," Nucl Med Biol 29, 147-57 (2002).

Zinn KR, Chaudhuri TR, Krasnykh VN, et al., "Gamma camera dual imaging with a somatostatin receptor and thymidine kinase after gene transfer with a bicistronic adenovirus in mice," Radiology 223, 417-25 (2002).

Tsutsumi A, Takano H, Ichikawa K, et al., "Expression of somatostatin receptor subtype 2 mRNA in human lymphoid cells," Cell Immunol 181, 44-9 (1997).

Elliott DE, Li J, Blum AM, et al., "SSTR2A is the dominant somatostatin receptor subtype expressed by inflammatory cells, is widely expressed and directly regulates T cell IFN-gamma release," Eur J Immunol 29, 2454-63 (1999).

Smanik PA, Liu Q, Furminger TL, et al., "Cloning of the human sodium iodide symporter," Biochem Biophys Res Comm 226, 339-345 (1996).

Kundra V, Mannting F, Jones AG, et al., "Noninvasive monitoring of somatostatin receptor type 2 chimeric gene transfer," J Nucl Med 43, 406-12 (2002).

Koehne G, Zanzonico P, Gallardo HF, et al., "Noninvasive Imaging of human radiolabeled antigen-specific donor T lymphocytes after adoptive immunotherapy in SCID-mice," (Abstrct 2222 Only) Blood 96, (2000).

Yee C, Riddell SR, Greenberg PD., "In vivo tracking of tumor-specific T cells," Curr Opin Immunol 13, 141-146 (2001).

Riddell SR, Elliott M, Lewinsohn DA, et al., "T-cell mediated rejection of gene-modified HIV-specific cytotoxic T lymphocytes in HIV-infected patients," Nat Med 2, 216-223 (1996).

Rossig C, Bollard CM, Nuchtern JG, et al., "Epstein-Barr virus-specific human T lymphocytes expressing antitumor chimeric T-cell receptors potential for improved immunotherapy," Blood 99, 2009-16 (2002).

Koehne G, Doubrovin M, et al., "Serial in vivo imaging of the targeted migration of human HSV-TK-transduced antigen-specific lymphocytes," Nature Biotechnology 21,405-413, (2003).

PCT Notification of Transmittal of the International Search Report or the Declaration for Nai-Kong Cheung and Hong-fen Guo, Int'l App'l No. PCT/US02/33331, Filed on Oct. 17, 2002, Dated Dec. 22, 2003.

Hombach A., et al, Isolation of Single Chain Antibody Fragments with Specificity for Cell Surface Antigens by Phage Display Utilizing Internal Image Anti-Idiotypic Antibodies, J. Immunol Methods, Sep. 1, 1998, vol. 218, No. 1-2, pp. 53-61.

Schlebusch H., et al, Production of a Single-Chain Fragment of the Murine Anti-Idiotypic Antibody ACA125 as Phage-Displayed and Soluble Antibody by Recombinant Phage Antibody Technique, Hybridoma Feb. 1997, vol. 16, No. 1, pp. 47-52.

Zhang W, et al., Production and Characterization of Human Monoclonal Anti-Idiotype Antibodies to Anti-dsDNA Antibodies, Lupus, 2002, vol. 11, No. 6,pp. 362-369.

Cheung et al., 2002, "Anti-idiotypic Antibody as the Surrogate Antigen for Cloning scFv and its Fusion Proteins", Hybridoma and Hybridomics, 21(6):433-443.

Cheung et al., 2000, "Monoclonal Antibody-based Therapy for Neuroblastoma", Current Oncology Reports, 2 (6):547-553.

Supplemental European Search Report for EP 01 98 3999, filed May 16, 2003, for Sloan-Kettering Institute for Cancer Research et al., dated Jul. 26, 2005.

Modak, et al., 1999, "Disialoganglioside GD2 and antigen 8H9: Potential targets for antibody-based immunotherapy against desmoplastic small round cell tumor (DSRCT) and rhabdomyosarcoma (RMS)", Proceedings of the American Association for Cancer Search Annual Meeting, #3133.

Cheung et al., 2003, "Anti-idiotypic Antibody Facilitates scFv Chimeric Immune Receptor Gene Transduction and Clonal Expansion of Human Lymphocytes for Tumor Therapy", Hybridoma and Hybridomics, 22(4):209-218.

Modak et al., 2000, "Novel Tumor Target for Antibody-based Therapy of Rhabdomyosarcoma and Other Pediatric Solid Tumors", Journal of Pediatric Hematology/Oncology, 22(4).

Modak et al., 1998, "Novel Tumor-associated Surface Antigen: Broad Distribution among Neuroectodermal Mesenchymal and Epithelial Tumors with Restructured Distribution in Normal Tissues", Proceedings of ASCO #1716.

Modak et al., 2000, "Monoclonal Antibody 8H9: Specific for a Novel Tumor Antigen on Human Neuroblastoma", Medical and Pediatric Oncology, 35(6).

PCT International Preliminary Examination Report for Sloan-Kettering Institute for Cancer Research, Int'l Application No. PCT/US01/32565, Filed Oct. 18, 2001, Dated Apr. 27, 2006.

Modak at al., 2005, "Radioimmunotargeting of Human Rhabdomyosarcoma Using Monoclonal Antibody 8H9", Cancer Biother Radiopharm, 20(5):534-46.

PCT Written Opinion of the International Preliminary Examining Authority for Sloan-Kettering Institute for Cancer Research, Int'l Application No. PCT/US01/32565, Filed Oct. 18, 2001, Dated Oct. 25, 2005.

PCT Application Publication No. PCT/US97/04427 for Sloan-Kettering Institute for Cancer Research et al., Filed Mar. 20, 1997 for "Single Chain FV Constructs of Anti-ganglioside GD", Published with International Search Report.

European Patent Office Supplementary Search Report for Sloan-Kettering Institute for Cancer Research, Int'l No. PCT/US03/07004, Filed Mar. 4, 2003, Dated Oct. 25, 2005.

Supplementary European Search Report for EP 01 98 3999, filed May 16, 2003, for Sloan-Kettering Institute for Cancer Research et al., dated Jul. 26, 2005.

International Search Report for PCT/US03/07004, filed Mar. 6, 2003, for Sloan-Kettering Institute for Cancer Research et al., dated Jun. 7, 2005.

PCT Notification of Transmittal of the International Search Report or the Declaration for Sloan-Kettering Institute for Cancer Research, et al., Int'l Application No. PCT/US01/32565, Filed on Oct. 18, 2001, dated Apr. 2, 2002.

Juhl, et al., 1997, "Additive Cytotoxicity of Different Monoclonal Antibody-Cobra Venom Factor Conjugates for Human Neuroblastoma Cells," Immunobiology, 197:444-459.

Modak, et al., 2000, "Radioimmunotargeting to Human Rhabdomyosarcoma (RMS) using Monoclonal Antibody (MOAB) 8H9", Proceedings of the American Association for Cancer Research Annual Meeting, 41:724.

Xu, et al., 2000, "Targeting and therapy of carcinoembryonic antigen-expressing tumors in transgenic mice with an antibody-interleukin 2 fusion protein," Cancer Res., 60(16):4475-76.

Pegram et al., 1999, "Combination therapy with trastuzumab (Herceptin) and cisplatin for chemoresistant metastatic breast cancer: evidence for receptor-enhanced chemosensitivity," Sem. Oncol., 26:89-95.

Bigner et al., 1998, "Iodine-131-labeled antitenascin monoclonal antibody 81C6 treatment of patients with recurrent malignant gliomas:phase I trial results," Journal Clincal Oncology, 16:2202-2212.

Bruland et al., 1986, "New monoclonal antibodies specific for human sarcomas," Int. J. Cancer, 15:27-31.

Wang et al., 1995, "Expression of myogenic regulatory proteins(myogenin and MyoD1) in small blue round cell tumors of childhood," Am. J. Pathol., 147:1799-1810.

Bigner et al., 1995, "Phase I studies of treatment of malignant gliomas and neoplastic meningitis with 131 I radiolabeled monoclonal antibodies anti-tenascin 81C6 and anti-chondroitin proteoglycan sulfate Mel-14 (ab')2—a preliminary report," J. Neuro. Oncol., 24:109-122.

Mariani et al., 1997, "A pilot pharmacokinetic and immunoscintigraphic study with the technetium-99m-labeled monoclonal antibody BC-1 directed against oncofetal fibronectin in patients with brain tumors," Cancer Supplement, 80:2484-2489.

DiMaggio et al., 1990, Monoclonal antibody therapy of cancer. In: Pinedo HM, Chabner BA, Longo DL, (eds.): Cancer Chemotherapy and Biological Response Modifiers, Annual 11, Elsevier Science Publishers B.V., (Biomedical Division), pp. 177-203.

Schlom, J. 1995, "Monoclonal Antibodies in cancer therapy: Basic principles." In: DeVita VT, Hellman S, Rosenberg SA, (eds.): Biologic therapy of cancer, 2nd ed. Philadelphia, J.B.Lippincott Co, pp. 507-520.

Lode et al., 1998, "Immunocytokines: A promising approach to cancer immunotherapy," Pharmacology Therapeutics, 80:277-292.

Erikson et al., 1988, "Hexabrachion protein (tenascin, cytotactin, brachionectin) in connective tissues, embryonic tissues and tumors," Adv. Cell Biol., 2:55-90.

Modak et al., 1998, "Novel tumor-associated surface antigen: broad distribution among neuroectodermal, mesenchymal and epithelial tumors, with restricted distribution in normal tissues," Proceedings of ASCO, 17:449a.

Cheung et al., 1997, "Treatment of advanced stage neuroblastoma." In: Reghavan D, Scher HI, Leibel SA, Lange P, (eds.): Principles and Practice of Genitourinary Oncology. Philadelphia, J.B. Lippincott Company, pp. 1101-1111.

Brodeur et al., 1997, "Neuroblastoma." In: Pizzo PA, Poplack DG, (eds.): Principles and Practice of Pediatric Oncology, 3rd ed. Philadelphia, J.B. Lippincott Company, pp. 761-797, chapter 29.

Cheung, Nai-Kong V., 1997, "Biological and molecular approaches to diagnosis and treatment, Section I. Principles of Immunotherapy." In: Pizzo PA, Poplack DG, (eds.): Principles and Practice of Pediatric Oncology, 3rd ed. ed. Philadelphia, J.B. Lippincott Company, pp. 323-342.

Larson et al., 1995, "Antibodies in cancer therapy: Radioisotope conjugates." In: DeVita VT, Hellman S, Rosenberg SA, (eds.): Biologic Therapy of Cancer, 2nd ed. Philadelphia, J.B.Lippincott Co., pp. 534-552.

Reisfeld et al., 1994, "Potential of genetically engineered anti-ganglioside GD2 antibodies for cancer immunotherapy." In: Progress in Brain Search (Svennerhol,L, Asbury,AK, Reisfeld,RA, Sandhoff,K, Suzuki,K, Tettamani,G, Toffano,G, vol. 101. Cambridge, UK, Elsevier Trends Journals, pp. 201-212.

Cheung et al., 1988, "Decay-accelerating factor protects human tumor cells from complement-mediated cytotoxicity in vitro," J. Clin. Invest., 81:1122-1128.

Murray et al., 1994, "Phase I trial of murine monoclonal antibody 14G2a administered by prolonged intravenous infusion in patients with neuroectodermal tumors," Journal of Clinical Oncology, 12(1):184-193.

Ugur et al., 1996, "Comparison of the targeting characteristics of various radioimmunoconjugates for radioimmunotherapy of neuroblastoma: Dosimetry calculations incorporating cross-organ beta doses," Nucl. Med. Biol., 23:1-8.

Saleh et al., 1995, "Phase I trial of the murine monoclonal anti-GD2 antibody 14G2a in metastatic melanoma," Cancer Research, 52:4342-4347.

Handgretinger et al., 1995, "A phase I study of human/mouse chimeric antiganglioside GD2 antibody ch14.18 in patients with neuroblastoma," Eur. J. Cancer, 31:261-267.

Cheung et al., "3F8 monoclonal antibody treatment of patients with stage IV neuroblastoma: a phase II study," In: Evans AE, Guillio JD, Biedler JL, et al, (eds.): Advances in Neuroblastoma Research, vol. 4. New York, Wiley Liss, 1994, pp. 319-329.

Yu et al, 1991, "Phase I clinical trial of ch14.18 in patients with refractory neuroblastoma," Proc. Am. Soc. Clin. Oncol., 10:318.

Cheung et al., "Biological and Molecular Approaches to Diagnosis and Treatment. Immunotherapy," In: Pizzo PA, Poplack DG, (eds.): Principles and Practice of Pediatric Oncology, 2nd ed. Philadelphia, J. B. Lippincott Company, 1992, pp. 357-370.

Cheung et al., 1998, "3F8 monoclonal antibody treatment of patients with stage IV neuroblastoma: A phase II Study," Int. J. Oncol., 12:1299-1306.

Cheung et al., "Phase I study of radioimmunotherapy of neuroblastoma using iodine 131 labeled 3F8." In: Prog. Olin. Biol. Res: Advances in Neuroblastoma Research 4. New York, Wiley Liss, 1994, pp. 329.

Kramer et al., 1996, "Pharmacokinetics and acute toxicology of intraventricular 131I-monoclonal antibody targeting disialoganglioside in non-human primates," J. Neuro. Oncol., 35:101-111.

Saleh et al., 1992, "Phase I trial of chimeric anti-GD2 monoclonal antibody C14.18 in patients with metastatic melanoma," Hum. Antibod. Hybridomas, 3:19-24.

Cheung et al., 1999, "Induction of Ab3' following anti-GD2 monoclonal antibody 3F8 therapy predicts survival among patients (pts) with advanced neuroblastoma," Proc. Am. Assoc. Cancer Res., 40:574, 1999.

Chen et al., 1999, "Surface antigen expression and complement susceptibility of differentiated neuroblastoma clones," Am. J. Pathol.

Sgouros et al., 1996, "Hematologic toxicity in radioimmunotherapy: An evaluation of different predictive measures," J. Nucl. Med., 37:43-44.

Sgouros G, "Treatment planning for internal emitter therapy: methods, applications and clinical implications.," Proceedings of th 6th International Radiopharmaceutical Dosimetry Symposium, May 7-10, 1996, Gatlinburg, TN:13-24.

Sgouros G, 1998, "Yttrium-90 biodisribution by yttrium-87 imaging: a feasibility analysis," Medical Physics, 25(8):1487-1490.

Meyer et al., "Demonstration of accuracy and clinical versatility of mutual information for automatic multimodality image fusion using affine and thin-plate spline warped geometric deformations," Medical Image Analysis, 1:195-206, 1997.

Burdach et al., 1996, "Myeloablative therapy, stem cell rescue and gene transfer in advanced Ewing tumors," Bone Marrow Transplant, 18 Suppl. 1:S67-8.

Ladenstein et al., "Impact of megatherapy in children with high-risk Ewing's tumours in complete remission: a report from the EBMT Solid Tumour Registry [published erratum appears in Bone Marrow Transplant Sep. 1996;18(3):675]." Bone Marrow Transplant. 1995;15:697-705.

Ladenstein Ret al., 1997, "Autologous stem cell transplantation for solid tumors in children," Curr. Opin. Pediatr., 9:55-69.

Laws et al., 1999, "Multimodality diagnostics and megatherapy in poor prognosis Ewing's tumor patients. A single-center report," Strahlenther Onkol., 175:488-94.

Pape et al., 1999, "Radiotherapy and high-dose chemotherapy in advanced Ewing's tumors," Strahlenther Onkol., 175:484-7.

Pession et al., 1999, "Phase I study of high-dose thiotepa with busulfan, etoposide, and autologous stem cell support in children with disseminated solid tumors," Med. Pediatr. Oncol., 33:450-4.

Stewart et al., 1996, "High-dose melphalan +/- total body irradiation and autologous hematopoietic stem cell rescue for adult patients with Ewing's sarcoma or peripheral neuroectodermal tumor," Bone Marrow Transplant, 18:315-8.

Rill et al., 1994, "Direct demonstration that autologous bone marrow transplantation for solid tumors can return a multiplicity of tumorigenic cells," Blood, 84:380-3.

Brenner et al., 1993, "Gene-marking to trace origin of relapse after autologous bone-marrow transplantation," The Lancet, 341:85-6.

Mackall et al., 1999, "Combined Immune Reconstitution/Tumor Vaccination to induce anti-tumor immune responses in the setting of minimal residual neoplastic disease," Blood, 94:133a.

Quinones et al., 1993, "Extended-cycle elutriation to adjust T-cell content in HLA-disparate bone marrow transplantation," Blood, 82:307-17.

Kontny et al., 1998, "Simultaneous expression of Fas and nonfunctional Fas ligand in Ewing's sarcoma," Cancer Res., 58:5842-9.

De Wynter et al., 1995, "Comparison of purity and enrichment of CD34+ cells from bone marrow, umbilical cord and peripheral blood (primed for apheresis) using five separation systems," Stem Cells., 13:524-32.

Dworzak et al., 1994, "Flow cytometric assessment of human MIC2 expression in bone marrow, thymus, and peripheral blood," Blood, 83:415-25.

De Leij et al., 1994, "SCLC-cluster-2 antibodies detect the pancarcinoma/epithelial glycoprotein E GP-2," (supplement) Int. J. Cancer, 8: 60-3.

Gerald et al., 1991, "Intra-abdominal desmoplastic small round-cell tumors: report of 19 cases of distinctive type of high-grade polyphenotypic malignancy affecting young individuals," Am. J. Surg. Pathol., 15(6): 499-513.

Lee et al., 1997, "The EWS-WT1 translocation product induces PDGFA in desmoplastic small round-cell tumour," Nat. Genet., 17:309-13.

Burton et al., 1994, "Human antibodies from combinatorial libraries," Advances in Immunology, 57: 191-280.

George et al., 1994, "Applications of Monoclonal Antibodies in Clinical Oncology," Immunology Today, 15: 559-561.

Kipriyanov et al., 1995, Single-chain antibody streptavidin fusions: tetrameric bifunctional scFv-complexes with biotin binding activity and enhanced affinity to antigen, Human Antibodies Hybridomas, 6: 93-101.

Daniel et al., 1997, "Costimulatory signals through B7.1/CD28 prevent T cell apoptosis during target cell lysis," J. Immunol., 159: 3808-3815.

Rosenberg, S. A., 1995, "Cell transfer therapy: clinical applications." In: V. T. J. DeVita, S. Hellman, and S. A. Rosenberg (eds.), Biologic therapy of cancer, second edition, pp. 487-506, Philadelphia: J. B. Lippincott Company.

Yang et al., 1997, "A new class of antigen-specific killer cells," Nat. Biotechnol., 15:46-51.

Culver et al., 1992, "In vivo gene transfer with retroviral vector-producer cells for treatment of experimental brain tumors," Science, 256:1550.

Jensen et al., 1998, "CD20 is a molecular target for scFvFc: receptor redirected T cells: implications for cellular immunotherapy of CD20+ malignancy," Biol. Blood Marrow Transplant, 4:75-83.

Fitzer-Attas et al., 1998, "Tyrosine kinase chimeras for antigen-selective T-body therapy," Adv. Drug Deliv. Rev., 31:171-182.

Valitutti et al., 1997, "Serial triggering of TCRs: a basis for the sensitivity, and specificity of antigen recognition," Immunology Today, 18:299-304.

Cheung et al., 1987, "Targeting of ganglioside GD2 monoclonal antibody to neuroblastoma," J. Nuc. Med., 28:1577-83.

Thomson et al., 1999, "RT-PCR evaluation of peripheral blood, bone marrow and peripheral blood stem cells in children and adolescents undergoing VACIME chemotherapy for Ewing's sarcoma and alveolar rhabdomyosarcoma," Bone Marrow Transplant, 24:527-33.

Athale et al., 2001, "Use of Reverse Transcriptase Polymerase Chain Reaction for Diagnosis and Staging of Alveolar Rhabdomyosarcoma, Ewing Sarcoma Family of Tumors, and Desmoplastic Small Round Cell Tumor," Am. J. Pediatr. Hematol. Oncol., 23(2):99-104.
Gruchala et al., 1997, "Rhabdomyosarcoma. Morphologic, immunohistochemical, and DNA study," Gen. Diagn. Pathol. 1142:175-84.
Kalebic et al., 1994, "In vivo treatment with antibody against IGF-1 receptor suppresses growth of human rhabdomyosarcoma and down-regulates p34cdc2," Cancer Res., 54:5531-4.
Queen et al., 1989, "A Humanized Antibody that Binds to the Interleukin 2 Receptor," PNAS, 86(24):10029-10033.
Alvarez-Vallina et al., 1996, "Antigen-specific targeting of CD28 receptors," European Journal of Immunology, 26(10):2304-2309.
Heppeler et al., 1999, "Radiometal-labelled macrocyclic chelator-derivatized somatostatin analogue with superb tumour-targetting properties and potential for receptor-mediated internal radiotherapy," Chemistry—A European Journal, 5(7):1974-1981.
U.S. Office Action for Nei-Kong V. Cheung, U.S. Appl. No. 10/097,558, filed Mar. 8, 2002, Dated Jul. 26, 2006.
Cheung et al., 1998, "Anti-GD2 antibody treatment of minimal residual stage 4 neuroblastoma diagnosed at more than 1 year of age," J. Clin. Oncol., 16:3053-3060.
Yu et al., 1998, "Phase I trial of a human-mouse chimeric anti-disialoganglioside monoclonal antibody ch14.18 in patients with refractory neuroblastoma and osteosarcoma," J. Clin. Oncol., 16:2169-2180.
Jurcic et al., 1995, "Sequential targeted therapy for acute promyelocytic leukemia with all-trans retinoic acid and anti-CD33 monoclonal antibody M195," Leuk., 9:244-248.
Czuczman et al., 1999, "Treatment of patients with low-grade B-cell lymphoma with the combination of chimeric anti-CD20 monoclonal antibody and CHOP chemotherapy," J. Clin. Oncol., 17:268-276.
Garin-Chesa et al., 1991, "Immunohistochemical analysis of neural cell adhesion molecules. Differential expression in small round cell tumors of childhood and adolescence," Am. J. Pathol., 139:275-286.
Ritter et al., 1991, "Ganglioside antigens expressed by human cancer cells," Semin. Cancer. Biol., 2:401-409.
Ylagan et al., 1997, "CD44 expression in astrocytic tumors," Modern Pathology, 10:1239-1246.
Kuan et al., 1999, "125I-labeled anti-epidermal growth factor receptor vIII single-chain Fv exhibits specific and high-level targeting of glioma xenografts," Clin. Can. Res., 5:1539-1549.
Richardson et al., 1986, "Radioimmunolocalization of human brain tumors. Biodistribution of radiolabelled monoclonal antibody UJ13A," Eur. J. Nucl. Med., 12:313-320.
Papanastassiou et al. 1993, "Treatment of recurrent and cystic malignant gliomas by a single intracavitary injection of 131I-monoclonal antibody: Feasibility, pharmacokinetics and dosimetry," Br. J. Cancer, 67:144-151.
Celis et al., 1994, "Induction of anti-tumor cytotoxic T lymphocytes in normal humans using primary cultures and synthetic peptide epitopes," Proc. Natl. Acad. Sci. USA, 91:2105-2109.
Riva et al., 1999, "131I radioconjugated antibodies for the locoregional radioimmunotherapy of high-grade malignant glioma—phase I and II study," Acta Oncol., 38:351-359.
Heiner et al., 1987, "Localization of GD2 specific monoclonal antibody in human osteogenic sarcoma," Cancer Res., 47:5377-5381.
Spendlove et al., 1999, "Decay accelerating factor (CD55): a target for cancer vaccines?" Cancer Res., 59:2282-2286.
Weidner et al., 1994, "Immunohistochemical profile of monoclonal antibody O13 that recognizes glycoprotein 930/32MIC2 and is useful in diagnosing Ewing's sarcoma and peripheral neuroepithelioma," American Journal of Surgical Pathology, 18:486-494.
Hatzubai et al., 1981, "The use of a monoclonal anti-idiotype antibody to study the biology of human B-cell lymphoma," J. Immunol., 126:2397-2402.
Cheung et al., 1985, "Monoclonal antibodies to a glycolipid antigen on human neuroblastoma cells," Cancer Res., 45:2642-2649.
Kramer et al., 1996, "Prognostic value of TrkA protein detection my monoclonal antibody 5C3 in Neuroblastoma," Clin. Can. Res., 2:1361-1367.
Hecht et al., 1985, "Production and characterization of a monoclonal antibody that binds Reed-Sternberg cells," J. Immunol., 134:4231-4236.

Seeger et al., 1982, "Definition of a Thy-1 determinant on human neuroblastoma, glioma, sarcoma, and teratoma cells with a monoclonal antibody," J. Immunol., 128:983-989.
Kaaijk et al., 1995, "Expression of CD44 splice variants in human primary brain tumors," Journal of Neuro-Oncology, 26:185-190.
Wikstrand et al., 1993, "Lactotetraose series ganglioside 3',6'-isoLD1 in tumors of central nervous and other systems in vitro and in vivo," Cancer Res., 53:120-126.
Pappo et al., 1997, "Rhabdomyosarcoma: biology and treatment," Pediatr. Clin. North Am., 44:953-972.
Fujisawa et al., 1989, "A monoclonal antibody with selective immunoreactivity for neuroblastoma and rhabdomyosarcoma," Proc. Am. Assoc. Cancer Res., 30:345.
Wikstrand et al., 1995, "Monoclonal Antibodies against EGFRvIII are Tumor Specific and React with Breast and Lung Carcinomas and Malignant Gliomas," Cancer Res., 55:3140-48.
Kishima et al., 1998, "Monoclonal antibody ONS-21 recognizes integrin a3 in gliomas and gliomas and medulloblastomas," Br. J. Cancer, 79:333-339.
Moriuchi et al., 1993, "Characterization of a new mouse monoclonal antibody (ONS-M21) reactive with both medulloblastomas and gliomas," Br. J. Cancer, 68:831-837.
Kondo et al., 1992, "Human glioma-specific antigens detected by monoclonal antibodies," Neurosurgery, 30:506-511.
Dastidar et al., 1995, "Monoclonal antibody against human glioblastoma multiforme (U-87Mg) immunoprecipitates a protein of monoclonal mass 38KDa and inhibits tumor growth in nude mice," J. Neuroimmunol., 56:91-98.
Mihara et al., 1992, "Monoclonal antibody against ependymoma-derived cell line," Journal of Neuro-Oncology, 12:1-11.
Daghighian et al., 1993, "Development of a method to measure kinetics of radiolabeled monoclonal antibody in human tumour with applications to microdosimetry: positron emission tomography studies of iodine-124 labeled 3F8 monoclonal antibody in glioma," Eur. J. Nucl. Med., 20:402-409.
Plate et al., 1992, "Platelet derived growth factor b is induced during tumor development and upregulated during tumor progressing in endothelial cells in human gliomas," Lab. Invest., 67:529-534.
Yang et al., 1993, "Expression of 300-kilodalton intermediate filament-associated protein distinguishes human glioma cells from normal astrocytes," Proceedings of the National Academy of Sciences of the United States of America, 90:8534-8537.
Koehler et al., 1975, "Continuous culture of fused cells secreting antibody of pre-defined specificity," Nature 256:495-496.
Moffat et al., 1996, "Clinical utility of external immunoscintigraphy with the IMMU-4 technetium-99m Fab' antibody fragment in patients undergoing surgery for carcinoma of the colon and rectum:results of a pivotal, phase III trial," The Immunomedics Study Group. J. Clin. Oncol., 14(8):2295-2305.
Maloney et al., 1997, "IDEC-C2B8: Results of a phase I multiple-dose trial in patients with relapsed non-hodgkin's lymphoma," J. Clin. Oncol. 15:3266-3274.
Cobleigh et al., 1999, "Multinational study of the efficacy and safety of humanized anti-HER2 monoclonal antibody in women who have HER2-overexpressing metastatic breast cancer that has progressed after chemotherapy for metastatic disease," J. Clin. Oncol. 17:2639-2648.
Meredith et al., 1996, "Phase II study of dual 131I-labeled monoclonal antibody therapy with interferon in patients with metastatic colorectal cancer," Clin. Can. Res. 2:1811-1818.
Yeh et al., 1991, "Radioimmunodetection of neuroblastoma with iodine-131-3F8: Correlation with biopsy, iodine-131-Metaiodobenzylguanidine (MIBG) and standard diagnostic modalities," J. Nucl. Med. 32:769-776.
Wheldon et al., 1991, "As: The curability of tumors of differing size by targeted radiotherapy using 131-I or 90-Y," Radiother. Oncol. 21:91-99.
Wilder et al., 1996, "Radioimmunotherapy: recent results and future directions," J. Clin. Oncol. 14:1383-1400.
Zalutsky et al., 1994, "Radioimmunotherapy of neoplastic meningitis in rats using an alpha-particle-emitting immunoconjugate," Cancer Res. 54:4719-4725.

McDevitt et al., 1998, "Radioimmunotherapy with alpha-emitting nuclides," Eur. J. Nucl. Med. 25:1341-1351.

DeNardo et al., 1999, "Antibody phage libraries for the next generation of tumor targeting radioimmunotherapeutics," Clin. Can. Res. 5:3213s-3218s.

DeNardo et al.. 1999, "Phage Library-derived human anti-TETA anti anti-DOTA ScFv for pretargeting RIT," Hybridoma 18:13-21.

Eshar et al., 1993, "Specific activation and targeting of cytotoxic lymphocytes through chimeric single chains consisting of antibody-binding domains and the or zeta subunits of the immunoglobulin and T-cell receptors," Proc. Natl. Acad. Sci. USA 90:720-24.

Altenschmidt et al., 1996, "Cytolysis of tumor cells expressing the Neu/erbB-2, erbB-3, and erbB-4 receptors by genetically targeted naive T lymphocytes," Clin. Can. Res. 2:1001-1008.

Krause et al., 1998, "Antigen-dependent CD-28 signaling enhances survival and proliferation in genetically modified activated human primary T lymphocytes," J. Exp. Med. 188:619-626.

Price et al., 1984, "Characteristics of the cell surface antigen p72, associated with a variety of human tumors and mitogen-stimulated T-lymnphoblasts," FEBS Letters, 171:31-35.

Gorlick et al., 1999, "Expression of HER2/erbB-2 correlates with survival in osteosarcoma," J. Clin. Oncol. 17:2781-2788.

Cheung et al., 1997, "Detection of metastatic neuroblastoma in bone marrow: when is routine marrow histology insensitive?," J. Clin. Oncol. 15:2807-2817.

Ghossein et al., 1999, "Detection of circulating prostatic tumor cells using immunobead reverse transcriptase polymerase chain reaction for prostatic specific membrane antigen mRNA," Diag. Mol. Path. 8:59-65.

Leung et al., 1998, "Frequent detection of tumor cells in hematopoietic grafts in neuroblastoma and ewing's sarcoma," Bone Marrow Transpl., 22:971-979.

Mueller et al., 1990, "Enhancement of antibody-dependent cytotoxicity with a chimeric anti-GD2 antibody," J. Immunol. 144:1382-1386.

Santos et al., 1999, "Generation and characterization of a single gene-encoded single-chain-tetravalent antitumor antibody," Clin. Can. Res. 5:3118s-3123s.

Guo et al., 1996, "Recombinant anti-ganglioside GD2 scFv-streptavidin fusion protein for tumor pretargeting," Proc. Am. Assoc. Cancer Res., 37:469.

Fagnou et al., 1998, "Presence of tumor cells in bone marrow but not in blood is associated with adverse prognosis in patients with Ewing's tumor," J. Clin. Oncol., 16:1707-1711.

Munn et al., 1987, "Interleukin-2 enhancement of monoclonal antibody-mediated cellular cytotoxicity (ADCC) against human melanoma," Cancer Res., 47:6600-6605.

Hank et al., 1990, "Augmentation of antibody dependent cell mediated cytotoxicity following in vivo therapy with recombinant interleukin-2," Cancer Res., 50:5234-5239.

Kushner et al., 1989, "GM-CSF enhances 3F8 monoclonal antibody-dependent cellular cytotoxicity against human melanoma and neuroblastoma," Blood, 73:1936-1941.

Kushner et al., 1992, "Absolute requirement of CD11/CD18 adhesion molecules, FcRII and phosphatidylinositol-linked FcRIII for monoclonal antibody-mediated neutrophil anti-human tumor cytotoxicity," Blood 79:1484-1490.

Saarinen et al., 1985, "Eradication of neuroblastoma cells in vitro by monoclonal antibody and human complement: method for purging autologous bone marrow," Cancer Res., 45:5969-5975.

Munn et al., 1989: "Antibody-dependent antitumor cytotoxicity by human monocytes cultured with recombinant macrophage colony-stimulating factor. Induction of efficient antibody-mediated antitumor cytotoxicity not detected by isotope release assays," J. Exp. Med., 170:511-526.

Munn et al., 1990, "Phagocytosis of tumor cells by human monocytes cultured in recombinant macrophage colony-stimulating factor," J. Exp. Med., 172:231-237.

Sabzevari et al., 1994, "A recombinant antibody-interleukin 2 fusion protein suppresses growth of hepatic human neuroblastoma metastases in severe combined immunodeficiency mice," Proceedings of the National Academy of Science USA, 91:9626-9630.

Mujoo et al., 1991, "A potent and specific immunotoxin for tumor cells expressing disialoganglioside GD2," Cancer Immunol. Immunother., 34:198-204.

Gottstein et al., 1994, "Antidisialoganglioside Ricin A-chain immunotoxins show potent anti-tumor effects in vitro and in a disseminated human neuroblastoma severe combined immunodeficiency mouse model," Cancer Res., 54:6186-6193.

Holzer et al., 1995, "Superantigen-staphylococcal-enterotoxin-A-dependent and antibody-targeted lysis of GD2-positive neruoblastoma cells," Cancer Immunol. Immunother., 41:129-136.

Cheung et al., 1987, "Ganglioside GD2 specific monoclonal antibody 3F8—a phase I study in patients with neuroblastoma and malignant melanoma," J. Clin. Oncol., 5:1430-1440.

Cheung et al., 1992, "Reassessment of patient response to monoclonal antibody 3F8," J. Clin. Oncol., 10:671-672.

Murray et al., 1994, "Phase I trial of murine monoclonal antibody 14G2a administered by prolonged intravenous infusion in patients with neuroectodermal tumors," J. Clin. Oncol., 12:184-193.

Uttenreuther-Fischer et al., 1995, "Pharmacokinetics of anti-ganglioside GD2 mAb 14G2a in phase 1 trial in pediatric cancer patients," Cancer Immunol. Immunother., 41:29-36.

Handgretinger et al., 1992, "A phase I study of neuroblastoma with the anti-ganglioside GD2 antibody 14.G2a," Cancer Immunol. Immunother., 35:199-204.

Miraldi et al., 1986, "Diagnostic imaging of human neuroblastoma with radiolabeled antibody," Radiology, 161:413-418.

Arbit et al., 1991, "Quantitative Immunoimaging of gliomas in humans with anti-ganglioside monoclonal antibodies," J. Neurosurg., 76:399a.

Grant et al., 1996, "Radioimmunodetection of small-cell lung cancer using the anti-GD2 ganglioside monoclonal antibody 3F8: a pilot trial," Eur. J. Nucl. Med., 23:145-149.

Larson et al., 1992, "PET scanning of iodine-124-3F8 as an approach to tumor dosimetry during treatment planning for radioimmunotherapy in a child with neuroblastoma," J. Nucl. Med., 33:2020-2023.

Pentlow et al., 1991, "Quantitative imaging of I-124 using positron emission tomography with applications to radioimmunodiagnosis and radioimmunotherapy," Medical Physics, 18:357-366.

Pentlow et al., 1996, "Quantitative imaging of iodine-124 with PET," J. Nucl. Med., 37:1557-1562.

Saleh et al, 1992, "A phase I trial of the murine monoclonal anti-GD2 antibody 14.G2a in metastatic melanoma," Cancer Res 52:4342-4347.

Cheung et al, 1994, "Antibody response to murine anti-GD2 monoclonal antibodies: Correlation with patient survival," Cancer Res., 54:2228-2233.

Drengler et al., 1999, "Phase I and pharmacokinetic trial of oral irinotecan administered daily for 5 days every 3 weeks in patients with solid tumors," J. Clin. Oncol., 17:685-696.

Cheung et al., 1986, "Complete tumor ablation with iodine 131-radiolabeled disialoganglioside GD2 specific monoclonal antibody against human neuroblastoma xenografted in nude mice," J. Natl. Cancer Inst. 77:739-745.

Cheung et al., 1993, "Disialoganglioside GD2 anti-idiotypic monoclonal antibodies," Int. J. Cancer, 54:499-505.

Loh et el., 1998, "A pharmacokinetic model of 131I-G250 antibody in patients with renal cell carcinoma," J. Nucl. Med., 3:484-489.

Kolbert et al., 1997, "Implementation and evaluation of patient-specific three dimensional internal dosimetry," J. Nucl. Med., 38:301-308.

Sgouros et al., "Bone marrow dosimetry: Regional variability of marrow-localizing antibody," J. Nucl. Med., 37:695-698, 1996.

Sgouros at al., 1997, "Marrow and whole-body absorbed dose vs marrow toxicity following 131I-G250 antibody therapy in patients with renal-cell carcinoma," J. Nucl. Med. 38:252P.

Furhang et al., 1996, "Radionuclide photon dose kernels for internal emitter dosimetry," Medical Physics, 23:759-764.

Furhang et al., 1996, "A monte carlo approach to patient-specific dosimetry," Medical Physics, 23:1523-1529.

Furhang et al., 1997, "Implementation of a monte carlo dosimetry method for patient-specific internal emitter therapy," Medical Physics, 24:1163-1172.

Scott et al., 1995, "Image registration of SPECT and CT images using an external fiduciary band and three-dimensional surface fitting in metastatic thyroid cancer," J. Nucl. Med., 36:100-103.

Sgouros et al., 1993, "Three-dimensional dosimetry for radioimmunotherapy treatment planning," J. Nucl. Med., 34:1595-1601.

Arndt et al., 1999, "Common musculoskeletal tumors of childhood and adolescence," N. Engl. J. Med., 341:342-52.

West et al., 1997, "Detection of circulating tumor cells in patients with Ewing's sarcoma and peripheral primitive neuroectodermal tumor," J. Clin. Oncol., 15:583-8.

De Alava et al., 1998, "Ewing family tumors: potential prognostic value of reverse-transcriptase polymerase chain reaction detection of minimal residual disease in peripheral blood samples," Diagn. Mol. Pathol., 7:152-7.

Toretsky et al., 1995, "Detection of (11;22)(q24;q12) translocation-bearing cells in peripheral blood progenitor cells of patients with Ewing's sarcoma family of tumors," J. Natl. Cancer Inst., 87:385-6.

Burdach et al., 1993, "Myeloablative radiochemotherapy and hematopoietic stem-cell rescue in poor-prognosis Ewing's sarcoma," J. Clin. Oncol., 11:1482-8.

Chan et al., 1997, "High-dose sequential chemotherapy and autologous stem cell reinfusion in advanced pediatric solid tumors," Bone Marrow Transplant, 20:1039-43.

Fischmeister et al., 1999, "Low incidence of molecular evidence for tumour in PBPC harvests from patients with high risk Ewing tumours," Bone Marrow Transplant., 24:405-9.

Horowitz et al., 1993, "Total-body irradiation and autologous bone marrow transplant in the treatment of high-risk Ewing's sarcoma and rhabdomyosarcoma," J. Clin. Oncol., 11:1911-8.

Perentesis et al., 1999, "Autologous stem cell transplantation for high-risk pediatric solid tumors," Bone Marrow Transplant. 24:609-15.

Chirgwin et al., 1979; "Isolation of biologically active ribonucleic acid from sources enriched in ribonuclease," Biochemistry, 18:5294-9.

Mackall et al., 1997, "Pathways of T-cell regeneration in mice and humans: implications for bone marrow transplantation and immunotherapy," Immunol. Rev., 157:61-72.

Vogel et al., 2000, "Clinical applications of CD34(+) peripheral blood progenitor cells (PBPC). Stem Cells," 18:87-92.

Dyson et al., 2000, "CD34+ selection of autologous peripheral blood stem cells for transplantation following sequential cycles of high-dose therapy and mobilisation in multiple myeloma," Bone Marrow Transplant, 25:1175-84.

Emig et al., 1999, "Accurate and rapid analysis of residual disease in patients with CML using specific fluorescent hybridization probes for real time quantitative RT-PCR," Leukemia, 13:1825-32.

Mensink et al., 1998, "Quantitation of minimal residual disease in Philadelphia chromosome positive chronic myeloid leukaemia patients using real-time quantitative RT-PCR," Br. J. Haematol., 102:768-74.

Pongers-Willemse et al., 1998, "Real-time quantitative PCR for the detection of minimal residual disease in acute lymphoblastic leukemia using junctional region specific TaqMan probes," Leukemia, 12:2006-14.

Branford et al., 1999, "Monitoring chronic myeloid leukaemia therapy by real-time quantitative PCR in blood is a reliable alternative to bone marrow cytogenetics," Br. J. Haematol., 107:587-99.

Chang et al., 1992, "Expression of disialogangliosides GD2 and GD3 on human soft tissue sarcomas," Cancer, 70:633-8.

Froberg et al., 1999, "Intra-abdominal desmoplastic small round cell tumor: immunohistochemical evidence for up-regulation of autocrine and paracrine growth factors," Ann. Clin. Lab. Sci., 29:78-85.

Heiner et al., 1987, "Localization of GD2-specific monoclonal antibody 3F8 in human osteosarcoma," Cancer Res., 47:5377-81.

Kushner et al., 1996, "Desmoplastic small round-cell tumor: prolonged progression-free survival with aggressive multimodality therapy," J. Clin. Oncol., 14: 1526-31.

Ladanyi et al., 1994, "Fusion of the EWS and WT1 genes in the desmoplastic small round cell tumor," Cancer Res., 54: 2837-40.

Gerald et al., 1991, "Intrabdominal desmoplastic small round cell tumor. Report of 19 cases of a distinctive type of high-grade polyphenotypic malignancy affecting young individuals," Am. L. Surg. Pathol., 15,499-513.

Gerald et al., 1998, "Clinical pathologic, and molecular spectrum of tumors associated with t(11;22) (p13;q12): desmoplastic small round-cell tumor and its variants," J. Clin. Oncol., 16: 3028-36.

Ordonez et al., 1993, "Intra-abdominal desmoplastic small cell tumor: a light microscopic, immunocytochemical, ultrastructural, and flow cytometric study," Hum. Pathol., 24,850-65.

Ordonez, N.G., 1998, "Desmoplastic small round cell tumor: II: an ultrastructural and immunohistochemical study with emphasis on new immunohistochemical markers," Am. J. Surg. Pathol., 22:1314-27.

Adams et al., 1993, "Highly specific in vivo tumor targeting by monovalent and divalent forms of 741F8 anti-c-erbB-2 single-chain Fv," Cancer Research, 53: 4026-4034.

Alt et al., 1999, "Novel tetravalent and bispecific IgG-like antibody molecules combining single-chain diabodies with the immunoglobulin γ1 Fc or CH3 region," FEBS Letters, 454:90-94.

Bird et al., 1988, "Single-chain antigen-binding proteins," Science, 242:423-426.

Brocks et al., 1997, "A TNF receptor antagonistic scFv, which is not secreted in mammalian cells, is expressed as a soluble mono- and bivalent scFv derivative in insect cells," Immunotechnology, 3:173-84.

Cai et al., 1995, "Anti-melanoma antibodies from melanoma patients immunized with genetically modified autologous tumor cells: selection of specific antibodies from single-chain Fv fusion phage libraries," Proceedings of the National Academy of Sciences of the United States of America, 92:6537-41.

Ghetie et al., 1997, "Homodimerization of tumor-reactive monoclonal antibodies markedly increases their ability to induce growth arrest or apoptosis of tumor cells," Proceedings of the National Academy of Sciences of the United States of America, 94:7509-14.

Huston et al., 1988, "Protein engineering of antibody binding sites: recovery of specific activity in an anti-digoxin single-chain Fv analogue produced in *Escherichia coli*," Proceedings of the National Academy of Sciences of the United States of America, 85:5879-83.

Kato et al., 1995, "Mammalian expression of single chain variable region fragments dimerized by Fc regions," Molecular Biology Reports, 21:141-146.

Laemmli, U.K., 1970, "Cleavage of structural proteins during the assembly of the head of bacteriophage T4," Nature, 227:680-85.

Lu et al., 1999, "An alternating selection strategy for cloning phage display antibodies," Journal of Immunological Methods, 228:109-119.

Michael et al., 1996, "In vitro and in vivo characterisation of a recombinant carboxypeptidase G2::anti-CEA scFv fusion protein," Immunotechnology, 2: 47-57.

Modak et al., 2001, "Monoclonal antibody 8H9 targets a novel cell surface antigen expressed by a wide spectrum of human solid tumors," Cancer Research, 61:4048-4054.

Powers et al., 2001, "Expression of single-chain Fv-Fc fusions in pinchia pastoris," Journal of Immunological Methods, 251:123-135.

Raag et al., 1995, "Single-chain Fvs," FASEB Journal, 9:73-80.

Schultz et al., 2000, "A tetravalent single-chain antibody-streptavidin fusion protein for pretargeted lymphoma therapy," Cancer Research, 60:6663-6669.

Shu et al., 1993, "Secretion of a single-gene-encoded immunoglobulin from myeloma cells," Proceedings of the National Academy of Sciences of the United States of America, 90:7995-9.

Thanavala et al., 1986, "A surrogate hepatitis B virus antigenic epitope represented by a synthetic peptide and an internal image antiidiotype antibody," Journal of Experimental Medicine, 164:227-236.

Towbin et al., 1979, "Electrophoretic transfer of proteins from polyacrylamide gels to nitrocellulose sheets: procedure and some applications," Proceedings of the National Academy of Sciences of the United States of America, 76:4350-4.

Tur et al., 2001, "Selection of scFv phages on intact cells under low pH conditions leads to a significant loss of insert-free phages," Biotechniques, 30:404-413.

Umana et al., 1999, "Engineered glycoforms of an antineuroblastoma IgG1 with optimized antibody-dependent cellular cytotoxic activity," Nature Biotechnology, 17: 176-180.

Wagner at al., 1997, "Immunological responses to the tumor-associated antigen CA125 in patients with advanced ovarian cancer induced by the murine monoclonal anti-idiotype vaccine ACA125," Hybridoma, 16:33-40.

Wang et al., 1999, "Human single-chain Fv immunoconjugates targeted to a melanoma-associated chondroitin sulfate proteoglycan mediate specific lysis of human melanoma cells by natural killer cells and complement," Proceedings of the National Academy of Sciences of the United States of America, 96:1627-32.

Watters et al., 1997, "An optimized method for cell-based phage display panning," Immunotechnology, 3:21-9.

Winter et al., 1991, "Man-made antibodies," Nature, 349:293-299.

Wright et al., 1997, "Effect of glycosylation on antibody function: implications for genetic engineering," Trends in Biotechnology, 15:26-31.

Wu et al., 1996, "Tumor localization of anti-CEA single-chain Fvs: improved targeting by non-covalent dimers," Immunotechnology, 2:21-36.

Stancovski et al., 1993, "Targeting of T lymphocytes to Neu/HERe-expressing cells using chimeric single chain Fv receptors," J. Immunol., 151:6577-6582.

Moritz et al., 1994, "Cytotoxic T lymphocytes with a grafted recognition specificity for ERBB2-expressing tumor cells," Proc. Natl. Acad. Sci. USA, 91:4318-4322.

Wels et al., 1995, "Biotechnological and gene therapeutic strategies in cancer treatment," Gene, 159: 73-80.

Eshhar et al., 2001, "Functional expression of chimeric receptor genes in human T cells," J. Immunol. Methods, 248:67-76.

Wei et al., 1994, "Experimental tumor therapy in mice using the cyclophosphamide-activating cytochrome P450 2B1 gene," Hum. Gene Ther., 5:969.

Weijtens et al., 1996, "Single chain Ig/gamma gene-redirected human T lymphocytes produce cytokines, specifically lyse tumor cells, and recycle lytic capacity," J. Immunol, 157:836-643.

Finney et al., 1998, "Chimeric receptors providing both primary and costimulatory signaling in T cells from a single gene product," J. Immunol, 161:2791-2797.

Koehne et al., 2000, "Rapid selection of antigen-specific T lymphocytes by retroviral transduction," Blood, 96:109-117.

Bunnell et al., 1995, "High-efficiency retroviral-mediated gene transfer into human nonhuman primate peripheral blood lymphocytes," Proceeds of the National Academy of Science USA, 92:7739-7743.

Miller et al., 1991, "Construction and properties of retrovirus packaging cells based on gibbon ape leukemia virus," J. Virol., 1991:2220-2224.

Lam et al., 1996, "Improved gene transfer into human lymphocytes using retroviruses with gibbon ape leukemia virus envelope," Hum. Gene Ther., 7:1415-1422.

Bonini et al., 1997, "HSV-TK gene transfer into donor lymphocytes for control of allogeneic graft-versus-leukemia," Science, 276:1719-1723.

Pollok et al., "High-efficiency gene transfer into normal and adenosine deaminase-deficient T lymphocytes is mediated by transduction on recombinant fibronectin fragments," J. Virol., 72.4882-4892, 1998.

Galea-Lauri et al., 1999, "Expression of a variant of CD28 on a subpopulation of human NK cells: implications for B7-mediated stimulation of NK cells," J. Immunol., 163:62-70.

Patel et al., 1999, "Impact of chimeric immune receptor extracellular protein domains on T cell function," Gene Therapy, 6:412-419.

Fitzer-Attas et al., 1998, "Harnessing Syk familytyrosine kinases as signaling domains for chimeric single chain of the variable domain receptors: optional design for T cell activation," J. Immunol., 160:146-154.

Alvarez-Vallina et al., 1999, "Efficient discrimination between different densities of target antigen by tetracycline-regulatable T bodies," Hum. Gene Ther., 10: 559-563.

Yee et al., 2001, "In vivo tracking of tumor-specific T cells," Curr. Opin. Immunol., 13:141-146.

Xiaoning et al., 1999, "Rapid death of adoptively transferred T cells in acquired immunodeficiency syndrome," Blood, 93:1506-1510.

Riddell et al., 1996, "T-cell mediated rejection of gene-modified HIV-specific cytotoxic T lymphocytes in HIV-infected patients," Nat. Med., 2:216-223.

Crist et al., 1995, "The Third Intergroup Rhabdomyosarcoma Study," J. Clin. Oncol., 13:610-30.

Maurer et al., 1993, "The Intergroup Rhabdomyosarcoma Study-II," Cancer, 71:1904-22.

Weigel et al., 2001, "Role of high-dose chemotherapy with hematopoietic stem cell rescue in the treatment of metastatic or recurrent rhabdomyosarcoma," J Pediatr Hematol. Oncol., 23:272-276.

Kramer et al., 2000, "Targeted radioimmunotherapy for leptomeningeal cancer using (131)I-3F8," Med. Pediatr. Oncol., 35:716-8.

Kumar et al., 2000, "Myogenin is a specific marker for rhabdomyosarcoma: an immunohistochemical study in paraffin embedded tissues," Mod. Pathol., 13:988-93.

Gattenloehner et al., 1998, "The fetal form of the acetylcholine receptor distinguishes rhabdomyosarcomas from other childhood tumors," Am. J. Pathol., 152:437-44.

Truong et al., 1990, "The diagnostic utility of desmin. A study of 584 cases and review of the literature," Am. J. Clin. Pathol., 93:305-14.

Qualman et al., 1998, "Intergroup Rhabdomyosarcoma Study: update for pathologists," Pediatr. Dev. Pathol., 1:550-61.

Strother et al., 1990, "Expression of the 5.1 H11 antigen, a fetal muscle surface antigen, in normal and neoplastic tissue," Arch. Pathol. Lab. Med., 114:593-596.

Merino et al., 2001, "Immunomagnetic purging of ewing's sarcoma from blood and bone marrow: quantitation by real-time polymerase chain reaction," J. Clin. Oncol., 19:3649-3659.

Supplementary European Search Report for EP 02 80 1782, filed Apr. 23, 2004, for Sloan-Kettering Institute for Cancer Research et al., dated Oct. 12, 2005.

PCT Notification of Transmittal of International Search Report, Apr. 2, 2002, for Sloan-Kettering Institute for Cancer Research, Int'l App'l No. PCT/US01/32565, filed Oct. 18, 2001.

Supplementary European Search Report, Oct. 14, 2005, for Sloan-Kettering Institute for Cancer Research, European App'l No. EP 03 71 6369, filed Oct. 8, 2004.

EPO Communication, Jan. 16, 2006, for Sloan-Kettering Institute for Cancer Research, European App'l No. EP 03 716 369.8, filed Oct. 8, 2004.

Modak et al., 1999, "Disialoganglioside GD2 and antigen 8H9: Potential targets for antibody-based immunotherapy against desmoplastic small round cell tumor (DSRCT) and rhabdomyosarcoma (RMS)," Proceedings of the American Association for Cancer Research Annual Meeting, 40:474.

U.S. Office Action, Dec. 27, 2007, for Nai-Kong V. Cheung, U.S. Appl. No. 10/097,558, filed Mar. 8, 2002.

U.S. Office Action, May 16, 2008, for Nai-Kong V. Cheung, U.S. Appl. No. 10/097,558, filed Mar. 8, 2002.

U.S. Notice of Allowance, Oct. 30, 2008, for Nai-Kong V. Cheung, U.S. Appl. No. 10/097,558, filed Mar. 8, 2002.

U.S. Office Action, Sep. 22, 2004, for Nai-Kong V. Cheung, U.S. Appl. No. 10/097,558, filed Mar. 8, 2002.

U.S. Office Action, Aug. 24, 2004, for Nai-Kong V. Cheung, U.S. Appl. No. 10/097,558, filed Mar. 8, 2002.

U.S. Office Actions, Both dated Dec. 13, 2006, for Nai-Kong V. Cheung, U.S. Appl. No. 10/505,658, filed Aug. 20, 2004.

U.S. Office Action, Jan. 17, 2007, for Nai-Kong V. Cheung, U.S. Appl. No. 10/505,658, filed Aug. 20, 2004.

U.S. Office Action, Apr. 2, 2007, for Nai-Kong V. Cheung, U.S. Appl. No. 10/505,658, filed Aug. 20, 2004.

U.S. Office Action, Mar. 20, 2008, for Nai-Kong V. Cheung, U.S. Appl. No. 10/505,658, filed Aug. 20, 2004.

U.S. Office Action, Sep. 24, 2008, for Nai-Kong V. Cheung, U.S. Appl. No. 10/505,658, filed Aug. 20, 2004.

U.S. Office Action, Mar. 2, 2009, for Nai-Kong V. Cheung, U.S. Appl. No. 10/505,658, filed Aug. 20, 2004.

Li et al, 2000, "Single-chain antibodies against human insulin-like growth factor I receptor: expression, purification, and effect on tumor growth",Cancer Immunol. Immunotherapy, 49:243-252.

European Office Action, Jan. 26, 2007, for Sloan-Kettering Institute for Cancer Research, European Application No. 02801782.

PCT Notification Concerning Transmittal of International Preliminary Report on Patentability for Sloan-Kettering Institute for Cancer Research et al., Sep. 22, 2009, Int'l Application No. PCT/US2008/058030.

U.S. Notice of Allowance, Sep. 23, 2009, for Nai-Kong V. Cheung, U.S. Appl. No. 10/097,558, filed Mar. 8, 2002.

U.S. Office Action, Feb. 20, 2009, for Nai-Kong V. Cheung and Hong-fen Guo, U.S. Appl. No. 10/273,762, filed Oct. 17, 2002.

Kawai et al., 1999, "Occurrence of ganglioside GD3 in neoplastic astrocytes", Virchows Arch. 434:201-205.

U.S. Notice of Allowance, Sep. 25, 2009, for Nai-Kong V. Cheung, U.S. Appl. No. 10/273,762, filed Oct. 17, 2002.

U.S. Interview Summary, Aug. 11, 2009, for Nai-Kong V. Cheung, U.S. Appl. No. 10/273,762, filed Oct. 17, 2002.

U.S. Office Action, Jul. 10, 2007, for Nai-Kong V. Cheung, U.S. Appl. No. 10/273,762, filed Oct. 17, 2002.

U.S. Office Action, Jan. 14, 2008, for Nai-Kong V. Cheung, U.S. Appl. No. 10/273,762, filed Oct. 17, 2002.

U.S. Office Action, Nov. 17, 2005, for Nai-Kong V. Cheung, U.S. Appl. No. 10/273,762, filed Oct. 17, 2002.

U.S. Advisory Action, Dec. 13, 2006, for Nai-Kong V. Cheung, U.S. Appl. No. 10/273,762, filed Oct. 17, 2002.

U.S. Advisory Action, Jan. 22, 2007, for Nai-Kong V. Cheung, U.S. Appl. No. 10/273,762, filed Oct. 17, 2002.

U.S. Office Action, Sep. 15, 2008, for Nai-Kong V. Cheung, U.S. Appl. No. 10/273,762, filed Oct. 17, 2002.

Baxevanis et al., 2004, "Targeting of tumor cells by lymphocytes engineered to express chimeric receptor genes", Cancer Immunol Immunother, 53:893-903.

Gura, T., 1997, "Systems for identifying new drugs are often faulty", Science, 278:1041-1042.

Jain, R.K., 1994, "Barriers to drug delivery in solid tumors", Sci. Am., 271:58-65.

U.S. Office Action, Apr. 5, 2006, for Nai-Kong V. Cheung, U.S. Appl. No. 10/273,762, filed Oct. 17, 2002.

U.S. Office Action, Sep. 7, 2006, for Nai-Kong V. Cheung, U.S. Appl. No. 10/273,762, filed Oct. 17, 2002.

U.S. Office Action, Mar. 23, 2007, for Nai-Kong V. Cheung, U.S. Appl. No. 10/273,762, filed Oct. 17, 2002.

European Office Action, Jul. 1, 2010, for Sloan-Kettering Institute for Cancer Research, for EP 01 98 3999 , Filed May 16, 2003, National Stage of PCT/US01/32565, filed Oct. 18, 2001.

European Communication under Rule 71(3) EPC, Apr. 28, 2010, for Sloan-Kettering Institute for Cancer Research, for for EP 03 716 369.8, Filed Oct. 18, 2004, National Stage of PCT/US03/07004, Filed Mar. 6, 2003.

Supplemental European Search Report for EP 08 744 263.8, filed Sep. 1, 2009, for Sloan-Kettering Institute for Cancer Research et al., dated Mar. 1, 2010.

U.S. Notice of Allowance, Dec. 14, 2009, for Nai-Kong V. Cheung, U.S. Appl. No. 10/505,658, filed Aug. 20, 2004.

Canadian Office Action, Nov. 2, 2009, for Sloan-Kettering Institute for Cancer Research, Canadian Application No. 2,463,017, Filed Apr. 14, 2004, National Stage of PCT/US02/33331, Filed Oct. 17, 2002.

European Result of Consultation, Mar. 12, 2010, for Sloan-Kettering Institute for Cancer Research, for for EP 03 716 369.8, Filed Oct. 18, 2004, National Stage of PCT/US03/07004, Filed Mar. 6, 2003.

U.S. Notice of Allowance, Aug. 21, 2009, for Nal-Kong V. Cheung, U.S. Appl. No. 10/505,658, filed Aug. 20, 2004.

Canadian Office Action, Feb. 3, 2011, for Sloan-Kettering Institute for Cancer Research, Canadian Application No. 2,463,017, Filed Apr. 14, 2004, National Stage of PCT/US02/33331, Filed Oct. 17, 2002.

\* cited by examiner

1A

1C

1B

Thymidine

FIAU

```
                       SEQUENCE LISTING

<160> NUMBER OF SEQ ID NOS: 18

<210> SEQ ID NO 1
<211> LENGTH: 33
<212> TYPE: DNA
<213> ORGANISM: Homo sapiens
<220> FEATURE:
<221> NAME/KEY: misc_feature
<222> LOCATION: (1)..(33)
<223> OTHER INFORMATION: hCD8a leader - scFv -CD28      Sense Primer
      (Hpa I - Human CD8a Leader)

<400> SEQUENCE: 1
ttattacgag ttaacatggc cttaccagtg acc                              33

<210> SEQ ID NO 2
<211> LENGTH: 32
<212> TYPE: DNA
<213> ORGANISM: Homo sapiens
<220> FEATURE:
<221> NAME/KEY: misc_feature
<222> LOCATION: (1)..(32)
<223> OTHER INFORMATION: hCD8a leader - scFv - CDD28    Antisense
      Primer (Xho I - Human CD28)

<400> SEQUENCE: 2
cttggtctcg agtgtcagga gcgataggct gc                               32

<210> SEQ ID NO 3
<211> LENGTH: 31
<212> TYPE: DNA
<213> ORGANISM: Homo sapiens
```

```
<220> FEATURE:
<221> NAME/KEY: misc_feature
<222> LOCATION: (1)..(31)
<223> OTHER INFORMATION: 8H9scFvSense Primer (Cla I - 8H9 heavy chain)

<400> SEQUENCE: 3
ttattacgaa tcgattgccc aggtcaaact g                                   31

<210> SEQ ID NO 4
<211> LENGTH: 29
<212> TYPE: DNA
<213> ORGANISM: Homo sapiens
<220> FEATURE:
<221> NAME/KEY: misc_feature
<222> LOCATION: (1)..(29)
<223> OTHER INFORMATION: 8H9scFvAntisense Primer (Not I - 8H9 light
      chain)

<400> SEQUENCE: 4
cttggtgcgg ccgcctgttt cagctccag                                      29

<210> SEQ ID NO 5
<211> LENGTH: 30
<212> TYPE: DNA
<213> ORGANISM: Homo sapiens
<220> FEATURE:
<221> NAME/KEY: misc_feature
<222> LOCATION: (1)..(30)
<223> OTHER INFORMATION: 5F11scFvSense Primer (Cla I - 5F11 heavy chain)

<400> SEQUENCE: 5
ttattacgaa tcgattcagc agtcaggacc                                     30

<210> SEQ ID NO 6
<211> LENGTH: 32
<212> TYPE: DNA
<213> ORGANISM: Homo sapiens
<220> FEATURE:
<221> NAME/KEY: misc_feature
<222> LOCATION: (1)..(32)
<223> OTHER INFORMATION: 5FFF11scFvAntisense Primer (Not I - 5F11 light
      chain)

<400> SEQUENCE: 6
cttggtgcgg ccgcccgttt tatttccaac tg                                  32

<210> SEQ ID NO 7
<211> LENGTH: 48
<212> TYPE: DNA
<213> ORGANISM: Homo sapiens
<220> FEATURE:
<221> NAME/KEY: misc_feature
<222> LOCATION: (1)..(48)
<223> OTHER INFORMATION: hTCR-? chain       Sense Primer (Bst U I - CD28
      end -Xho I - hTCR-? [cytoplasmic domain])

<400> SEQUENCE: 7
cgcgacttag cagcctatcg ctcctggcac tcgagaagag tgaagttc                 48

<210> SEQ ID NO 8
<211> LENGTH: 30
<212> TYPE: DNA
<213> ORGANISM: Homo sapiens
<220> FEATURE:
<221> NAME/KEY: misc_feature
<222> LOCATION: (1)..(30)
<223> OTHER INFORMATION: hTCR-? chainAntisense Primer (BglII - hTCR z)

<400> SEQUENCE: 8
```

-continued cttggtagat cttcagcgag ggggcagggc                                30

<210> SEQ ID NO 9
<211> LENGTH: 23
<212> TYPE: DNA
<213> ORGANISM: Homo sapiens
<220> FEATURE:
<221> NAME/KEY: misc_feature
<222> LOCATION: (1)..(23)
<223> OTHER INFORMATION: 8H9scFvsense primer

<400> SEQUENCE: 9
caaatatgct tcccaatcca tct                                       23

<210> SEQ ID NO 10
<211> LENGTH: 25
<212> TYPE: DNA
<213> ORGANISM: Homo sapiens
<220> FEATURE:
<221> NAME/KEY: misc_feature
<222> LOCATION: (1)..(25)
<223> OTHER INFORMATION: 8H9scFvantisense primer

<400> SEQUENCE: 10
actgagagtg aaatctgacc ctgat                                     25

<210> SEQ ID NO 11
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: 8H9scFvProbe

<400> SEQUENCE: 11
tcccctccag gttcagtggc agtg                                      24

<210> SEQ ID NO 12
<211> LENGTH: 25
<212> TYPE: DNA
<213> ORGANISM: Homo sapiens
<220> FEATURE:
<221> NAME/KEY: misc_feature
<222> LOCATION: (1)..(25)
<223> OTHER INFORMATION: B-actinsense primer

<400> SEQUENCE: 12
tcacccacac tgtgcccatc tacga                                     25

<210> SEQ ID NO 13
<211> LENGTH: 25
<212> TYPE: DNA
<213> ORGANISM: Homo sapiens
<220> FEATURE:
<221> NAME/KEY: misc_feature
<222> LOCATION: (1)..(25)
<223> OTHER INFORMATION: B-actinantisense primer

<400> SEQUENCE: 13
cagcggaccc gctcattgcc aatgg                                     25

<210> SEQ ID NO 14
<211> LENGTH: 30
<212> TYPE: DNA
<213> ORGANISM: Homo sapiens
<220> FEATURE:
<221> NAME/KEY: misc_feature
<222> LOCATION: (1)..(30)

```
<223> OTHER INFORMATION: B-actinProbe

<400> SEQUENCE: 14
atgccctamr accccatgc catcctgcgt                                    30

<210> SEQ ID NO 15
<211> LENGTH: 19
<212> TYPE: DNA
<213> ORGANISM: Homo sapiens
<220> FEATURE:
<221> NAME/KEY: misc_feature
<222> LOCATION: (1)..(19)
<223> OTHER INFORMATION: GAPDHsense primer

<400> SEQUENCE: 15
gaaggtgaag gtcggagtc                                               19

<210> SEQ ID NO 16
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: GAPDHantisense primer

<400> SEQUENCE: 16
gaagatggtg atgggatttc                                              20

<210> SEQ ID NO 17
<211> LENGTH: 20
<212> TYPE: DNA
<213> ORGANISM: Homo sapiens
<220> FEATURE:
<221> NAME/KEY: misc_feature
<222> LOCATION: (1)..(20)
<223> OTHER INFORMATION: GAPDHProbe

<400> SEQUENCE: 17
caagcttccc gttctcagcc                                              20

<210> SEQ ID NO 18
<211> LENGTH: 11
<212> TYPE: PRT
<213> ORGANISM: Artificial Sequence
<220> FEATURE:
<223> OTHER INFORMATION: Synthetic

<400> SEQUENCE: 18

Gly Ala Pro Val Pro Asp Pro Leu Glu Pro Arg
1               5                   10
```

METHOD FOR PREPARATION OF SINGLE CHAIN ANTIBODIES

This application is a Divisional Application of U.S. Ser. No. 10/273,762, filed Oct. 17, 2002, which claims priority of U.S. Ser. No. 60/330,396, filed 17 Oct. 2001; Int'l App'l No. PCT/US01/32565, Filed 18 Oct. 2001; and U.S. Ser. No. 10/097,558, Filed 8 Mar. 2002, the content of which is incorporated by reference here into this application.

This application was supported in part by Department Of Energy Grant No. DE-FG-02-93ER61658, National Institute of Health Grant No. CA61017 and National Cancer Institute Grant No. NCICA 89936. Accordingly, the United States Government may have certain rights in this invention.

Throughout this invention, various references are referred to. Disclosures of these publications in their entireties are hereby incorporated by reference into this application to more fully describe the state of the art to which this invention pertains.

BACKGROUND OF THE INVENTION

This invention relates to a method for preparation of single chain antibodies, and is of particular applicability to preparation of single chain Fv antibody fragments (scFv) where the antigen to which the antibody binds is difficult to purify.

ScFv are antibody constructs comprising the variable regions of the heavy and light chains of an antibody as a single chain Fv fragment. ScFv technology utilizes molecular biology methods to reduce antibodies to the minimal-required-unit of heavy and light chain variable regions tethered by a peptide linker which can be designed with versatile side chains for radioconjugation.

Procedures for making scFv are known in the art. These procedures generally involve amplification of gene regions encoding the variable regions of the antibodies, assembly of an scFv genetic sequence and expression of the scFv genetic sequence in host cells. The host cells are screened using a target antigen to identify those cells which bind to the antigen, ands thus which express a functional scFv of the desired specificity. While this procedure works well in many cases, it requires the isolation of the antigen for use as a screening tool. In some cases, however, particularly in the case of membrane bound receptor molecules, this isolation may be difficult, or the conformation of the isolated antigen may be so different that it fails to present the same epitopes for binding. In these cases, the conventional techniques for development of an scFv are either unworkable or very difficult.

SUMMARY OF THE INVENTION

This invention provides a method for identifying cells expressing a target single chain antibody (scFv) directed against a target antigen from a collection of cells that includes cells that do not express the target scFv, comprising the step of combining the collection of cells with an anti-idiotype directed to an antibody specific for the target antigen and detecting interaction, if any, of the anti-idiotype with the cells, wherein the occurrence of an interaction identifies the cell as one which expresses the target scFv.

This invention also provides a method for inducing proliferation in a population of T cells comprising the steps of (a) introducing to the T cells an expressable gene sequence encoding a scFv coupled to a transmembrane and signaling domain; and (b) exposing the T cells to which the chimeric scFv has been introduced to an anti-idiotype directed to an antibody specific for a target antigen to which the scFv is directed under conditions such that the anti-idiotype will bind to scFv on the surface of cells expressing the chimeric scFv thereby inducing proliferation of the T cells.

This invention further provides a method for treating cancer in a patient suffering from cancer expressing an antigenic marker comprising the steps of removing lymphocytes from the patient, introducing to the lymphocytes an expressable gene sequence encoding a chimeric scFv coupled to a transmembrane and signaling domain; exposing the lymphocytes to which the chimeric scFv has been introduced to an anti-idiotype directed to an antibody specific for a target antigen to which the scFv is directed under conditions such that the anti-idiotype will bind to scFv on the surface of cells expressing the chimeric scFv and any necessary co stimulatory molecules to induce proliferation of the lymphocytes; and returning the expanded population of lymphocytes to the patient.

In addition, this invention provides a method for treating cancer in a patient suffering from cancer expressing an antigenic marker comprising the steps of introducing to human cell lines an expressable gene sequence encoding a chimeric scFv coupled to a transmembrane and signaling domain (including zeta chain); exposing the lymphocytes to which the chimeric scFv has been introduced to an anti-idiotype directed to an antibody specific for a target antigen to which the scFv is directed under conditions such that the anti-idiotype will bind to scFv on the surface of cells expressing the chimeric scFv and any necessary co stimulatory molecules to immunoselect and stimulate clones with high density of scFv expression and efficient tumor cytotoxicity to produce a gene-modified cell line, and returning the expanded population of gene-modified cell line to the patient.

This invention also provides a method for enhancing in vivo survival and anti-tumor activity of infused lymphocytes gene-modified with scFv-Chimeric immune receptors by intravenous injection of anti-idiotype antibody. This invention further provides compositions containing scFv, scFv fusion, cells identified, induced T cell population, alone or in combination thereof.

Finally, this invention provides various uses of the above methods and compositions.

DETAILED DESCRIPTION OF THE FIGURES

First Series of Experiments

FIG. 1. Inhibition of 8H9 by anti-idiotype 2E9 by FACS analysis. 1A: Staining of LAN-1 neuroblastoma cells with 5 ug/ml of 8H9 (shaded peak) was not inhibited at low concentration of 2E9 (2 ug/ml, black solid line), but almost completely at concentration of 10 ug/ml (dotted line) superimposable with the negative antibody control (grey solid line). 1B: Staining of LAN-1 neuroblastoma cells with 5 ug/ml of 3F8 (anti-GD2, shaded peak) was not inhibited by any concentrations (2 ug/ml, black solid line, or 200 ug/ml, dotted line) of 2E9; negative antibody control thin solid line. 1C: Staining of HTB-82 rhabdomyosarcoma cells with 5 ug/ml of 8H9 (grey peak) was not inhibited at low concentration (2 ug/ml, grey solid line), but completely at 10 ug/ml of 2E9 (black solid line) superimposable with negative antibody control (black peak).

Figure 2:
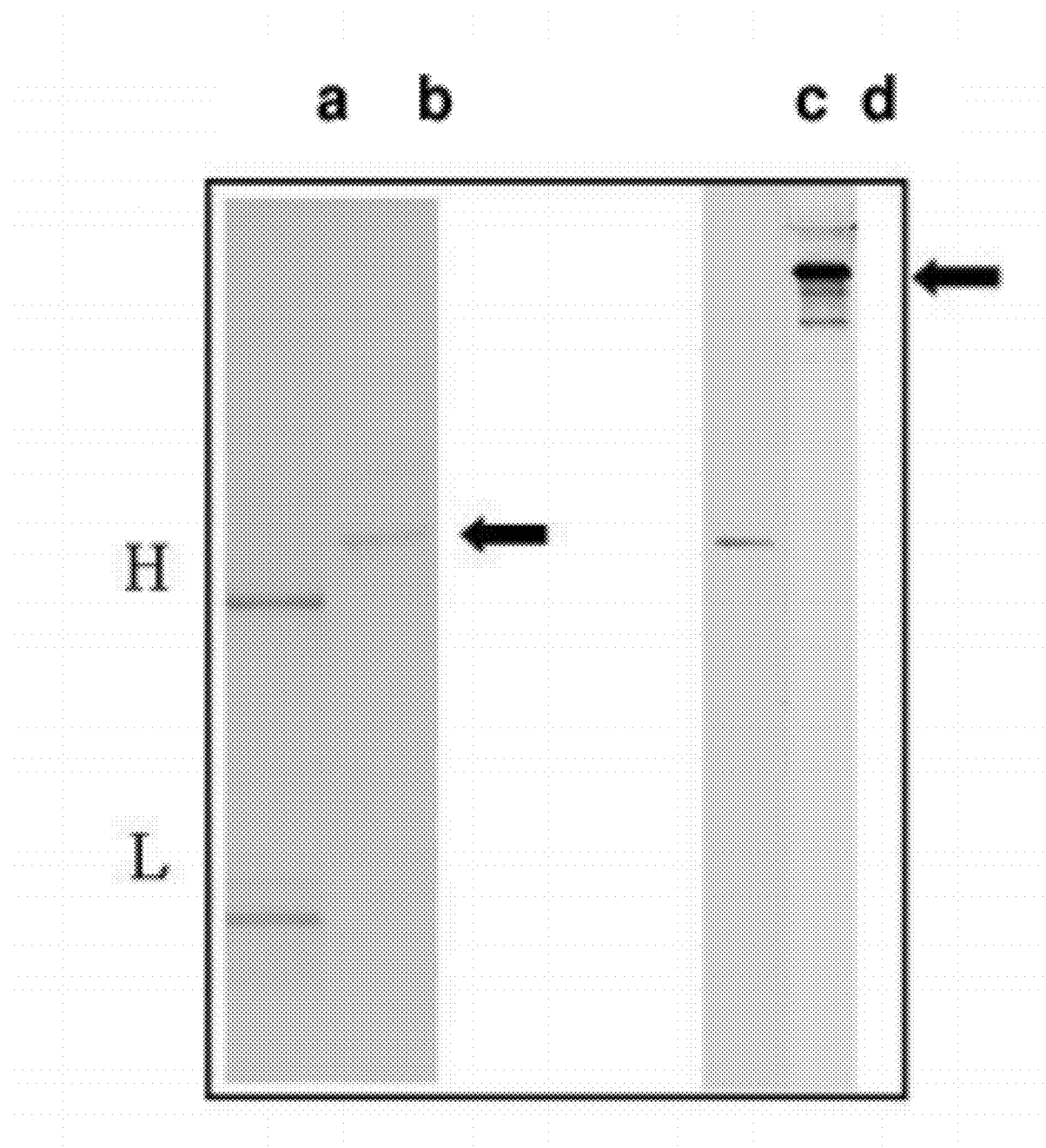

FIG. 2. SDS-PAGE (lanes a and b) and Western blot (c and d) of ch8H9. H=heavy chain of 8H9, L=light chain of 8H9, arrow points to ch8H9, the fusion protein between 8H9 scFv and the human 1-CH2-CH3 domain. With 2-mercaptothanol: lanes a, b and c. Native gel: lane d. SDS-PAGE was stained with Comassie Blue; western blot with 2E9 anti-idiotypic antibody.

Figure 3:
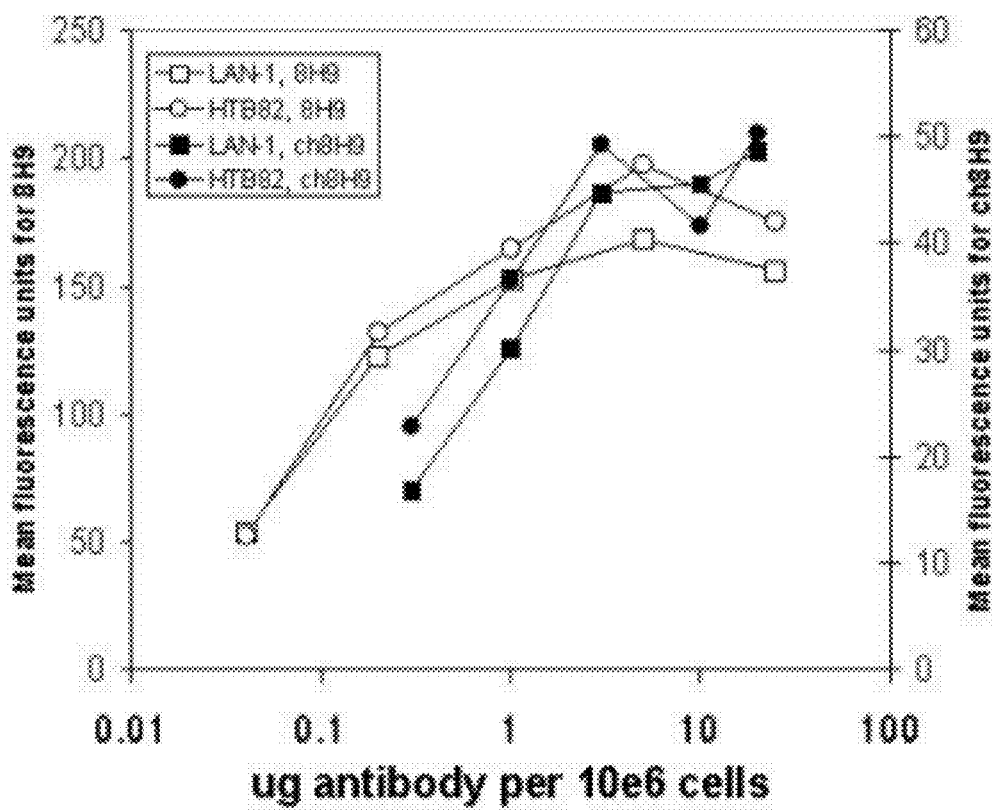

FIG. 3. FACS analysis of ch8H9 and 8H9 staining of HTB82 rhabdomyosarcoma and LAN-1 neuroblastoma cells. Mean immunofluorescence increased with concentrations of ch8H9 and 8H9, reaching a plateau around antibody concentration of 3-5 ug/ml. Left Y-axis is mean fluorescence for native 8H9, and the right Y-axis depicts mean fluorescence for ch8H9. Stronger fluorescence for native 8H9 reflects a stronger second antibody.

Figure 4:
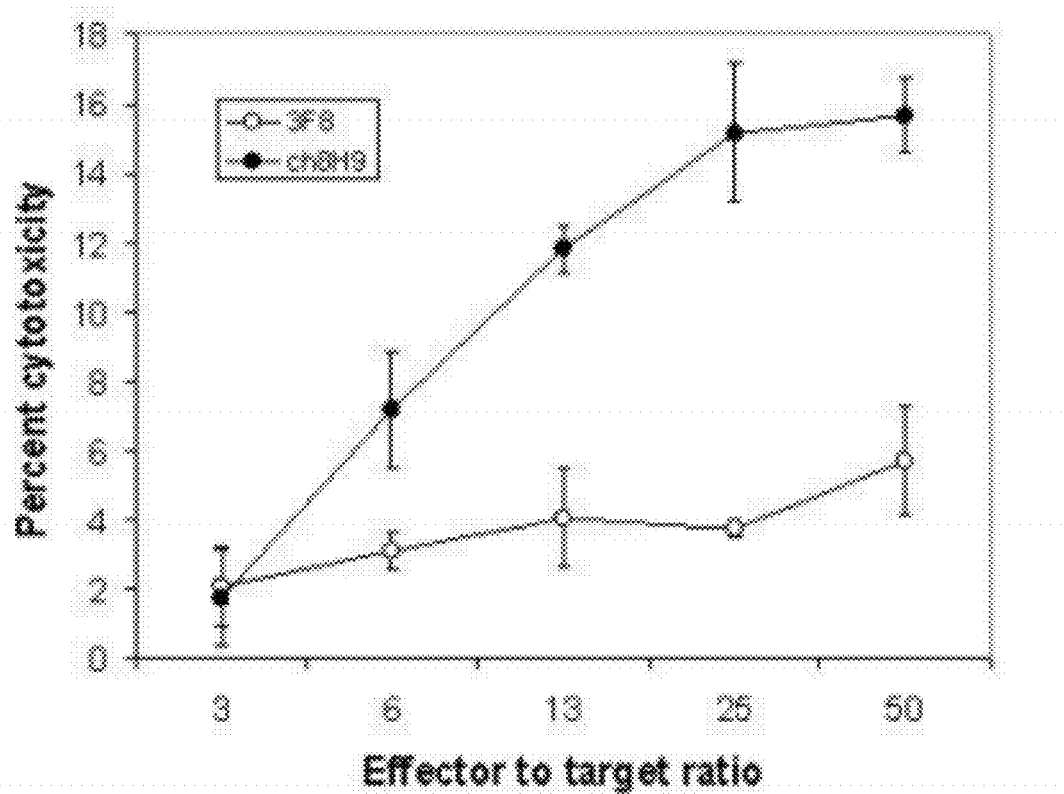

FIG. 4. ch8H9 in antibody-dependent cell-mediated cytotoxicity. ADCC was measured by $^{51}Cr$ release as described in Materials and Methods. Percent specific release is depicted as mean+/−SEM. Target cell line was rhabdomyosarcoma HTB-82. Control antibody was 3F8 which binds poorly to HTB-82.

Figure 5:
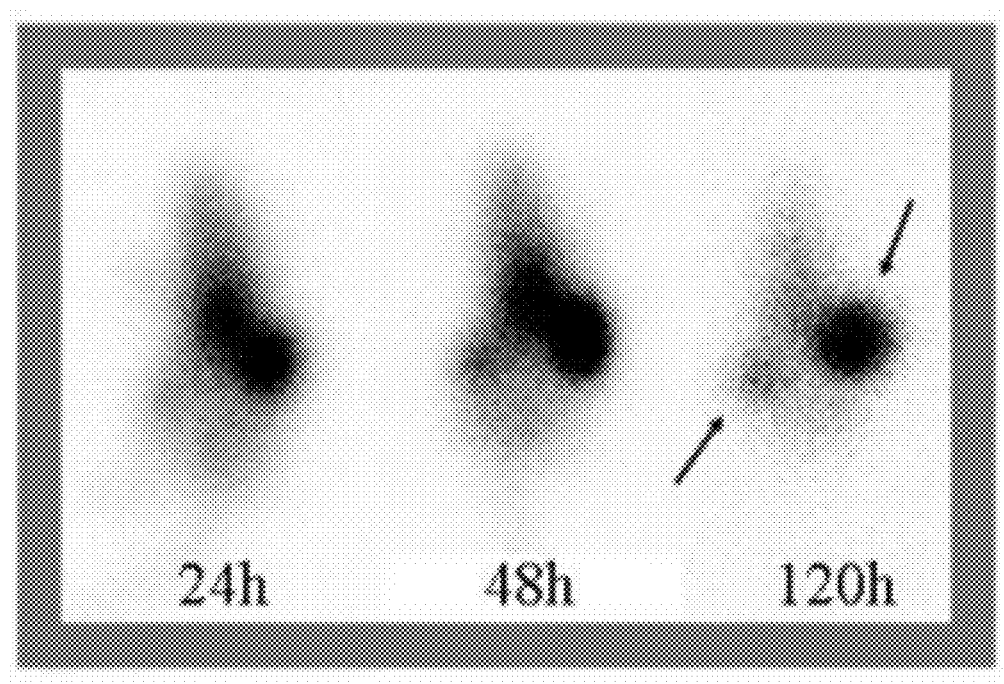

FIG. 5. Immunoscintigraphy of human tumors using $^{125}I$-labeled ch8H9. Mice xenografted with human LAN-1 neuroblastoma received retroorbital injections of 25 uCi of $^{125}I$-labeled antibody. 24 h, 48 h and 7 days after injection, the animals were anesthesized and imaged with a gamma camera.

Figure 6:
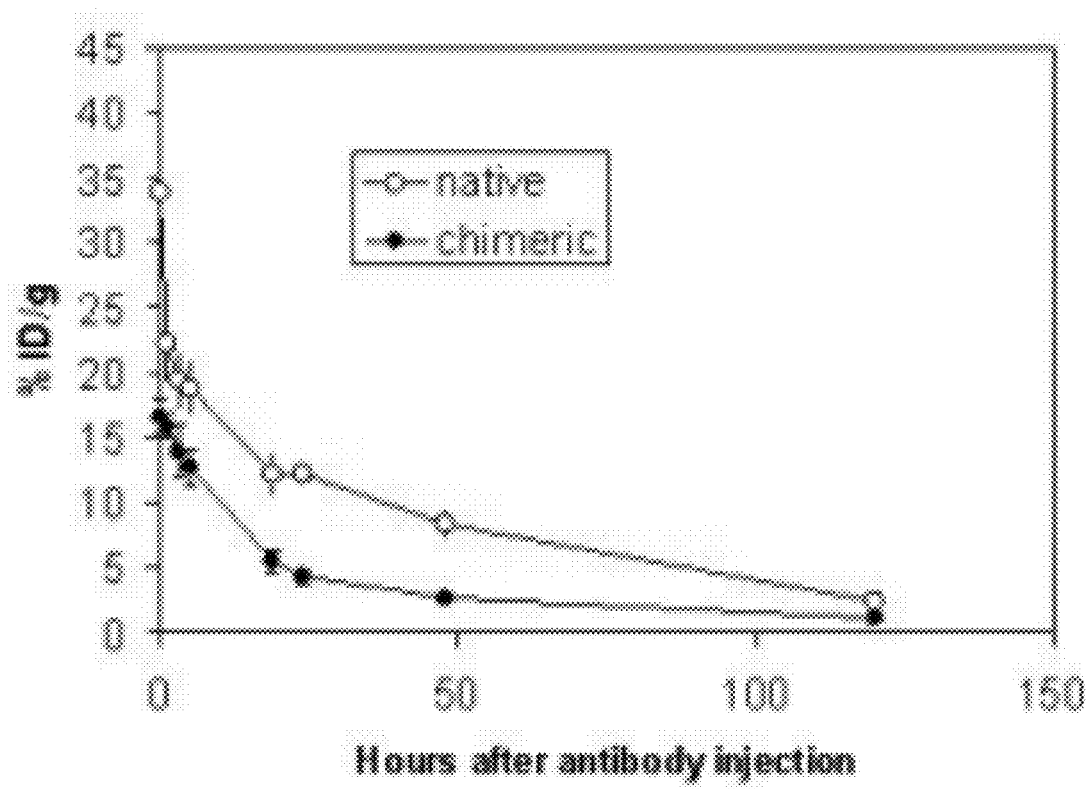

FIG. 6. Blood clearance of $^{125}I$-labeled ch8H9 and $^{125}I$-native 8H9. Mice xenografted with human LAN-1 neuroblastoma received retroorbital injections of $^{125}I$-labeled antibody. Percent injected dose/gm of serial blood samples were plotted over time.

Second Series of Experiments

Figure 7:
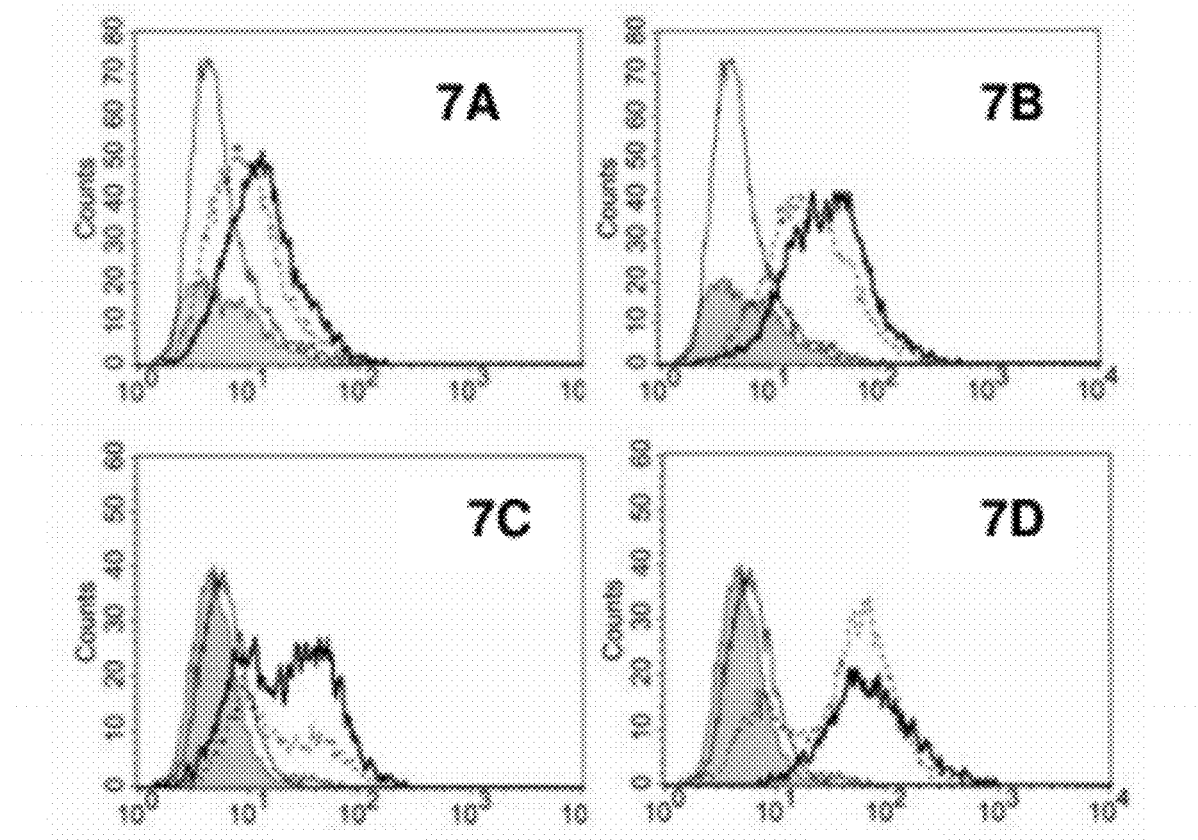

FIG. 7. Anti-idiotype affinity enrichment of producer lines. Producer lines were stained with anti-idiotypic MoAb 2E9 before (shaded peak, 7A and 7B), and after first (dotted line peak, 7A) and second (thick solid line, 7A) affinity purification, and after first (dotted line, 7B) and second (solid line 7B) subcloning, showing improved scFv expression. By FACS the indicator line K562 showed improved scFv expression after first (dotted line, 7C) and second (thick solid line, 7C) affinity purification of the producer line, and subsequent first (dotted line, 7C) and second (thick solid line, 7D) subcloning of the producer line, when compared to unpurified producer lines (shaded peaks, 7C and 7D), consistent with improvement in gene transduction efficiency. The thin solid line curves in each figure represents nonproducer line (7A and 7B) or uninfected K562 (7C and 7D).

Figure 8:
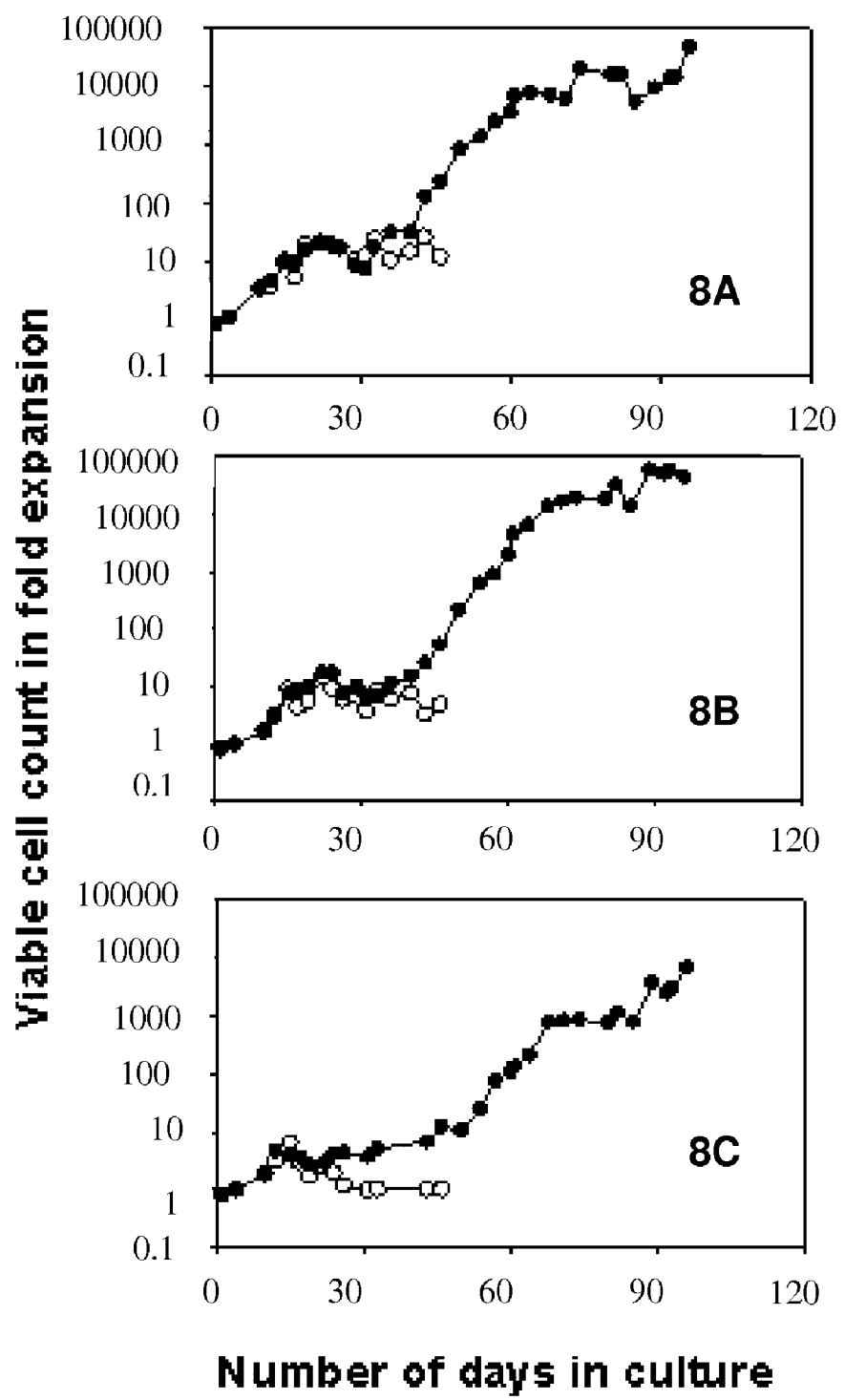

FIG. 8. In vitro expansion of 8h9-scfv-CD28-ζ gene-modified primary human lymphocytes depends on stimulation with anti-idiotypic antibody. Clonal expansion was expressed as fold expansion of initial viable lymphocyte number. Il-2 (100 u/ml [FIG. 8a], 50 u/ml [FIG. 8b] and 20 u/ml [FIG. 8c]) was added after retroviral infection and was present throughout the entire in vitro culture period, in the presence (solid circles) or absence (open circles) of solid-phase anti-idiotypic antibody. Viable cell count was performed using trypan blue assay.

Figure 9:
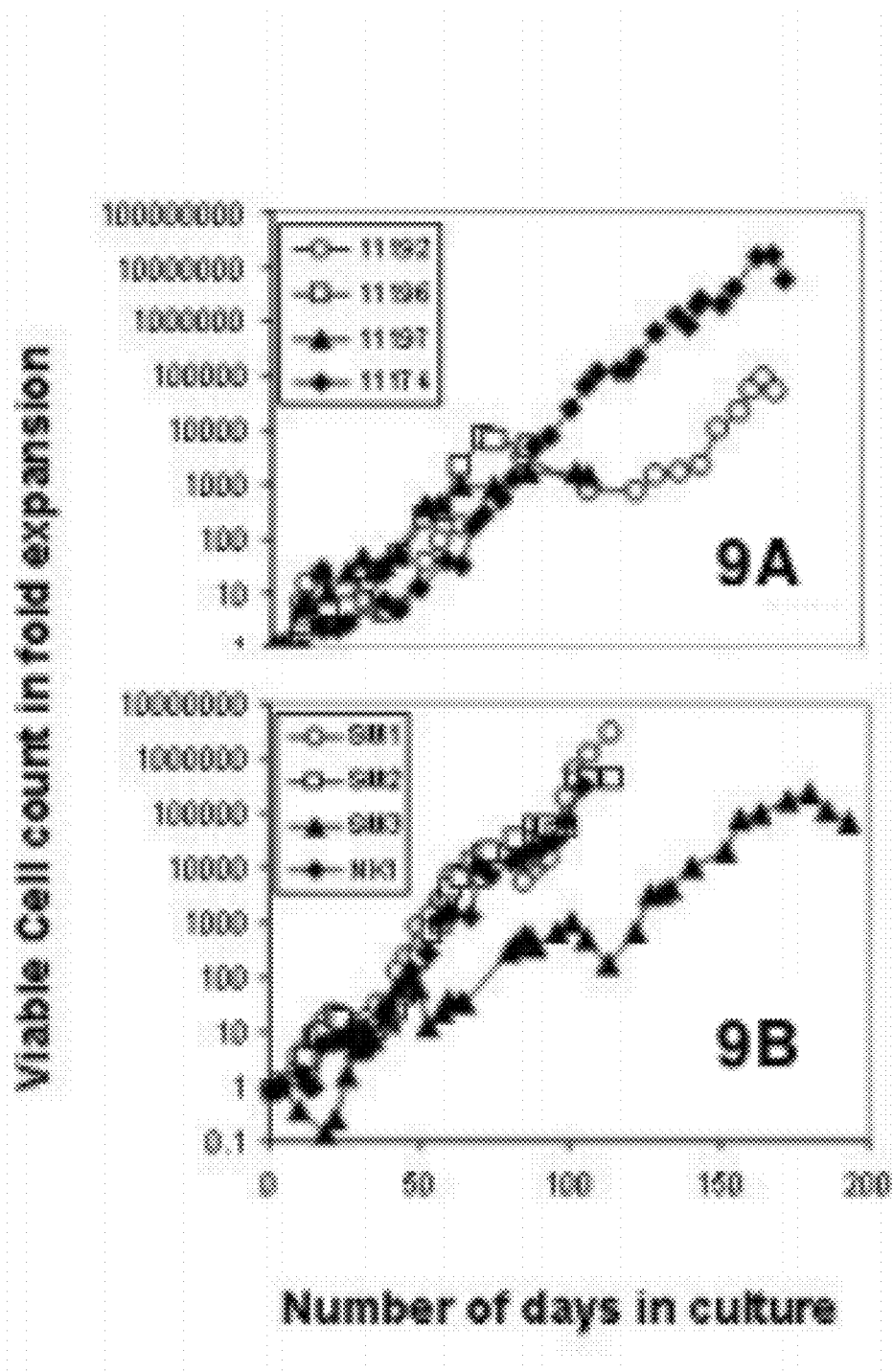

FIG. 9. In vitro expansion of 8H9-scFv-CD28-ζ gene-modified primary human lymphocytes from 4 patients with stage 4 neuroblastoma (FIG. 9A) and 4 samples from 2 normal volunteers (FIG. 9B). Clonal expansion was expressed as fold expansion of initial viable lymphocyte number before in vitro culture. IL-2 (100 U/ml) and anti-idiotype antibodies were present as described in Materials and Methods. 8H9-scFv-CD28-ζ gene-modified lymphocytes underwent continual clonal expansion (103 to 108), and survived 150-200 days in vitro, with a double time of ~5-10 days.

Figure 10:
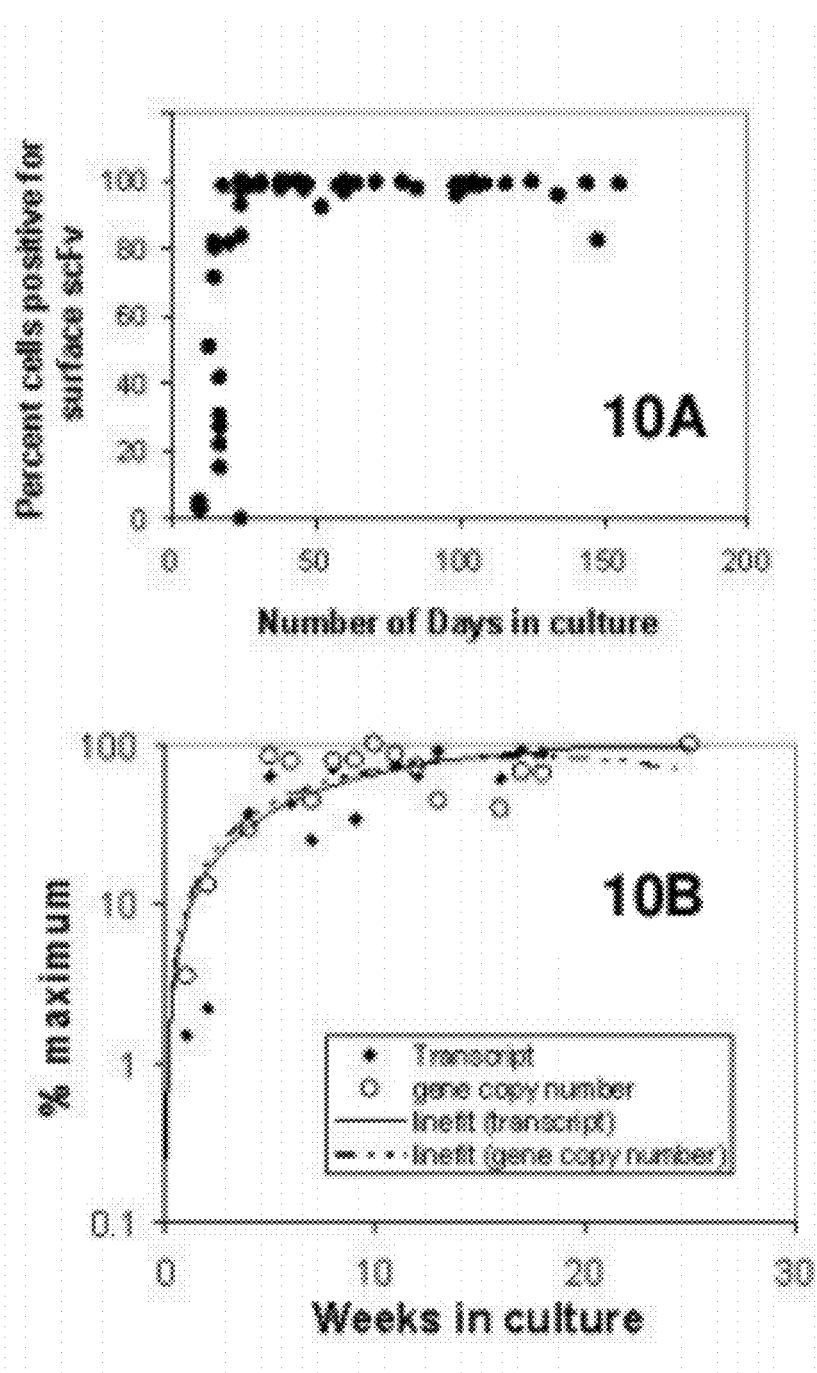

FIG. 10. Kinetics of clonal dominance by scFv+ cells and its relationship to 8H9scFv gene copy number and 8H9scFv transcript. Percent of lymphocytes positive for surface scFv was monitored by flow cytometry using anti-idiotype antibody (FIG. 10A); it rapidly increased to near 100% by 3 weeks of culture. ScFv gene copy number (PCR, open circles, broken line, FIG. 10B) and scFv transcript (RT-PCR, solid diamonds, solid line, FIG. 10B) also increased with time, reaching their plateau by 10 weeks in culture.

Figure 11:
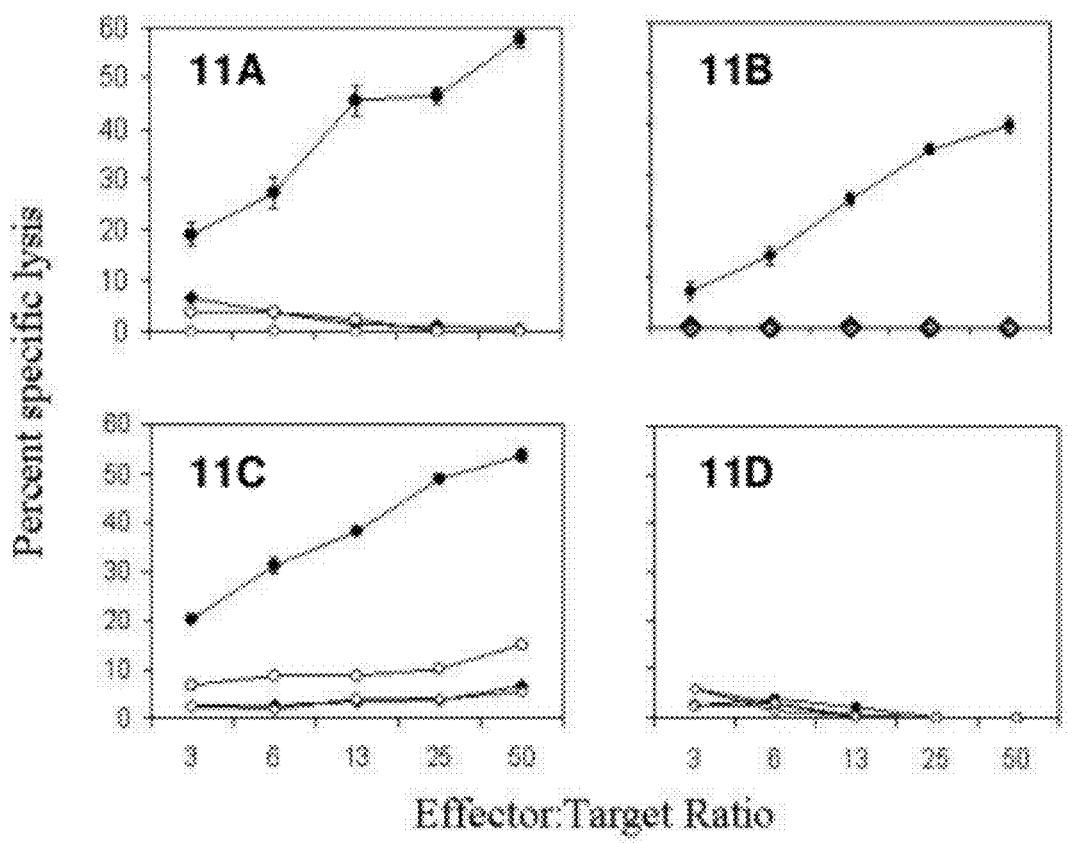

FIG. 11. Cytotoxicity against tumor cell lines: 8H9-scFv-CD28-ζ gene-modified lymphocytes (solid circles) from day of culture were assayed by 51Cr release assay in the presence or absence of MoAb 8H9 (50 ug/ml final concentration) as an antigen blocking agent (open circles). Control lymphocytes from the same donor but not gene-modified, were cultured under the same conditions as the gene-modified cells, and tested in cytotoxicity assays in the presence (open diamonds) or absence (solid diamonds) of MoAb 8H9. 11A: NMB-7 neuroblastoma. 11B: LAN-1 neuroblastoma. 11C: HTB-82 rhabdomyosarcoma. 11D: Daudi lymphoma.

Figure 12:
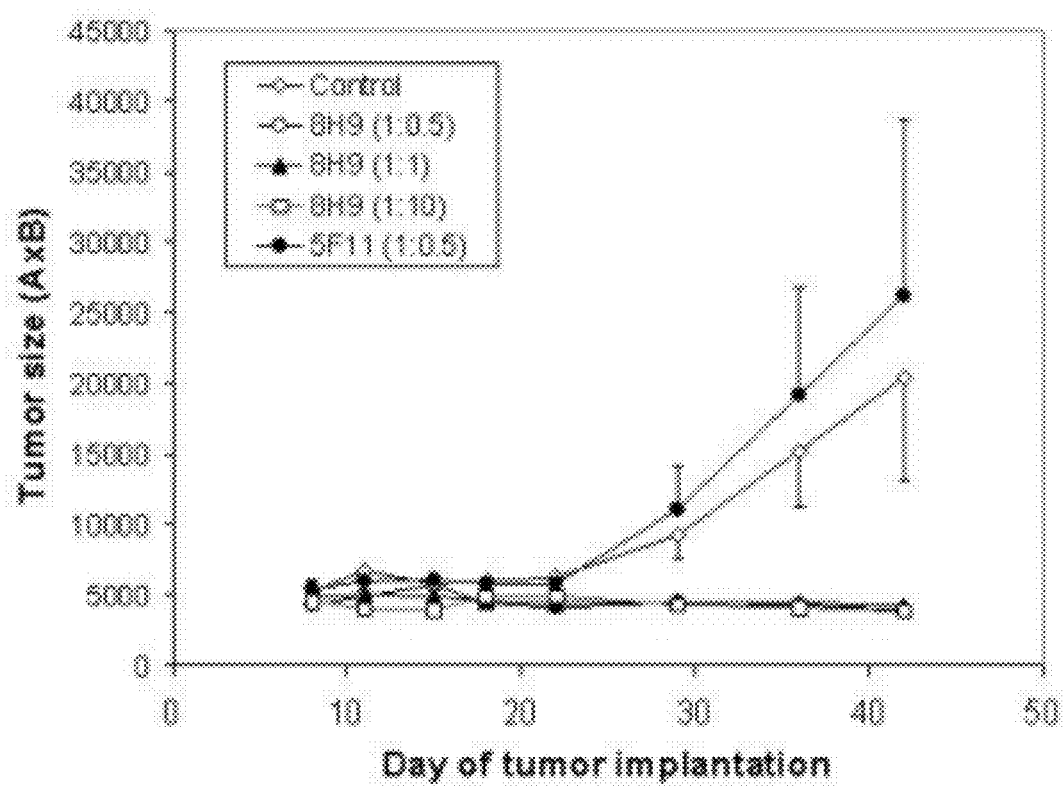

FIG. 12. Winn assay. Suppression of rhabdomyosarcoma tumor growth in scid mice. Human rhabdomyosarcoma HTB-82 was strongly reactive with 8H9, but not with 5F11 (anti-GD2) antibodies. Experimental groups: HTB-82 was mixed with 8H9-scfv-CD28-ζ gene-modified human lymphocytes at 3 ratios: 1:0.5 (open circle, n=5), 1:1 (solid triangle, n=5), 1:10 (open square, n=10). Control groups: no T-cell (open triangles, n=5), 5F11scfv-CD28-ζ modified lymphocytes at 1:0.5 ratio (solid circles, n=5). Tumor size was calculated as product of two perpendicular diameters a×b (mean±sem) and plotted over time.

Figure 13:
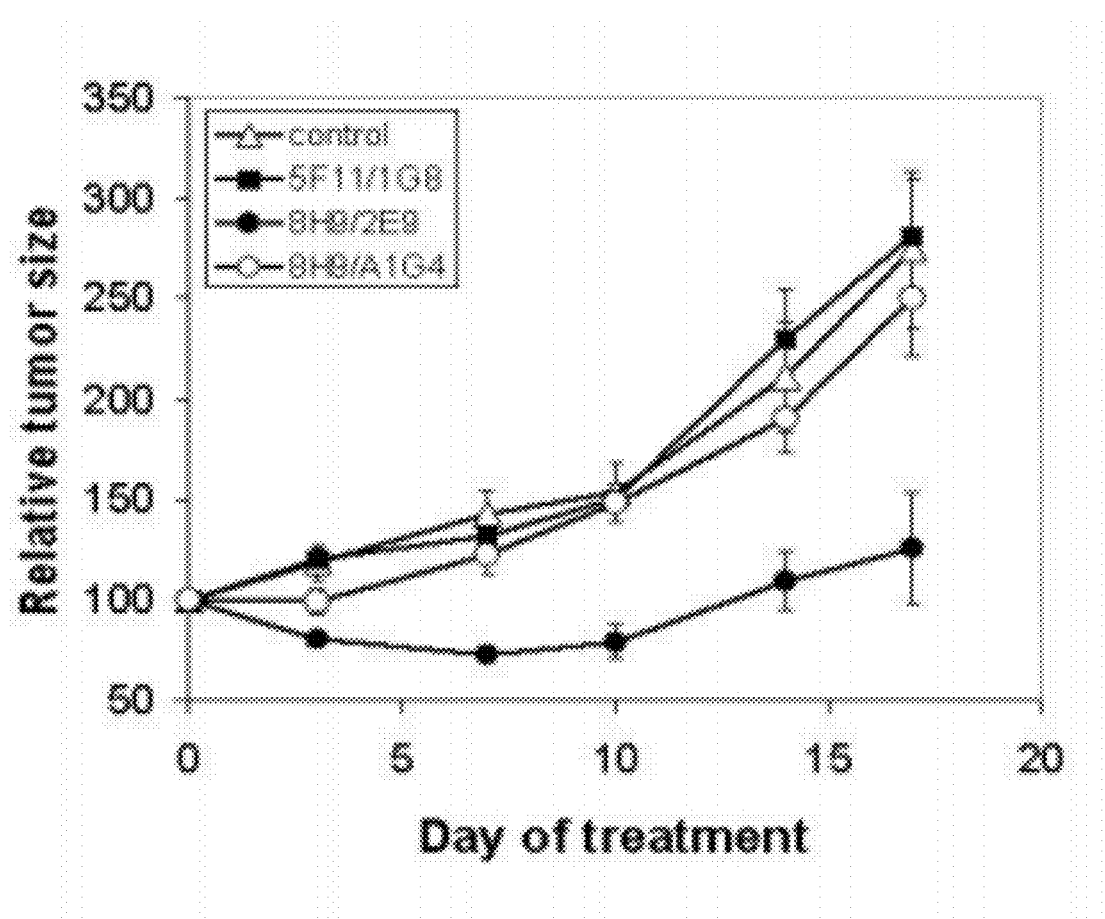

FIG. 13. Suppression of established rhabdomyosarcoma tumor growth in SCID mice. Experimental group: 8H9-scFv-CD28-ζ gene-modified human lymphocytes+ip 2E9 [rat anti-8H9 anti-idiotype MoAb] (solid circles). Control groups: no cells (open triangles), 5F11scFv-CD28-ζ modified lymphocytes+1G8 [rat anti-5F11 anti-idiotype MoAb] (solid squares), and 8H9-scFv-CD28ζ gene-modified human lymphocytes+ip A1G4 [irrelevant rat class-matched MoAb] (open circles). Relative tumor size was calculated as % of initial tumor size (A×B, mean±sem, n=9-10) and plotted over time.

Third Series of the Experiments

Figure 14:
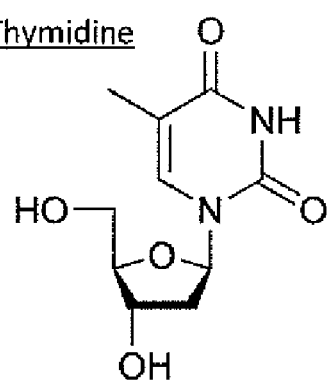
Figure 14:
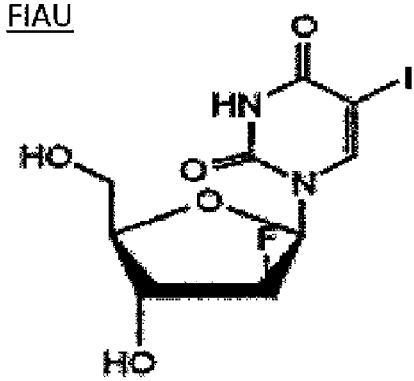

FIG. 14. Transduction of HSV1-tk into primary human T-cells HSV1-tk is a therapeutic gene, a marker gene, as well as a suicide gene. In order to examine the migration of genetically altered antigen-specific t lymphocytes to tumors after adoptive transfer in vivo, we exploited the capacity of transduced T cells expressing HSV-TK to selectively phosphorylate and trap in cells and incorporate into DNA radiolabeled thymidine analog 2'-fluoro-2'deoxy-1-d-arabinofuransyl-5-iodo-uracil.

Figure 15:
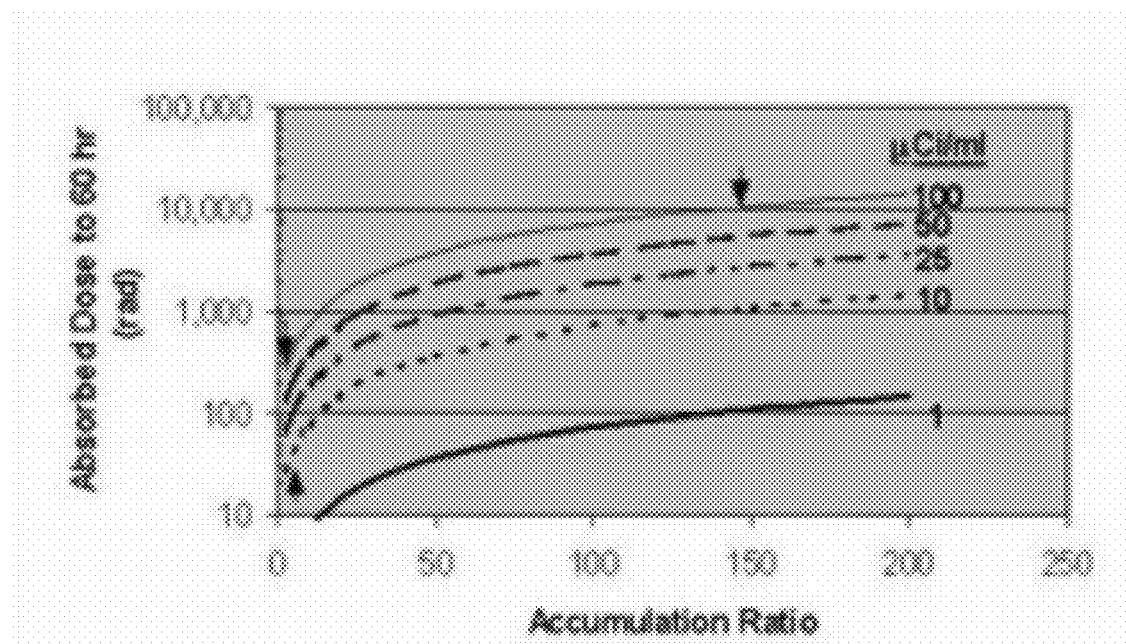

FIG. 15. I131-FIAU absorbed dose to lymphocyte cell nuclei. Based on the forgoing dosimetry model and as presented graphically in this figure, the lymphocyte nucleus absorbed dose was calculated as a function of activity concentration in the medium and the accumulation ratio. To study the effect on T-cell function, [$^{131}I$]-labeled FIAU was incubated with HSV1-tk transduced T cells at 11 ci/ml at 37° C. for 40 to 120 min in increasing activity concentrations of [$^{131}I$]-FIAU from 1.1 to 56 μci/ml, washed and transferred to fresh ([$^{131}I$]-FIAU-free) medium for 72 hr, and then used in a $^{51}CR$-release immune cytotoxicity assay (low effector:target cell ratio=5). There was no demonstrable diminution in immune function up to an absorbed dose (at the reference time of 60 hr) of 1,200 cGy. At greater doses (>1,900 cGy), there was a dose-dependent decrease in immune function.

Figure 16:
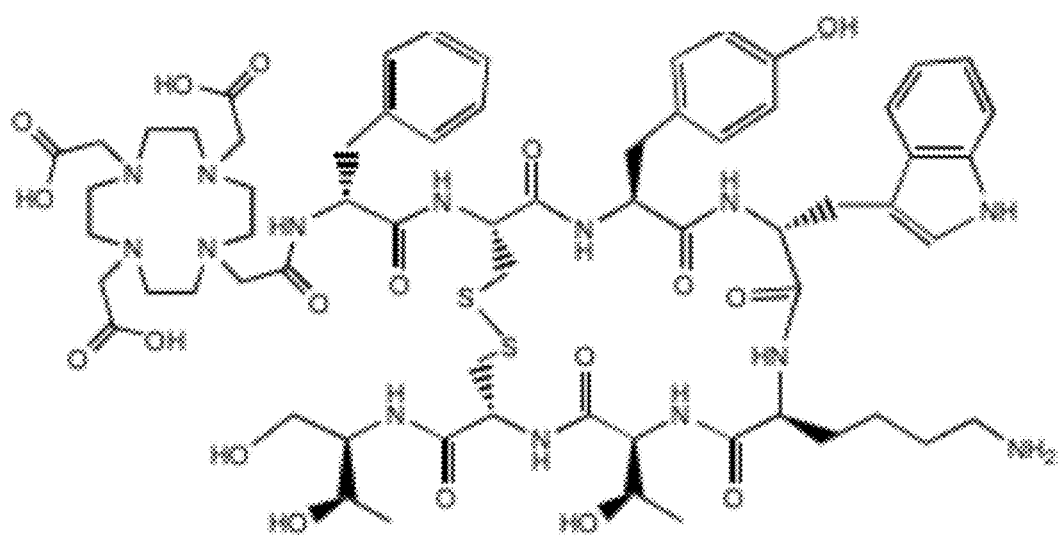

FIG. 16. Structure of DOTA-DPhe$^1$-Tyr$^3$-octreotide (DOTATOC). Radioactive gallium labeled somatostatin analogue DOTA-DPhe$^1$-Tyr$^3$-octreotide (DOTATOC) for positron emission tomography imaging. Radionuclide labeled somatostatin analogues selectively target somatostatin receptor (SSTR)-expressing tumors as a basis for diagnosis and treatment of these tumors. Recently, a DOTA-functionalized somatostatin analogue, DOTATOC has been developed. This compound has been shown to be superior to the other somatostatin analogues as indicated by its uniquely high tumor-to-nontumor tissue ratio. DOTATOC can be labeled with a variety of radiometals including gallium radioisotopes. Gallium-66 is a positron emitting radionuclide ($T_{1/2}$=9.5 hr; $\beta^+$=56%) that can be produced in carrier free form by a low-beam energy cyclotron.

DETAILED DESCRIPTION OF THE INVENTION

The present invention provides a method for making a single chain antibody (scFv) directed against a specific, but not necessarily isolated antigen. The invention further provides a method for identifying cells expressing the target scFv directed against the antigen, and a method for enriching cell populations expressing the target scFv, and for promoting proliferation and expansion of such populations. The invention makes use of an anti-idiotype antibody which is directed to an antibody specific for the antigen. Cells expressing the scFv are recognized by the anti-idiotype, thus allowing their selection. Furthermore, where the scFV is a chimeric immune receptor, which includes a signaling domain in addition to the scFv, the anti-idiotype ligates to these receptors and stimulates proliferation of scFV expressing T-cells.

The generic invention is illustrated with reference to a specific antibody, designated 8H9, of which the antigen is gp58. 8H9 is a murine IgG1 monoclonal antibody specific for a novel antigen on the cell surface of a wide spectrum of human solid tumors, but not on normal tissues. In accordance with the invention, scFv directed against gp58 antibody was prepared using an anti-idiotype directed against the anti-8H9 monoclonal antibody.

In a first aspect, the present invention provides a method for identifying cells expressing a target single chain antibody (scFv) directed against a target antigen from a collection of cells that includes cells that do not express the target scFv. In a second aspect, the present invention provides a method for making an scFv. In each of these aspects of the invention, an anti-idiotype directed against an antibody that is itself directed against the target antigen is utilized.

As used in the specification and claims of this application, the term "directed against" refers to the binding specificity of an antibody. An antibody which is directed against a particular antigen is one which was developed and/or selected by a procedure which involves immunization of an animal with the antigen and/or testing of the antibody for binding with the antigen. The antibody may associate with one or a plurality of epitopes of the target antigen, and may be polyclonal or monoclonal. The term "directed against" does not exclude the possibility of cross-reactivity with other antigens, although antibodies with substantial specificity for the particular target antigen are preferred.

Antibodies directed against the target antigen may be prepared using conventional techniques, including techniques which do not require isolation or specific knowledge of the antigen. In general, an antigen or a sample for which an antibody is to be developed is administered to an organism to stimulate an immune response. For example, cancer tissue samples against which it would be desirable to have an antibody can be administered to mice. Monoclonal antibodies can be developed by fusion of splenic lymphocytes from such immunized mice to myeloma cells to produce a hybridoma. Selection of hybridoma's producing monoclonal antibodies of the desired specificity is carried out in a routine manner by testing for the ability to bind to the original target tissue.

Using this general technique, Applicants have isolated a monoclonal antibody designated 8H9. As described in Modak et al., *Cancer Res.* 61: 4048-4054 (2001), monoclonal antibody 8H9 is a murine IgG1 hybridoma derived from the fusion of mouse myeloma SP2/0 cells and splenic lymphocytes from BALE/c mice immunized with human neuroblastoma. By immunohistochemistry, 8H9 was highly reactive with human brain tumors, childhood sarcomas, and neuroblastomas, and less so with adenocarcinomas. Among primary brain tumors, 15 of 17 glioblastomas, 3 of 4 mixed gliomas, 4 of 11 oligodendrogliomas, 6 of 8 astrocytomas, 2 of 2 meningiomas, 3 of 3 schwannomas, 2 of 2 medulloblastomas, 1 of 1 neurofibroma, 1 of 2 neuronoglial tumors, 2 of 3 ependymomas, and 1 of 1 pineoblastoma tested positive. Among sarcomas, 21 of 21 Ewing's/primitive neuroectodermal tumor, 28 of 29 rhabdomyosarcomas, 28 of 29 osteosarcomas, 35 of 37 desmoplastic small round cell tumors, 2 of 3 synovial sarcomas, 4 of 4 leiomyosarcomas, 1 of 1 malignant fibrous histiocytoma, and 2 of 2 undifferentiated sarcomas tested positive with 8H9. Eighty-seven of 90 neuroblastomas, 12 of 16 melanomas, 3 of 4 hepatoblastomas, 7 of 8 Wilms' tumors, 3 of 3 rhabdoid tumors, and 12 of 27 adenocarcinomas also tested positive. In contrast, 8H9 was nonreactive with normal human tissues including bone marrow, colon, stomach, heart, lung, muscle, thyroid, testes, pancreas, and human brain (frontal lobe, cerebellum, pons, and spinal cord). Reactivity with normal cynomolgus monkey tissue was restricted similarly. Indirect immunofluorescence localized the antigen recognized by 8H9 to the cell membrane.

These characteristics of the antigen recognized by mAB 8H9 ("8H9-antigen") made it a strong potential candidate as a therapeutic target. 8H9 immunoprecipitated a Mr 58,000 band after N-glycanase treatment, most likely a protein with a heterogeneous degree of glycosylation. However, the antigen is proteinase sensitive and is not easily modulated off the cell surface. Thus, preparation and isolation of an scFv which could be used for targeting cells expressing the 8H9-antigen required the development of a different approach.

In accordance with the method of the present invention, the antibody directed against the target antigen is used to create an anti-idiotype antibody. The anti-idiotype antibody can be produced in any species, including human (preferably using in vitro immunization), although mouse and rat will most commonly be immunized because of the convenience of working with such animals in the laboratory. The anti-idiotype is preferably prepared as a monoclonal antibody to make it easier to produce or purify. Once made, the anti-idiotype can be used to screen scFv libraries from any species to identify scFv antibodies directed against the target of the original antibody used to create the anti-idiotype. Thus, as illustrated in the examples below, a rat anti-mouse idiotype was used to screen a human cDNA scFv library.

The procedures for creating scFv libraries are known in the art. Generally, the procedures involve amplification of the variable regions of nucleic acids encoding an antibody, commonly from a hybridoma producing an antibody of interest. Generic primers associated with the constant regions of such antibodies are available commercially. The amplified fragments are then further amplified with primers selected to introduce appropriate restriction sites for introduction of the scFv into an expression vector, phage, or fusion protein. Cells producing the scFv are screened and an scFv with the desired selectivity is identified.

The scFV which is identified can be used in any of numerous applications. For example, the scFv can be labeled, for example using a radiolabel, a colored or chromogenic label or a fluorescent label, and used for diagnostic testing of tissue samples to detect the presence of a tumor-associated target antigen (such as the 8H9-antigen) or other diagnostic antigenic marker. Tissue samples are exposed to the labeled scFv for a period of time to allow specific interaction if the target antigen is present. The sample is washed to remove non-specifically bound materials, and binding of the label to the cells is indicative of the presence of the marker. A similar approach may be used for histological mapping of the location of antigenic markers in tissue sections and samples. The scFv may also be used as one component in sandwich type assays, such as ELISA, and may be used as affinity probes for capture and purification of the target antigen.

The scFv may be used as a targeting moiety to direct chemotherapy agents to specific cell types. The DNA encoding the scFv may also be combined to produce a genetic sequence encoding a fusion protein. Examples of types of fusion proteins which may be created include scFv-cytokine (Shu et al., *Proc. Nat'l Acad. Sci.* (*USA*) 90: 7995-7999 (1993), scFv-streptavidin (Kipriyanov et al., *Human Antibody Hybridomas* 6: 93-101 (1995); WO 97/34634), scFv-enzyme (Michael et al., *Immunotech.* 2: 47-57 (1996)), scFv-toxin (Wickstrand et al., *Cancer Res.* 55: 3140-48 (1995)), bispecific scFv (diabodies) (Alt et al., *FEBS Letters* 454: 90-94 (1999)), bi-specific chelating scFv (De Nardo et al., *Clin., Cancer Res.* 5: 3213s-3218s (1999)), scFv-Ig (Shu et al., supra), tetravalent scFv (Alt et al., supra, Santos et al., *Clin., Cancer Res.* 5: 3118s-3123s (1999)), and scFv-retargeted T cells (Eshar et al., *Proc. Nat'l Acad. Sci* (*USA*) 90: 720-724 (1993)).

In one specific embodiment of the invention, the scFv is coupled in a fusion protein to T-cell signaling and transmembrane domains. Expression of such fusion proteins in T cells leads to presentation of the scFv on the surface of the T cell. Proliferation and expansion of such T cells can be induced by exposing the T cells to which the chimeric scFv has been introduced to an anti-idiotype directed to an antibody specific for a target antigen to which the scFv is directed under conditions such that the anti-idiotype will bind to scFv on the surface of cells expressing the chimeric scFv. Furthermore, such T cells will be targeted in vivo to cells which express the target antigen. Thus, the present invention also provides a method for treating a disease condition characterized by the presence of cells expressing a characteristic surface antigen, comprising the steps of developing an scFv to the target antigen and forming a genetic sequence encoding a fusion protein of the scFv with T cell signaling and transmembrane domains; recovering lymphocytic cells from the patient and transforming the cells ex vivo so that they express the fusion protein, stimulating proliferation and expansion of the cells by exposing the cells ex vivo to an anti-idiotype, and returning the cells to the patient.

This invention also provides compositions comprising the scFv, scFv fusion, and cells expressing scFv, respectively. This invention provides a pharmaceutical composition comprising scFv alone, scFv fusion alone, cells expressing scFv alone, or any combination thereof. This invention further provides a pharmaceutical composition comprising scFv alone, scFv fusion alone, cells expressing scFv alone, or any combination thereof and a pharmaceutically acceptable carrier. For the purposes of this invention, "pharmaceutically acceptable carriers" means any of the standard pharmaceutical carriers. Examples of suitable carriers are well known in the art and may include, but are not limited to, any of the standard pharmaceutical carriers such as a phosphate buffered saline solution and various wetting agents. Other carriers may include additives used in tablets, granules and capsules, etc. Typically such carriers contain excipients such as starch, milk, sugar, certain types of clay, gelatin, stearic acid or salts thereof, magnesium or calcium stearate, talc, vegetable fats or oils, gum, glycols or other known excipients. Such carriers may also include flavor and color additives or other ingredients. Compositions comprising such carriers are formulated by well-known conventional methods.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

From these and the foregoing description, it can be seen that the invention provides:

A method for identifying cells expressing a target scFv directed against a target antigen from a collection of cells that includes cells that do not express the target scFv, comprising the step of combining the collection of cells with an anti-idiotype directed to an antibody specific for the target antigen and detecting interaction, if any, of the anti-idiotype with the cells, wherein the occurrence of an interaction identifies the cell as one which expresses the target scFv. The cells identified by the above method. A composition comprising said cells.

A method for making a scFv directed against an antigen, wherein the selection of clones is made based upon interaction of those clones with an appropriate anti-idiotype, and heretofore inaccessible scFv so made.

The single chain antibody made by the above method and a composition comprising said scFv.

A method for selecting cell lines that package and produce high titers of retroviral particles that carry the scFv gene for transfection into cells. The cells include but are not limited to human lymphocytes.

The selected cell lines from the above method and composition comprising the same.

A method for inducing proliferation in a population of T cells comprising the steps of (a) introducing to the T cells an expressable gene sequence encoding a chimeric scFv coupled to a transmembrane and signaling domain; and (b) exposing the T cells to which the chimeric scFv has been introduced to an anti-idiotype directed to an antibody specific for a target antigen to which the scFv is directed under conditions such that the anti-idiotype will bind to scFv on the surface of cells expressing the chimeric scFv thereby inducing proliferation of the T cells.

The population of T cells induced by the above method and composition comprising the same.

A method for tagging cells to facilitate sorting or enrichment, comprising the steps of expressing a scFv in the cell and capturing or tagging the cells using anti-idiotype.

A method for isolating an antigen comprising the steps of preparing an antibody to the antigen, preparing an anti-idiotype directed to the antibody, using the anti-idiotype to select a scFv, targeting the antigen from a scFv library, and using the selected scFv as an affinity probe to capture antigen, preferably with the scFv immobilized on a solid support.

The isolated antigen by the above method and a composition comprising the same.

A method for treating cancer in a patient suffering from cancer expressing an antigenic marker comprising the steps of removing lymphocytes from the patient, introducing to the lymphocytes an expressable gene sequence encoding a chimeric scFv coupled to a transmembrane and signaling domain; exposing the lymphocytes to which the chimeric scFv has been introduced to an anti-idiotype directed to an antibody specific for a target antigen to which the scFv is directed under conditions such that the anti-idiotype will bind to scFv on the surface of cells expressing the chimeric scFv and any necessary co stimulatory molecules to induce proliferation of the lymphocytes; and returning the expanded population of lymphocytes to the patient. The antigenic marker includes but is not limited to gp58 and GD2.

A method for treating cancer in a patient suffering from cancer expressing an antigenic marker comprising the steps of introducing to human cell lines an expressable gene sequence encoding a chimeric single chain antibody (scFv) coupled to a transmembrane and signaling domain (including zeta chain); exposing the lymphocytes to which the chimeric scFv has been introduced to an anti-idiotype directed to an antibody specific for a target antigen to which the scFv is directed under conditions such that the anti-idiotype will bind to scFv on the surface of cells expressing the chimeric scFv and any necessary co stimulatory molecules to immunoselect and stimulate clones with high density of scFv expression and efficient tumor cytotoxicity to produce a gene-modified cell line, and returning the expanded population of gene-modified cell line to the patient. The antigenic marker includes but is not limited to GD2 and gp58. The human cell line includes but is not limited to NK92, natural killer, helper, and cytotoxic cell line. The gene-modified cell line produced by the above method. A composition comprising the gene-modified cell line.

A method for enhancing in vivo survival and anti-tumor activity of infused lymphocytes gene-modified with scFv-Chimeric immune receptors by intravenous injection of anti-idiotype antibody.

EXPERIMENTAL DETAILS

First Series of Experiments

Anti-Idiotypic Antibody as the Surrogate Antigen for Cloning scFv and Its Fusion Proteins ScFv is a versatile building block for novel targeting constructs. However, a reliable screening and binding assay is often the limiting step for antigens that are difficult to clone or purify. We demonstrate that anti-idiotypic antibodies can be used as surrogate antigens for cloning scFv and their fusion proteins. 8H9 is a murine IgG1 monoclonal antibody specific for a novel antigen expressed on the cell surface of a wide spectrum of human solid tumors but not in normal tissues (Cancer Res 61:4048, 2001) Rat anti-8H9-idiotypic hybridomas (clones 2E9, 1E12 and 1F11) were produced by somatic cell fusion between rat lymphocytes and mouse SP2/0 myeloma. In direct binding assays (ELISA) they were specific for the 8H9 idiotype. Using 2E9 as the surrogate antigen, 8H9-scFv was cloned from hybridoma cDNA by phage display. 8H9scFv was then fused to human-γ1-CH2-CH3 cDNA for transduction into CHO and NSO cells. High expressors of mouse scFv-human Fc chimeric antibody were selected. The secreted homodimer reacted specifically with antigen-positive tumor cells by ELISA and by flow cytometry, inhibitable by the anti-idiotypic antibody. The reduced size resulted in a shorter half-life in vivo, while achieving comparable tumor to nontumor ratio as the native antibody 8H9. However, its in vitro activity in antibody-dependent cell-mediated cytotoxicity was modest.

Introduction

Single chain Fv (scFv) has greatly expanded the potential and development of antibody-based targeted therapies.[1-4] Using phage display, scFv can now be cloned from cDNA libraries derived from rodents, immunized volunteers, or patients.[5-8] The availability of hIg-transgenic and transchromosomal mice will allow immunization schema or pathogens not feasible or safe in humans.

Construction of the scFv is the critical first step in the synthesis of various fusion proteins, including scFv-cytokine,[9] scFv-streptavidin,[10] scFv-enzyme,[11] scFv-toxins,[12] bispecific scFv (diabodies),[13] bispecific chelating scFv,[14] scFv-Ig,[9] tetravalent scFv[13,15] and scFv-retargeted T-cells. ScFv-Ig constructs mimic natural IgG molecules in their homodimerization through the Fc region, as well as their ability to activate complement (CMC) and mediate antibody dependent cell-mediated cytotoxicites (ADCC).

The construction of scFv requires a reliable antigen preparation both for panning phages and for binding assays. They often become a rate-limiting step,[17] particularly for antigens that are difficult to clone or purify. Cell-based phage display,[18] and enzyme linked immunosorbent assays (ELISA) when optimized, have been successfully applied as alternatives. Subtle differences in the panning step can determine the success or failure of phage display.[19] For example, a reduction in wash pH is needed for scFv directed at ganglioside GD2 in order to reduce nonspecific adherence of phage particles.[19] Moreover, phage binding assay may require membrane preparations to withstand the vigorous washing procedure.

As antigen mimics of infectious agents and tumor antigens, anti-idiotypic antibodies have promising clinical potentials.[20-22] They are convenient surrogates when the target antigen is not readily available. The physico-chemical behavior of immunoglobulins as antigens in panning and binding assays is generally known and can be easily standardized. Hombach et al successfully isolated scFv with specificity for CD30 utilizing internal image anti-idiotypic antibodies.[23] We recently described a novel tumor antigen reactive with a murine MoAb 8H9.[24] Given its lability and glycosylation, this antigen is difficult to purify. Here we describe the use of an anti-idiotypic antibody as a surrogate antigen for cloning a scFv derived from the 8H9 hybridoma cDNA library, and for the selection of chimeric mouse scFv-human Fc fusion constructs. This provides a proof of principle for isolating antibodies of same specificity from a non-specific phage display library.

Materials and Methods

Animals

BALE/c mice were purchased from Jackson Laboratories, Bar Harbor, Me. Lou/CN rats were obtained from the National Cancer Institute-Frederick Cancer Center (Bethesda, Md.) and maintained in ventilated cages. Experiments were carried out under a protocol approved by the Institutional Animal Care and Use Committee, and guidelines for the proper and humane use of animals in research were followed.

Cell Lines

Human neuroblastoma cell lines LAN-1 was provided by Dr. Robert Seeger (Children's Hospital of Los Angeles, Los Angeles, Calif.), and NMB7 by Dr. Shuen-Kuei Liao (McMaster University, Ontario, Canada). Cell lines were cultured in 10% defined calf serum (Hyclone, Logan, Utah) in RPMI with 2 mM L-glutamine, 100 U/ml of penicillin (Sigma-Aldrich, St. Louis, Mo.), 100 ug/ml of streptomycin (Sigma-Aldrich), 5% $CO_2$ in a 37° C. humidified incubator. Normal human mononuclear cells were prepared from heparinized bone marrow samples by centrifugation across a Ficoll-Hypaque density separation gradient. Human AB serum (Gemini Bioproducts, Woodland, Calif.) was used as the source of human complement.

Monoclonal Antibodies

Cells were cultured in RPMI 1640 with 10% newborn calf serum (Hyclone, Logan, Utah) supplemented with 2 mM glutamine, 100 U/ml of penicillin and 100 ug/ml of streptomycin (Sigma-Aldrich). 3F8, an IgG3 MoAb raised in a BALE/c mouse against human neuroblastoma, specifically recognizes the ganglioside GD2. The BALE/c myeloma proteins MOPC-104E, TEPC-183, MOPC-351, TEPC-15, MOPC-21, UPC-10, MOPC-141, FLOPC-21, and Y5606 were purchased from Sigma-Aldrich. MoAb R24 (anti-GD3), V1-R24, and K9 (anti-GD3) were gifts from Dr. A. Houghton, OKB7 and M195 (anti-CD33) from Dr. D. Scheinberg, and 10-11 (anti-GM2) from Dr. P. Livingston of Memorial Sloan Kettering Cancer Center, New York; and 528 (EGF-R) from Dr. J. Mendelsohn of MD Anderson, Houston, Tex. 2E6 (rat anti-mouse IgG3) was obtained from hybridomas purchased from American Type Culture Collection [ATCC] (Rockville, Md.). NR-Co-04 was provided by Genetics Institute (Cambridge, Mass.). In our laboratory, 5F9, 8H9, 3A5, 3E7, 1D7, 1A7 were produced against human neuroblastoma; 2C9, 2E10 and 3E6 against human breast carcinoma, and 4B6 against glioblastoma multiforme. They were all purified by protein A or protein G (Pharmacia, Piscataway, N.J.) affinity chromatography.

Anti-8H9 Anti-Idiotypic Antibodies

LOU/CN rats were immunized intraperitoneally (ip) with 8H9 (400 μg per rat) complexed with rabbit anti-rat serum (in 0.15 ml), and emulsified with an equal volume (0.15 ml) of Complete Freund's Adjuvant (CFA) (Gibco-BRL, Gaithersburg, Md.). The 8H9-rabbit-IgG complex was prepared by mixing 2 ml (8 mg) of purified 8H9 with 4 ml of a high titer rabbit anti-rat precipitating serum (Jackson Immunoresearch Laboratories, West Grove, Pa.). After incubation at 4° C. for 3 hours, the precipitate was isolated by centrifugation at 2500 rpm for 10 minutes, and resuspended in PBS. Three months after primary immunization, the rats were boosted ip with the same antigen in CFA. One month later, a 400 μg boost of 8H9-rabbit-anti-mouse complex was injected intravenously. Three days afterwards, the rat spleen was removed aseptically, and purified lymphocytes were hybridized with SP2/0-Ag14 (ATCC). Clones selection was based on specific binding to 8H9 and not to control antibody 5F9, a murine IgG1. Repeated subcloning using limiting dilution was done. Isotypes of the rat monoclonal antibodies were determined by Monoclonal Typing Kit (Sigma-Aldrich). Rat anti-idiotypic antibody clones (2E9, 1E12, 1F11) were chosen and produced by high density miniPERM bioreactor (Unisyn technologies, Hopkinton, Mass.), and purified by protein G affinity chromatography (Hitrap G, Pharmacia). The IgG fraction was eluted with pH 2.7 glycine-HCl buffer and neutralized with 1 M Tris buffer pH 9. After dialysis in PBS at 4° C. for 18 hours, the purified antibody was filtered through a 0.2 um millipore filter (Millipore, Bedford, Mass.), and stored frozen at −70° C. Purity was determined by SDS-PAGE electrophoresis using 7.5% acrylamide gel. 2E9 was chosen from among the three anti-idiotypic antibodies because of its high titer.

The "standard" ELISA to detect rat anti-idiotypic antibodies (Ab2) was as follows: Purified 8H9, or irrelevant IgG1 myeloma, were diluted to 5 ug/ml in PBS and 50 μl per well was added to 96-well flat-bottomed polyvinylchloride (PVC) microtiter plates and incubated for 1 hour at 37° C. Rows with no antigen were used for background subtraction. Filler protein was 0.5% BSA in PBS and was added at 100 μl per well, and incubated for 30 minutes at 4° C. After washing, 50 μl duplicates of hybridoma supernatant was added to the antigen-coated wells and incubated for 3 hours at 37° C. The plates were washed and a peroxidase-conjugated mouse anti-rat IgG+IgM (Jackson Immunoresearch Laboratory) at 100 μl per well was allowed to react for 1 hour at 4° C. The plate was developed using the substrate o-phenylenediamine (Sigma-Aldrich) (0.5 mg/ml) and hydrogen peroxide (0.03%) in 0.1 M citrate phosphate buffer at pH 5. After 30 minutes in the dark, the reaction was quenched with 30 μl of 5 N sulfuric acid and read using an ELISA plate reader.

Specificity by Direct Binding Assay

Fifty μl per well of purified mouse monoclonal antibodies or myelomas were coated onto 96-well PVC microtiter plates at 5 ug/ml for 60 minutes at 37° C., aspirated and then blocked with 100 μl of 0.5% BSA filler protein per well. After washing and air-drying, the wells were allowed to react with anti-idiotypic antibodies. The rest of the procedure was identical to that described in the "standard" assay.

Specificity by Inhibition Assay

To further examine the specificity of these anti-idiotypic antibodies, inhibition of 8H9 immunofluorescent staining of tumor cells by anti-idiotypic antibodies was tested. Purified 8H9 and anti-GD2 MoAb 3F8, (all 10 ug/ml in 0.5% BSA) were preincubated with various concentrations of anti-idiotypic antibodies for 30 minutes on ice before reacting with $10^6$ cells of either GD2-positive/8H9 positive LAN-1 (neuroblastoma) or GD2-negative/8H9-positive HTB-82 (rhabdomyosarcoma). The cells were then washed twice in PBS with 0.1% sodium azide and reacted with FITC-conjugated rat anti-mouse IgG (Biosource, Burlingame, Calif.) on ice for 30 minutes in the dark. The cells were washed in PBS with azide, fixed in 1% paraformaldehyde and analyzed by FACScan (Becton-Dickinson, Calif.). The mean fluorescence was calculated and the inhibition curve computed.

Construction of scFv Gene mRNA was isolated from 8H9 hybridoma cells using Quick Prep Micro mRNA Purification kit (Pharmacia Biotech). $5 \times 10^6$ hybridoma cells cultured in RPMI-1640 medium supplemented 10% calf serum, L-glutamine (2 mmol/L), penicillin (100 u/L) and streptomycin sulphate (100 ug/ml) were pelleted by centrifugation at 800×g and washed once in RNase-free phosphate buffered saline (pH 7.4). Cells were lysed directly in the extraction buffer and Poly(A)-RNA was purified by oligo (dT)-cellulose. The mRNA sample was precipitated from the elution buffer using 100 μg glycogen, 40 μl of 2M potassium acetate solution and 1 ml of absolute ethanol at −20° C. for 1 hour. The nucleic acid was recovered by centrifugation at 10,000×g for 30 min. The sample was evaporated until dry, and dissolved in 20 μl RNase-free water.

ScFv gene was constructed by recombinant phage display. 5 μl of mRNA was reverse-transcribed in a total volume of 11 μl reaction mixture and 1 μl dithiothreitol (DTT) solution for 1 hour at 37° C. For PCR amplification of immunoglobulin variable regions, light chain primer mix and the heavy chain primer sets (Pharmacia) were added, to generate suitable quantities of the heavy (340 bp) and light (325 bp) chains. Following an initial 10 min dwell at 95° C., 5 U AmpliTaq Gold DNA polymerase (Applied Biosystems, Foster City, Calif.) was added. The PCR cycles consisted of a 1 min denaturation step at 94° C., a 2 min annealing step at 55° C. and a 2 min extension step at 72° C. After 30 cycles of amplification, PCR derived fragment was purified by the glassmilk beads (Bio101, Vista, Calif.) and separated by 1.5% agarose gel electrophoresis in TAE buffer, then visualized by ethidium bromide staining. For the assembly and fill-in reaction, both purified heavy chain and light chain fragments were added to an appropriate PCR mixture containing a 15 amino acid linker-primer for 8H9, dNTPs, PCR buffer and Ampli Taq Gold DNA polymerase. PCR reactions were performed at 94° C. for 1 min, followed by a 4 min annealing reaction at 63° C. The heavy and light chain DNA of 8H9 were joined by the linker (GGGS)$_3$ (Pharmacia) into scFv in a VH-VL orientation after 7 thermocycles. Using an assembled scFv DNA of 8H9 as template, a secondary PCR amplification (30 standard PCR cycles) was carried out using primers containing either Sfi I or Not I restriction sites. Thus, the Sfi I and Not I restriction sites were introduced to the 5' end of heavy chain and the 3' end of light chain, respectively. Amplified ScFv DNAs were purified by glassmilk beads and digested with Sfi I and Not I restriction endonucleases. Digestion with Sfi I was carried out in NEBuffer (50 mM NaCl, 10 mM Tris-HCl, 10 mM MgCl$_2$, 1 mM Dithiothreitol, pH 7.9) for 4 hours at 50° C. NotI digestion was carried out in 100 mM NaCl for 4 hours at 37° C. The purified ScFv of 8H9 was inserted into the pHEN1 vector (kindly provided by Dr. G. Winter, Medical Research Council Centre, Cambridge, UK) containing Sfi I/Nco I and Not I restriction sites. Competent *E. coli* XL 1-Blue cells (Stratagene, La Jolla, Calif.) were transformed with the pHEN1 phagemid. Helper phage M13 KO7 (Pharmacia) was added to rescue the recombinant phagemid.

Enrichment of recombinant phagemid by panning 50 µl of anti-8H9 idiotypic antibody 2E9 (50 ug/ml) in PBS was coated on the 96-well PVC microtiter plates and incubated at 37° C. for 1 hour. 100 µl of the supernatant from phage library was added to each well and incubated for 2 hours. The plate was washed 10 times with PBS containing 0.05% BSA. Antigen-positive recombinant phage captured by the anti-idiotype MoAb 2E9 was eluted with 0.1M glycine-HCl (pH 2.2 containing 0.1% BSA) and neutralized with 2M Tris solution. This panning procedure was repeated three times. The phagemid 8HpHM9F7-1 was chosen for the rest of the experiments.

ELISA

The selected phage was used to reinfect *E. coli* XL 1-Blue cells. Colonies were grown in 2xYT medium containing ampicillin (100 ug/ml) and 1% glucose at 30° C. until the optical density of 0.5 unit at 600 nm was obtained. Expression of scFv antibody was induced by changing to the medium containing 100 µM IPTG (Sigma-Aldrich) and incubating at 30° C. overnight. The supernatant was separated by centrifugation. After resuspending the pellet in PBS containing 1 mM EDTA and incubating on ice for 10 min, the soluble antibody in the periplasmic fraction was collected by centrifugation. Both supernatant and periplasmic fractions were added to plates coated with anti-idiotype 2E9. After a 2 hour incubation at 37° C., plates were washed and reacted with anti-MycTag antibody (clone 9E10 from ATCC) for 1 hour at 37° C., and subsequently with affinity purified goat anti-mouse antibody (Jackson Immunoresearch) for 1 hour at 37° C. The plates were developed with the substrate o-phenylenediamine (Sigma-Aldrich) as previously described.

Construction of ScFv-Human-1-CH2-CH3 Mouse Human-Chimeric Gene

A single gene encoding scFv8H9 was generated by PCR method using phagemid 8HpHM9F7-1 as the template. Secondary PCR amplification (30 PCR cycles) was carried out to insert the human IgG1 leader sequence at the 5' end of the scFv8H9 DNA plus the restriction sites at the two opposite ends, i.e. Hind III and Not I, at the 5' end of human IgG1 leader and at the 3' end of scFv8H9, respectively. Amplified human IgG1 leader-scFv8H9 DNA was purified by glassmilk beads and digested with Hind III and Not I restriction endonucleases according to manufacturer's instructions. The Hind III-Not I fragment of human IgG1 leader-scFv8H9 cDNA was purified on agarose gel and ligated into pLNCS23 vector carrying the human-γ1-CH2-CH3 gene (kindly provided by Dr. J. Schlom, National Cancer Institute, NIH, Bethesda, Md.)[9]. Competent *E. coli* XL 1-Blue cells were transformed with pLNCS23 containing the scFv phagemid. The scFv-CH2-CH3 DNA was amplified with appropriate primers and sequenced using the Automated Nucleotide Sequencing System Model 373 (Applied Biosystems). The sequences agreed with the cDNA sequences of the light and heavy chains of 8H9 as well as the human-γ1-CH2-CH3 (GenBank), including the ASN 297 of the CH2 domain. In this construct, Cys220 of the genetic hinge was replaced by a proline residue, while Cys226 and Cys229 were retained in the functional hinge[9]

Cell Culture and Transfection

CHO cell or NSO myelomas cells (Lonza Biologics PLC, Bershire, UK) were cultured in RPMI 1640 (Gibco-BRL) supplemented with glutamine, penicillin, streptomycin (Sigma-Aldrich) and 10% fetal bovine serum (Gibco-BRL). Using effectene transfection reagent (Qiagen, Valencia, Calif.), recombinant cFv8H9-human-γ1-CH2-CH3 was introduced via the pLNCS23 into CHO cell or NSO myelomas cells. Cells were fed every 3 days, and G418 (1 mg/ml; Gibco-BRL) resistant clones were selected. After subcloning by limiting dilution, chimeric antibodies were produced by high density miniPERM bioreactor from Unisyn Technologies using 0.5% ULG-FBS in Hydridoma-SFM (Invitrogen Corporation, Carlsbad, Calif.). The chimeric antibodies were purified by protein G Pharmacia) affinity chromatography.

SDS-PAGE and Western Blot Analysis

The supernatant, the periplasmic extract and cell extract from the positive clones were separated by reducing and nonreducing SDS-PAGE. 10% SDS-polyacrylamide slab gel and buffers were prepared according to Laemmli.[25] Electrophoresis was performed at 100V for 45 min. After completion of the run, western blot was carried out as described by Towbin.[26] The nitrocellulose membrane was blocked by 5% nonfat milk in TBS solution for 1 hour and incubated with anti-idiotype 2E9 antibody overnight at 4° C. After incubating with HRP-conjugated goat anti-rat Ig (Fisher Scientific Co., Pittsburgh, Pa.), the signal was detected by ECL system (Amersham-Pharmacia Biotech).

Cytotoxicity Assay

Target NMB7 or HTB-82 tumor cells were labeled with $Na_2^{51}CrO_4$ (Amersham Pharmacia) at 100 uCi/10$^6$ cells at 37° C. for 1 hour. After the cells were washed, loosely bound $^{51}Cr$ was leaked for 1 hour at 37° C. After further washing, 5000 target cells/well were admixed with lymphocytes to a final volume of 200 µl/well. Antibody dependent cell-mediated cytotoxicity (ADCC) was assayed in the presence of increasing concentrations of chimeric antibody. In complement mediated cytotoxicity (CMC), human serum as source of complement (at 1:40, 1:80, 1:160, 1:320, 1:640 dilution) was used instead of lymphocytes. The plates were incubated at 37° C. for 4 hours. Supernatant was harvested using harvesting frames (Skatron, Lier, Norway). The released $^{51}Cr$ in the supernatant was counted in a universal gamma-counter (Packard Bioscience, Meriden, Conn.). Percentage of specific release was calculated using the formula 100%×(experimental cpm−background cpm)/(10% SDS releasable cpm−background cpm), where cpm were counts per minute of $^{51}Cr$ released. Total release was assessed by lysis with 10% SDS (Sigma-Aldrich), and background release was measured in the absence of cells. The background was usually <30% of total for either NMB7 or HTB-82 cells. Antibody 3F8 was used as the positive control.[27]

Iodination

MoAb was reacted for 5 min with $^{125}I$ (NEN Life Sciences, Boston, Mass.) and chloramine T (1 mg/ml in 0.3M Phosphate buffer, pH 7.2) at room temperature. The reaction was terminated by adding sodium metabisulfite (1 mg/ml in 0.3M Phosphate buffer, pH 7.2) for 2 min. Free iodine was removed with A1GX8 resin (BioRad, Richmond, Calif.) saturated with 1% HSA (New York Blood Center Inc., New York, N.Y.) in PBS, pH 7.4. Radioactive peak was collected and radioactivity (mCi/ml) was measured using a radioisotope calibrator (Squibb, Princeton, N.J.). Iodine incorporation and specific activities were calculated. Trichloroacetic acid (TCA) (Fisher Scientific) precipitable activity was generally >90%.

In Vitro Immunoreactivity of Iodinated Antibody

Immunoreactivity of radioiodine labeled antibody was assayed using purified anti-idiotype antibody 2E9 as the antigen. Appropriate dilutions of $^{125}I$ labeled antibodies were added to plates in duplicates, and then transferred to freshly prepared antigen plates after 1 h and 4 h of binding at 4° C., respectively. The final binding step was allowed to proceed overnight at 4° C. The total percent radioactivity bound was a summation of 3 time points for each antibody dilution. For native 8H9, maximum immunoreactivity averaged ~65%, while 8H9 scFv-Fc (ch8H9) antibody was ~48%.

Animal Studies

Athymic nude mice (nu/nu) were purchased from NCI, Frederick M D. They were xenografted subcutaneously with LAN-1 neuroblastoma cell line ($2 \times 10^6$ cells/mouse) suspended in 100 μl of Matrigel (Beckton-Dickinson BioSciences, Bedford, Mass.) on the flank. After 3 weeks, mice bearing tumors of 1-1.5 cm in longest dimension were selected. Animals were injected intravenously (retrorbital plexus) with 20 μCi of $^{125}I$ labeled antibody. They were anesthesized with ketamine (Fort Dodge Animal Health, Fort Dodge, Pa.) intraperitoneally and imaged at various time intervals with a gamma camera (ADAC, Milpitas, Calif.) equipped with grid collimators. Serial blood samples were collected at 5 min, 1, 2, 4, 8, 18, 24, 48, 72, 120 h from mice injected with 10-11 uCi $^{125}I$ labeled antibody. Groups of mice were sacrificed at 24 h, 48 h, and 120 h and samples of blood (cardiac sampling), heart, lung, liver, kidney, spleen, stomach, adrenal, small bowel, large bowel, spine, femur, muscle, skin, brain and tumor were weighed and radioactivity measured by a gamma counter. Results were expressed as percent injected dose per gram. Animal experiments were carried out under an IACUC approved protocol, and institutional guidelines for the proper and humane use of animals in research were followed.

Results

Anti-8H9-Idiotypic Antibodies

Rat hybridomas specific for 8H9 and nonreactive with control murine IgG1 were selected. After subcloning by limiting dilution, rat antibodies were produced by bulk culture in roller bottles and purified by protein G affinity column. By ELISA, 2E9, 1E12, and 1F11, all of rat subclass IgG2a, were specific for 8H9, while nonreactive with a large panel of purified monoclonal antibodies (Table 1). In contrast, the antibodies 3C2, 4C2 5C7, 7D6 and 8E12 from the same fusions were not specific for 8H9. The rest of the experiments in this study was carried out using antibody 2E9 because of its high titer in vitro. 2E9 specifically inhibited the binding of 8H9 to LAN-1 neuroblastoma (FIG. 1A) and HTB82 rhabdomyosarcoma (FIG. 1B) while control rat IgG1 (A1G4) had no effect (FIG. 1C).

Construction and Expression of 8H9 ScFv

After three rounds of panning of the recombinant phagemid on the anti-idiotypic antibody 2E9, the eluted phage was used to infect *E. coli* HB2151 cells and scFv expression was induced by IPTG. ScFv from periplasmic soluble protein fraction was tested for binding to 2E9 on ELISA. Three 8H9 scFv clones when compared with the MoAb 8H9 showed similar titers. The clone 8HpHM9F7-1 was selected for subcloning. The DNA sequence of 8HpHM9F7-1 agreed with those of the 8H9VH and 8H9VL.

The supernatant, periplasmic soluble and cells pellet lysates of 8HpHM9F7-1 were separated by nonreducing SDS-PAGE, and analyzed by western blotting. A protein band with molecular weight of 31 KD was found in the supernatant, the periplasmic and cell pellet extracts using anti-MycTag antibody which recognized the sequence GAPVPDPLEPR (SEQ ID NO. 18). No such band was detected in control cells or 8HpHM9F7-1 cells without IPTG treatment.

Construction of Chimeric Mouse scFv-Human Fc

Chimeric clones from CHO and NSO were screened by ELISA binding on 2E9. Clone 105 from NSO and clone 1G1 from CHO were chosen for scale-up production. By SDS-PAGE and by western blot analysis, a single chain of 54 kD under reducing conditions, and a homodimer of 102 kD under nonreducing conditions were found (FIG. 2). Antigen specificity was demonstrated by its binding to tumor cells. In FIG. 3, mean fluorescence plateaued around 3-5 ug/mL of both ch8H9 and 8H9 for both HTB-rhabdomyosarcoma and LAN-1 neuroblastoma cells, while negative (<10% mean fluorescence) for the control cell line Daudi (data not shown). Cell staining (5 ug/ml of ch8H9) was completely inhibited by 1 ug/ml of anti-idiotypic antibody 2E9 on FACS analysis (data not shown). DNA sequencing confirmed the presence of 8H9scFv and the CH2-CH3 domain of human Fcγ1.

In Vitro and In Vivo Properties of ch8H9

The ch8H9 antibody mediated ADCC in the presence of human lymphocytes with a 16% maximum cytotoxicity at 50:1 E:T ratio, significantly higher than the controls 3F8 or 8H9 (FIG. 4A). However, it was unable to mediate CMC in the presence of human complement (data not shown). In biodistribution studies, it localized well to HTB82 and LAN-1 xenografts (FIG. 5). Blood clearance studies showed that chimeric 8H9 (102 kD MW) had T-½ of 5.3 h, and T-½ of 43 h when compared to averages of 4.5 h and 71 h, respectively, for native 8H9 (160 kD MW), a result of the smaller molecular size of the construct (FIG. 6). Similarly, although the percent injected dose per gram of the chimeric construct (Table 2) was lower for all tissues (average of 44% at 48 h, and 75% at 120 h), the tumor-non tumor ratios (Table 3) were similar to those of native 8H9 (98% at 48 h and 85% at 120 h).

Discussion

We demonstrated that by using rat anti-idiotypic antibody as antigen surrogate, scFv and scFv-fusion proteins can be conveniently produced. As proof of principle we utilized the anti-idiotypic antibody to clone scFv from the murine hybridoma cDNA library. The anti-idiotypic antibody was then used to select for scFv-Fc chimeric antibodies. Both the scFv and scFv-Fc fusion protein derived by our method were specific for the natural antigen, comparable to the native antibody 8H9.

While scFv provides the building block for scFv-fusion proteins, it is not the ideal targeting agent by itself. Being a small protein, its clearance is rapid. Moreover, it is often retained by the kidney, delivering undesirable side effects if the scFv construct is cytotoxic. Since avidity is a key parameter in tumor targeting in vivo, its biggest limitation is its uni-valency and often suboptimal affinity for the antigen. By using VH-VL linkers of decreasing length, spontaneous dimeric, trimeric and polymeric scFv have been produced. However, these oligomers are not bonded by covalent linkage, and may dissociate in vivo. An alternative approach is to take advantage of the human Fc, which has the natural ability to homodimerize through disulfide-bonds, thereby allowing the juxtaposition of two binding domains. Fc functions such as CMC and ADCC could also be achieved.[9,28-31]

Unlike standard 2-chain chimeric antibodies, only one polypeptide is needed for the scFv-Fc chimeric; unbalanced synthesis of heavy and light chains is not an issue. Larger dimeric fragments are also likely to have increased serum-half life compared to scFv and thus improved tumor targeting.[32,33] Homodimerization of tumor cell-surface antigens by soluble antibody may also trigger apoptosis of tumor cells.[34] No less important is the availability of validated purification techniques using protein A or protein G through their binding to the Fc portion.[31] Tetravalent scFv (monospecific or bispecific) are natural extensions of the diabody approach to scFv-Fc fusion strategy,[13,15] where a significant increase in avidity can be achieved. More recently, scFv-streptavidin fusion protein has been produced for pre-targeted lymphoma therapy.[35] Here scFv-streptavidin forms natural tetramers, to which biotinyated ligands can bind with high affinity.

Anti-idiotypic antibodies have greatly facilitated clone selection in the construction of soluble scFv-fusion proteins or cell bound surface scFv. We have successfully applied similar technology to anti-GD2 monoclonal antibodies.[36] Being immunoglobulins, their structure, stability, biochemistry, are generally known. Unlike natural antigens where each individual system has its unique and difficult to predict properties. As surrogate antigens, anti-idiotypic antibodies are ideal for standardization and quality control, especially for initial clinical investigations where the nature of the antigen is not fully understood. Potential limitations exist for the anti-idiotype approach. Only those anti-ids (Ab2) that recognize the antigen-binding site of the immunizing MoAb can mimic the original antigen. A reliable test for Ab2 is its ability to induce an antigen-specific immune response. Alternatively, antigen specificity of the scFv selected by the anti-idiotype must be validated by binding to cells or membrane preparations.

Once validated, the anti-idiotype can be used as antigen surrogate for cloning and assay of other scFv-fusion proteins. Although our scFv-Fc fusion protein ch8H9 mediated ADCC, it could not mediate CMC. This finding differs from previous scFv-Fc fusion proteins.[9,30,31] It is possible that the affinity of the antibody 8H9 may be suboptimal to mediate efficient ADCC/CMC; or that the p58 antigen and tumor lines used may not be optimal targets for CMC. Alternatively, poor in vitro Fc function may relate to the oligosaccharide structures in the Fc region.[37] In normal IgG, these oligosaccharides are generally of complex biantennary type, with low levels of terminal sialic acid and bisecting N-acetylglucosamine (GlcNAc), the latter being critical for ADCC. ADCC function is often inefficient among chimeric antibodies expressed in cell lines which lack the enzyme (1,4)-N-acetylglucosaminyltransferase III (GnIII),[38] that catalyzes the formation of bisecting oligosaccharides. This enzyme can be transfected into producer lines to increase the level of bisecting GlcNAc and to increase the ADCC function of secreted chimeric antibodies.[38] It is also possible that the absence of the CH1 domain in the Fc may modify the accessability of the ASN297 residue to glycosyltransferases in some scFv-Fc constructs such as ours.[37] On the other hand, an scFv-Fc that lacks binding to Fc receptor may have less nonspecific binding to white cells, thereby decreasing blood pooling in targeted therapy. These findings may have implications in scFv-Fc strategies to improve effector functions.

TABLE 1

Anti-8H9-idiotypic antibodies: Specificity by ELISA

| MoAb | Class | 1E12 2a | 1F11 2a | 3C2 2b | 4C2 μ | 5C7 μ | 7D6 1 | 8E12 μ | 2E9 2a |
|---|---|---|---|---|---|---|---|---|---|
| MOPC-315 | a | − | − | +++ | − | − | − | − | − |
| 20.4 | 1 | − | − | +++ | +++ | ++ | +++ | − | − |
| 2C9 | 1 | − | − | +++ | +++ | +++ | +++ | ++ | − |
| 2E10 | 1 | − | − | +++ | − | − | + | − | − |
| 3E6 | 1 | − | − | +++ | +++ | +++ | +++ | +++ | − |
| 3E7 | 1 | − | − | +++ | − | − | + | − | − |
| 4B6 | 1 | − | − | +++ | +++ | ++ | +++ | − | − |
| 5F9 | 1 | − | − | +++ | +++ | +++ | +++ | + | − |
| 8H9 | 1 | +++ | ++ | +++ | +++ | ++ | +++ | − | ++ |
| MOPC-21 | 1 | − | − | +++ | +++ | +++ | +++ | − | − |
| UJ 13A | 1 | − | − | +++ | ++ | + | − | − | − |
| 3A5 | 2a | − | − | +++ | − | − | − | − | − |
| MOPC-1 | 2a | − | − | +++ | + | − | − | − | − |
| 3F8 | 3 | − | − | +++ | − | − | − | − | − |
| FLOPC-21 | 3 | − | − | +++ | ++ | − | ++ | − | − |
| NRCO-04 | 3 | − | − | +++ | − | − | − | − | − |
| R24 | 3 | − | − | +++ | − | − | − | − | − |
| TIB114 | 3 | − | − | +++ | + | − | ++ | − | − |
| Y5606 | 3 | − | − | +++ | − | − | − | − | − |
| 3A7 | μ | − | − | + | − | − | − | − | − |
| 3G6 | μ | − | − | +++ | − | − | − | − | − |
| 5F11 | μ | − | − | + | − | − | − | − | − |
| K9 | μ | − | − | +++ | − | − | − | − | − |
| MOPC-104E | μ | − | − | +++ | − | − | − | − | − |

Note:
OD < 0.5 = −, 0.5~1 = +, 1~2 = ++, >2 = +++

TABLE 2

Percent Injected Dose per gram over time in hours

Percent injected dose/gm over time (h) mean +/− se

| Organs | Chimeric | | | Native | |
|---|---|---|---|---|---|
|  | 24 | 48 | 120 | 48 | 120 |
| Skin | 1.4 +/− 0.2 | 0.2 +/− 0.1 | 0.7 +/− 0.0 | 0.2 +/− 0.0 | 1.8 +/− 0.2 |
| Heart | 1.3 +/− 0.2 | 0.2 +/− 0.1 | 0.9 +/− 0.0 | 0.4 +/− 0.2 | 2.6 +/− 0.2 |
| Lung | 2.9 +/− 0.4 | 0.4 +/− 0.3 | 1.9 +/− 0.1 | 0.5 +/− 0.3 | 4.0 +/− 0.3 |
| Liver | 1.2 +/− 0.1 | 0.1 +/− 0.1 | 0.8 +/− 0.0 | 0.2 +/− 0.2 | 1.4 +/− 0.2 |
| Spleen | 0.9 +/− 0.2 | 0.2 +/− 0.0 | 0.5 +/− 0.1 | 0.2 +/− 0.2 | 1.4 +/− 0.1 |
| Kidney | 1.5 +/− 0.1 | 0.1 +/− 0.1 | 0.9 +/− 0.2 | 0.5 +/− 0.1 | 1.9 +/− 0.1 |
| Adrenal | 0.9 +/− 0.1 | 0.1 +/− 0.2 | 0.5 +/− 0.2 | 0.5 +/− 0.5 | 1.8 +/− 0.0 |
| Stomach | 1.3 +/− 0.3 | 0.3 +/− 0.1 | 0.6 +/− 0.1 | 0.3 +/− 0.1 | 1.3 +/− 0.3 |
| Samll intestine | 0.6 +/− 0.1 | 0.1 +/− 0.0 | 0.3 +/− 0.1 | 0.2 +/− 0.0 | 0.7 +/− 0.1 |
| Large intestine | 0.6 +/− 0.1 | 0.1 +/− 0.0 | 0.3 +/− 0.1 | 0.2 +/− 0.1 | 0.6 +/− 0.0 |
| Bladder | 1.2 +/− 0.1 | 0.1 +/− 0.2 | 0.6 +/− 0.2 | 0.4 +/− 0.2 | 1.0 +/− 0.2 |
| Muscle | 0.5 +/− 0.1 | 0.1 +/− 0.0 | 0.3 +/− 0.1 | 0.2 +/− 0.0 | 0.5 +/− 0.1 |
| Femur | 0.6 +/− 0.1 | 0.1 +/− 0.0 | 0.3 +/− 0.1 | 0.2 +/− 0.1 | 0.8 +/− 0.0 |
| Spine | 0.6 +/− 0.1 | 0.1 +/− 0.0 | 0.4 +/− 0.1 | 0.2 +/− 0.1 | 0.8 +/− 0.1 |
| Tumor | 4.0 +/− 0.3 | 0.3 +/− 0.5 | 3.6 +/− 0.4 | 2.1 +/− 1.3 | 9.4 +/− 0.5 |
| Brain | 0.2 +/− 0.0 | 0.0 +/− 0.0 | 0.1 +/− 0.0 | 0.1 +/− 0.0 | 0.2 +/− 0.0 |
| Blood | 5.3 +/− 0.3 | 0.3 +/− 0.3 | 3.1 +/− 0.2 | 1.2 +/− 0.7 | 8.3 +/− 0.8 |

TABLE 3

Tumor to normal tissue over time in hours

Tumor to normal tissue ratio over time (h), mean +/− se

| Organs | Chimeric | | | Native | |
|---|---|---|---|---|---|
|  | 24 | 48 | 120 | 48 | 120 |
| Skin | 3.0 +/− 0.3 | 6.0 +/− 1.3 | 10.7 +/− 1.7 | 5.2 +/− 0.7 | 7.2 +/− 2.2 |
| Heart | 3.3 +/− 0.7 | 4.0 +/− 0.7 | 5.6 +/− 0.4 | 3.6 +/− 0.3 | 7.7 +/− 2.9 |
| Lung | 1.6 +/− 0.4 | 2.2 +/− 0.5 | 4.5 +/− 0.7 | 2.3 +/− 0.3 | 5.0 +/− 1.7 |
| Liver | 3.5 +/− 0.5 | 5.2 +/− 1.3 | 8.7 +/− 1.1 | 6.5 +/− 0.4 | 0.1 +/− 3.4 |
| Spleen | 5.1 +/− 1.0 | 8.1 +/− 1.6 | 12.8 +/− 3.4 | 6.7 +/− 0.4 | 15.1 +/− 5.7 |
| Kidney | 2.8 +/− 0.3 | 4.3 +/− 1.1 | 5.9 +/− 1.6 | 5.1 +/− 1.0 | 8.9 +/− 1.1 |
| Adrenal | 4.8 +/− 0.5 | 8.7 +/− 2.3 | 10.0 +/− 3.2 | 5.8 +/− 1.3 | 11.6 +/− 1.6 |
| Stomach | 3.6 +/− 0.8 | 6.7 +/− 1.3 | 13.8 +/− 4.2 | 7.5 +/− 1.7 | 14.5 +/− 4.3 |
| Samll intestine | 6.6 +/− 0.7 | 11.8 +/− 2.1 | 16.0 +/− 3.7 | 13.3 +/− 2.2 | 21.7 +/− 6.1 |
| Large intestine | 7.1 +/− 1.0 | 12.7 +/− 2.2 | 25.9 +/− 7.1 | 15.7 +/− 3.4 | 28.5 +/− 8.9 |
| Bladder | 3.5 +/− 0.3 | 14.3 +/− 9.2 | 10.2 +/− 3.3 | 12.4 +/− 5.5 | 12.3 +/− 5.3 |
| Muscle | 7.9 +/− 0.7 | 13.6 +/− 2.4 | 21.3 +/− 6.8 | 18.2 +/− 1.3 | 26.8 +/− 9.6 |
| Femur | 6.7 +/− 1.1 | 11.8 +/− 2.4 | 20.5 +/− 6.8 | 11.8 +/− 1.3 | 27.9 +/− 6.5 |
| Spine | 6.7 +/− 0.9 | 6.8 +/− 1.9 | 14.2 +/− 3.7 | 11.1 +/− 1.1 | 19.6 +/− 6.2 |
| Tumor | 1.0 +/− 0.0 | 1.0 +/− 0.0 | 1.0 +/− 0.0 | 1.0 +/− 0.0 | 1.0 +/− 0.0 |
| Brain | 22.7 +/− 2.9 | 40.9 +/− 8.6 | 38.7 +/− 10.4 | 44.6 +/− 10.4 | 68.2 +/− 35.2 |
| Blood | 0.8 +/− 0.1 | 1.2 +/− 0.2 | 1.8 +/− 0.3 | 1.1 +/− 0.1 | 2.3 +/− 0.8 |

REFERENCES

1. Huston J S, Levinson D, Mudgett-Hunter M, Tai M S, Novotny J, Margolies M N, Ridge R J, Bruccoleri R E, Haber E, Crea R: Protein engineering of antibody binding sites: recovery of specific activity in an anti-digoxin single-chain Fv analogue produced in *Escherichia coli*. Proceedings of the National Academy of Sciences of the United States of America 85:5879-5883, 1988
2. Bird R E, Hardman K D, Jacobson J W, Johnson S, Kaufman B M, Lee S M, Lee T, Pope S H, Riordan G S, Whitlow M: Single-chain antigen-binding proteins. Science 242: 423-426, 1988
3. Winter G, Milstein C: Man-made antibodies. Nature 349: 293-299, 1991
4. George A J T, Spooner R A, Epenetos A A: Applications of Monoclonal Antibodies in Clinical Oncology. Immunology Today 15:559-561, 1994
5. Winter G, Griffiths A D, Hawkins R E, Hoogenboom H R: Making antibodies by phage display technology. Annual Review of Immunology 12:433-455, 1994
6. Raag R, Whitlow M: Single-chain Fvs. FASEB Journal 9:73-80, 1995
7. Burton D R, Barbas III C G: Human antibodies from combinatorial libraries. Advances in Immunology 57:191-280, 1994
8. Cai X, Garen A: Anti-melanoma antibodies from melanoma patients immunized with genetically modified autologous tumor cells: selection of specific antibodies from single-chain Fv fusion phage libraries. Proceedings of the National Academy of Sciences of the United States of America 92:6537-6541, 1995
9. Shu L, Qi C F, Schlom J, Kashmiri S V: Secretion of a single-gene-encoded immunoglobulin from myeloma cells. Proceedings of the National Academy of Sciences of the United States of America 90:7995-7999, 1993
10. Kipriyanov S M, Bretling F, Little M, Dubel S: Single-chain antibody streptavidin fusions: tetrameric bifunctional scFv-complexes with biotin binding activity and enhanced affinity to antigen. Human Antibodies Hybridomas 6:93-101, 1995
11. Michael N P, Chester K A, Melton R G, Robson L, Nicholas W, Boden J A, Pedley R B, Begent R H, Sherwood R F, Minton N P: In vitro and in vivo characterisation of a recombinant carboxypeptidase G2::anti-CEA scFv fusion protein. Immunotechnology 2:47-57, 1996
12. Wikstrand C J, Hale L P, Batra S K, Hill M L, Humphrey P A, Kurpad S N, McLendon R E, Moscatello D, Pegram C N, Reist C J: Monoclonal antibodies against EGFRvIII are tumor specific and react with breast and lung carcinomas and malignant gliomas. Cancer Research 55:3140-3148, 1995
13. Alt M, Muller R, Kontermann R E: Novel tetravalent and bispecific IgG-like antibody molecules combining single-chain diabodies with the immunoglobulin γ1 Fc or CH3 region. FEES Letters 454:90-94, 1999
14. DeNardo S J, DeNardo G L, DeNardo D G, Xiong C Y, Shi X B, Winthrop M D, Kroger L A, Carter P: Antibody phage libraries for the next generation of tumor targeting radioimmunotherapeutics. Clinical Cancer Research 5:3213s-3218s, 1999
15. Santos A D, Kashmiri S V, Hand P H, Schlom J, Padlan E A: Generation and characterization of a single gene-encoded single-chain-tetravalent antitumor antibody. Clinical Cancer Research 5:3118s-3123s, 1999
16. Eshhar Z, Waks T, Gross G, Schindler D G: Specific activation and targeting of cytotoxic lymphocytes through chimeric single chains consisting of antibody-binding domains and the gamma or zeta subunits of the immunoglobulin and T-cell receptors. Proceedings of the National Academy of Sciences of the United States of America 90:720-724, 1993
17. Lu J, Sloan S R: An alternating selection strategy for cloning phage display antibodies. Journal of Immunological Methods 228:109-119, 1999
18. Watters J M, Telleman P, Junghans R P: An optimized method for cell-based phage display panning. Immunotechnology 3:21-29, 1997
19. Tur M K, Huhn M, Sasse S, Engert A, Barth S: Selection of scFv phages on intact cells under low pH conditions leads to a significant loss of insert-free phages. Biotechniques 30:404-413, 2001
20. Koprowski H, Herlyn D, Lubeck M, DeFreitas E, Sears H F: Human anti-idiotype antibodies in cancer patients: Is the modulation of the immune response beneficial for the patient? Proc. Natl. Acad Sci, USA 81:216-219, 1984
21. Thanavala Y M, Brown S E, Howard C R, Roitt I M, Steward M W: A surrogate hepatitis B virus antigenic epitope represented by a synthetic peptide and an internal image antiidiotype antibody. Journal of Experimental Medicine 164:227-236, 1986
22. Wagner U, Schlebusch H, Kohler S, Schmolling J, Grunn U, Krebs D: Immunological responses to the tumor-associated antigen CA125 in patients with advanced ovarian cancer induced by the murine monoclonal anti-idiotype vaccine ACA125. Hybridoma 16:33-40, 1997
23. Hombach A, Pohl C, Heuser C, Sircar R, Diehl V, Abken H: Isolation of single chain antibody fragments with specificity for cell surface antigens by phage display utilizing internal image anti-idiotypic antibodies. J Immunol Methods 218:53-61, 1998
24. Modak S, Kramer K, Humayun G, Guo H F, Cheung N K V: Monoclonal antibody 8H9 targets a novel cell surface antigen expressed by a wide spectrum of human solid tumors. Cancer Research 61:4048-4054, 2001
25. Laemmli U K: Cleavage of structural proteins during the assembly of the head of bacteriophage T4. Nature 227:680-685, 1970
26. Towbin H, Staehelin T, Gordon J: Electrophoretic transfer of proteins from polyacrylamide gels to nitrocellulose sheets: procedure and some applications. Proceedings of the National Academy of Sciences of the United States of America 76:4350-4354, 1979
27. Cheung N K, Saarinen U, Neely J, Landmeier B, Donovan D, Coccia P: Monoclonal antibodies to a glycolipid antigen on human neuroblastoma cells. Cancer Research 45:2642-2649, 1985
28. Kato T, Sato K, Suzuki S, Sasakawa H, Kurokawa M, Nishioka K, Yamamoto K: Mammalian expression of single chain variable region fragments dimerized by Fc regions. Molecular Biology Reports 21:141-146, 1995
29. Brocks B, Rode H J, Klein M, Gerlach E, Dubel S, Little M, Pfizenmaier K, Moosmayer D: A TNF receptor antagonistic scFv, which is not secreted in mammalian cells, is expressed as a soluble mono- and bivalent scFv derivative in insect cells. Immunotechnology 3:173-184, 1997
30. Wang B, Chen Y B, Ayalon O, Bender J, Garen A: Human single-chain Fv immunoconjugates targeted to a melanoma-associated chondroitin sulfate proteoglycan mediate specific lysis of human melanoma cells by natural killer cells and complement. Proceedings of the National Academy of Sciences of the United States of America 96:1627-1632, 1999
31. Powers D B, Amersdorfer P, Poul M A, Nielsen U B, Shalaby R, Adams G P, Weiner L M, Marks J D: Expression of single-chain Fv-Fc fusions in pinchia pastoris. Journal of Immunological Methods 251:123-135, 2001
32. Adams G P, McGartney J E, Tai M-S, Oppermann H, Huston J S, Stafford W F, Bookman M A, Fand I, Houston L L, Weiner L W: Highly specific in vivo tumor targeting by monovalent and divalent forms of 741F8 anti-c-erbB-2 single-chain Fv. Cancer Research 53:4026-4034, 1993
33. Wu A M, Chen W, Raubitschek A, Williams L E, Neumaier M, Fischer R, Hu S Z, Odom-Maryon T, Wong J Y, Shively J E: Tumor localization of anti-CEA single-chain Fvs: improved targeting by non-covalent dimers. Immunotechnology 2:21-36, 1996
34. Ghetie M A, Podar E M, Ilgen A, Gordon B E, Uhr J W, Vitetta E S: Homodimerization of tumor-reactive monoclonal antibodies markedly increases their ability to induce growth arrest or apoptosis of tumor cells. Proceedings of the National Academy of Sciences of the United States of America 94:7509-7514, 1997
35. Schultz J, Lin Y, Sanderson J, Zuo Y, Stone D, Mallett R, Wilbert S, Axworthy D: A tetravalent single-chain antibody-streptavidin fusion protein for pretargeted lymphoma therapy. Cancer Research 60:6663-6669, 2000
36. Cheung N K, Canete A, Cheung I Y, Ye J N, Liu C: Disialoganglioside GD2 anti-idiotypic monoclonal antibodies. International Journal of Cancer 54:499-505, 1993
37. Wright A, Morrison S L: Effect of glycosylation on antibody function: implications for genetic engineering. Trends in Biotechnology 15:26-31, 1997

38. Umana P, Jean-Mairet J, Moudry R, Amstutz H, Bailey J E: Engineered glycoforms of an antineuroblastoma IgG1 with optimized antibody-dependent cellular cytotoxic activity. Nature Biotechnology 17:176-180, 1999

Second Series of Experiments

Anti-Idiotypic Antibody Facilitates scFv Chimeric Immune Receptor Gene Transduction and Clonal Expansion of Human Lymphocytes for Tumor Therapy Experimental Details Chimeric immune receptors (CIR) transduced into lymphocytes link target recognition by single chain antibody Fv (scFv) to activation through CD28/TCRζ signaling. As surrogate antigens, anti-idiotypic antibodies may facilitate gene-transduction and clonal expansion of human lymphocytes for in vivo tumor therapy. The murine monoclonal antibody (MoAb) 8H9 reacts with a novel antigen widely expressed on solid tumors (Cancer Res 61:4048, 2001). A CIR consisting of human CD8-leader sequence, 8H9scFv, CD28 (transmembrane and cytoplasmic domains), and TCR-ζ chain was constructed, ligated into the pMSCVneo vector, and used to transfect the packaging line GP+envAM12 bearing an amphotropic envelope. Rat anti-idiotypic MoAb 2E9 (IgG2a) was used to clone retroviral producer line as well as to expand gene-modified primary human lymphocytes. Sequential enrichments using either affinity chromatography or cell sorting using anti-idiotypic MoAb 2E9 significantly improved the percentage of producer clones positive for surface 8H9-scFv and the efficiency of their supernatant in transducing the indicator cell line K562. By three weeks of in vitro culture, >95% of transduced primary human lymphocytes were CIR-positive. Upon periodic stimulation with 2E9, these lymphocytes underwent >$10^6$ fold expansion by 6 months in culture. They mediated antigen-specific non-MHC restricted cytokine release and tumor cytotoxicity. When admixed with tumor cells or injected intravenously, they inhibited human xenograft growth in SCID mice. Anti-idiotypic antibody may provide a useful tool for optimizing gene transduction of CIR fusion constructs into primary human lymphocytes and their continual expansion in vitro.

Adoptive cell therapy using ex vivo expanded tumor-selective T-cells can effect dramatic remissions of virally induced malignancies, a process critically dependent on clonal frequency, where rapid exponential expansion of specific cytolytic T-lymphocytes (CTL) is required. (Papadopoulos, 1994 #2140; Heslop, 1997 #4703) T-cells proliferate when activated (e.g. anti-CD3). However, apoptosis occurs unless a costimulatory signal (e.g. anti-CD28) is present. (Daniel, 1997 #4714) However, human tumor targets often lack costimulatory molecules (e.g. CD80), or overstimulate inhibitory receptors (e.g. CTL4) such that the CD28 pathway is derailed. In addition, many tumors downregulate major histocompatibility complex (MHC) molecules to escape engagement by the T-cell receptor (TCR). Through genetic engineering, chimeric immune receptors (CIR) linking tumor-selective scFv to T-cell signal transduction molecules (e.g. TCR-ζ chain and CD28) will activate lymphocytes following tumor recognition, triggering the production of cytokines and tumor lysis. (Eshhar, 1993 #6028; Stancovski, 1993 #2392; Moritz, 1994 #3399; Wels, 1995 #2452; Hwu, 1993 #2394; Eshhar, 2001 #5665; Rossig, 2001 #6088; Ma, 2002 #6437) T-cell can also be genetically engineered to secrete cytotoxic cytokines, (Rosenberg, 1995 #2372) toxins, (Yang, 1997 #3395) or to metabolize prodrugs. (Culver, 1992 #3478; Wei, 1994 #3466) However, significant technologic gaps remain: (1) Gene transduction into primary human lymphocytes is inefficient, (2) Antigen specific T-cells cannot be easily enriched and expanded, (3) Optimal T-cell activation may require multiple signals, and (4) Demonstration of antitumor effect of these human T-cells in established tumor models has been difficult and so far unsuccessful in patients. (Ma, 2002 #6437) Furthermore, although CIR redirected T-cells can recycle their lytic activity, (Weijtens, 1996 #3396) a costimulatory signal, either through CD28 or 4-1BB engagement, may help reduce activation-induced apoptotic death. (Maus, 2002 #6438) CIR with multidomains was recently described, where the intracellular domain of CD28 was ligated to the 5' end of TCR-ζ chain and introduced into Jurkat cells, with the expected "two signals" when scFv was triggered by tumor cells. (Finney, 1998 #4574) IL-2 production was 20 times more than CIR with ζ-chain only. Primary mouse CD8+ T lymphocytes expressing the scFv-CD28-ζ receptor secreted Tc1 cytokines, induced T-cell proliferation, and inhibited established tumor growth and metastasis in vivo, a process shown to be critically dependent on IFN-γ secretion. (Haynes, 2002 #6477) CD28-mediated cytokine secretion through CIR activation was recently demonstrated in primary human T-cells. (Krause, 1998 #3956; Maher, 2002 #6433)

To monitor scFv gene expression, anti-linker antibody may be useful. However, its efficiency depends on the accessibility of the scFv-linker portion. Although purified antigens can also be used to monitor scFv expression, certain classes (complex carbohydrates or unstable antigens) can be difficult to prepare and their chemistry highly variable. Without a standardized reagent for affinity purification or enrichment of virus producer cells, as well as monitoring and sorting of transduced lymphocytes, CIR technology remains inefficient. A dicistronic construct consisting of scFv-CD28-γ and green fluorescent protein (GFP) exploited the latter was to monitor gene transduction and to enrich producer lines. (Eshhar, 2001 #5665) Although GFP can validate the gene transfer process, its added immunogenicity and its safety in clinical applications remain uncertain.

Anti-idiotypic antibodies are frequently used as antigen-mimics for infectious diseases and cancer. Thanavala, 1986 #3290; Wagner, 1997 #6019) Internal image rat anti-idiotypic antibodies can be conveniently produced against mouse MoAb. Since large scale production of clinical grade MoAb is now routine, anti-idiotypic antibodies may be ideal surrogates especially if the antigen is not readily available. In addition, the biochemistry of immunoglobulins in positive selection (panning, affinity chromatography, sorting) and binding assays is well-known and is easy to standardize. Single chain antibody fragments with specificity for cell surface antigens were successfully isolated by phage display utilizing internal image anti-idiotypic antibodies. (Hombach, 1998 #6363) We recently described a novel tumor antigen reactive with a murine MoAb 8H9. (Modak, 2001 #3872) The antigen was difficult to purify given its lability and glycosylation. Here we demonstrate that an anti-idiotypic MoAb against 8H9 can be used as a surrogate antigen for cloning CIR into primary human lymphocytes, i.e. a CIR of 8H9scFv, human CD28 and human TCR-ζ chain. While previous studies showed that anti-idiotypic antibody can enhance cytotoxicity of scFv-γR-gene modified murine cytotoxic T-cell line, (Reinhold, 1999 #4340) we now show that anti-idiotypic MoAb, besides allowing rapid affinity enrichment of producer cell line and monitoring of surface scFv expression, induces clonal expansion of CIR-modified primary human lymphocytes. Highly cytotoxic lymphocytes can be propagated in vitro undergoing $10^6$ fold expansion over a period of 6 months.

Materials and Methods

Materials Cells were cultured in RPMI 1640 with 10% newborn calf serum Hyclone, Logan, Utah) supplemented with 2 mM glutamine, 100 U/ml of penicillin and 100 ug/ml of streptomycin. 8H9 murine IgG1 monoclonal antibody directed at gp58 on human solid tumors has been previously described. (Modak, 2001 #3872) Anti-idiotypic antibodies were produced from LOU/CN rats. (Cheung, 1993 #1499) Clones (2E9, 1E12, 1F11) were selected based on selective binding to 8H9 antibody and not to other myelomas. After repeated subcloning, 2E9 (rat IgG2a) was chosen for its high in vitro antibody production using high density miniPERM bioreactor (Unisyn technologies, Hopkinton, Mass.), and purified by protein G affinity chromatography (Hitrap G, Amersham-Pharmacia, Piscataway, N.J.). The IgG fraction was eluted with pH 2.7 glycine-HCl buffer and neutralized with 1 M Tris buffer pH 9. After dialysis in PBS at 4° C. for 18 hours, the purified antibody was filtered through a 0.2 um Millipore filter (Millipore Inc. Bedford Mass.), and stored frozen at −70° C. Purity was determined by SDS-PAGE electrophoresis using 7.5% acrylamide gel. ELISA was used to detect rat anti-idiotypic antibodies (Ab2) as previously described. (Cheung, 1993 #1499) Rat IgG1 anti-5F11 anti-idiotypic MoAb 1G8 was similarly produced.

Construction of ScFv Gene scFv was constructed from 8H9 hybridoma cDNA by recombinant phage display (Amersham-Pharmacia). Amplified ScFv DNA, purified by glassmilk beads, restriction digested (Sfi I and Not I), and inserted into the pHEN1 vector (kindly provided by Dr. G. Winter, Medical Research Council Centre, Carmbridge, UK). Competent *E. Coli* XL-1 Blue cells (Stratagene, La Jolla, Calif.) were transformed with the pHEN1 phagemid. Following rescue with the helper phage M13 KO7 (Pharmacia), recombinant phagemids were enriched by panning. 50 ul of anti-8H9 idiotypic antibody 2E9 (50 ug/ml) in PBS were coated on the 96-well polyvinyl microtiter plates and incubated at 37° C. for 1 hour. 100 ul of the supernatant from phage library were added to each well and incubated for 2 hours. The plate was washed 10 times with PBS containing 0.05% BSA. Antigen-positive recombinant phage captured by anti-idiotypic MoAb 2E9 was eluted with 0.1M HCl (pH 2.2 with solid glycine and 0.1% BSA) and neutralized with 2M Tris solution. This panning procedure was repeated three times. The phagemid 8HpHM9F7-1 was chosen for the rest of the experiments. The appropriate size scFv (31 kD) was demonstrated in the supernatant, periplasmic and cell extracts by nonreducing SDS-PAGE and western blotting. (Towbin, 1979 #6020) using anti-Myc Tag antibody (clone 9E10 from ATCC, Rockville, Bethesda, Md.).

ELISA The selected phage was used to reinfect *E. coli* XL-1 Blue cells. Colonies were grown in 2xYT medium containing ampicillin (100 ug/ml) and 1% glucose at 30° C. until the optical density at 600 nm of 0.5 was obtained, and expression of scFv antibody was induced with 100 uM IPTG (Sigma-Aldrich) at 30° C. overnight. Both supernatant and periplasmic fractions were assayed for scFv on anti-idiotype 2E9 coated plates. After incubating 2 hours at 37° C., plates were washed and reacted with anti-MycTag antibody for 1 hour at 37° C. After washing, affinity purified goat anti-mouse antibody (Jackson Immunoresearch, West Grove, Pa.) was allowed to react for 1 hour at 37° C. and the plates were developed with the substrate o-phenylenediamine (Sigma-Aldrich).

Construction of sc8H9-hCD28$_{TM}$-hCD28$_{cyto}$-hTCRζ-pMSCVneo Using the assembled gene sequences, secondary PCR amplifications using synthetic oligodeoxynucleotide primers (see below) were performed. Briefly, a 541 reaction mixture containing 200 μM of each deoxynucleotide triphosphate, 0.2 μM of each primer, 2 units of AmpliTaq Gold DNA polymerase (Applied Biosystems, Foster City, Calif.), and 50 ng of template DNA was subjected to a 10 min denaturation and activation step at 95° C., followed by 30 cycles of denaturation (1 min at 95° C.), annealing (2 min at 55° C.), and extension (2 min at 72° C.). This was followed by a final extension for 8 min at 72° C. Each of the amplified products was purified with Geneclean Kit (Bio 101, Vista, Calif.).

Synthetic Oligodeoxynucleotide Primers for DNA Amplification (1) hCD8a leader-scFv-CD28:

(SEQ ID NO. 1)
Sense Primer (Hpa I-Human CD8a Leader)
5'-TTA TTA CGA GTT/AAC ATG GCC TTA CCA GTG ACC-3'

(SEQ ID NO. 2)
Antisense Primer (Xho I-Human CD28)
5'-CTT GGT C/TCGAG TGT CAG GAG CGA TAG GCT GC-3'

(2) 8H9scFv:

(SEQ ID NO. 3)
Sense Primer (Cla I-8H9 heavy chain)
5'-TTA TTA CGA AT/CGAT T GCC CAG GTC AAA CTG-3'

(SEQ ID NO. 4)
Antisense Primer (Not I- 8H9 light chain)
5'-CTT GGT G/CGGCCGC CTG TTT CAG CTC CAG-3'

(3) 5F11scFv:

(SEQ ID NO. 5)
Sense Primer (Cla I-5F11 heavy chain)
5'-TTA TTA CGA AT/CGAT TCA GCA GTC AGG ACC-3'

(SEQ ID NO. 6)
Antisense Primer (Not I-5F11 light chain)
5'-CTT GGT G/CG GCC GC CCG TTT TAT TTC CAA CTG-3'

(4) hTCR-ζ chain:

(SEQ ID NO. 7)
Sense primer (Bst U I- CD28 end-Xho I-hTCRζ [cytoplasmic domain])
5'- CG/C GAC TTA GCA GCC TAT CGC TCC TGg CAC/TCG AGa AGA GTG AAG TTC-3'

Antisense Primer (BglII-hTCR z)

(SEQ ID NO. 8)
5'-CTT GGT A/GA TCT TCA GCG AGG GGG CAG GGC-3'

Templates for DNA Amplification and Construction The single gene encoding hCD8a-leader-sc3G6-CD28 was previously described. (Krause, 1998 #3956) Its cDNA was generated by PCR using the Hpa I, Xho I fragment of hCD8a-leader-scFv-CD28 cDNA, and ligated into pMSCVneo vector (Clontech, Palo Alto, Calif.). ScFv-8H9 was amplified from the 8HpHM9F7-1 phagemid, and the excised 8H9 scFv gene swapped into the hCD8a-leader-scFv3G6-CD28 cassette of pMSCVneo using the Cla I-Not I restriction enzymes. Human TCR-ζ chain was amplified from the plasmid pcDNA3.1/VJABLZH (kindly provided by Dr. Ira Bergman, University of Pittsburgh, Pa.), and ligated downstream of CD28 gene, using Xho I and Bgl II restriction sites. Using the method supplied by manufacturer (Stratagene), competent *E. Coli* XL-1 Blue cells were transformed with the vector pMSCVneo containing the insert. All gene constructs were checked by DNA sequencing.

Cell Culture and Transfection The amphotropic packaging cell line GP+envAM12 (Genetix Pharmaceuticals, Cambridge, Mass.) and all retroviral producer lines were maintained in Dulbecco's modified Eagle's medium (Gibco-BRL, Gaithersburg, Md.) supplemented with glutamine, penicillin, streptomycin (Gibco-BRL), and 10% fetal bovine serum (Gibco-BRL). Using Effectene Reagent (Qiagen, Valencia, Calif.), vector DNA was transfected into GP+envAM12 packaging cells and selected with G418 (400 ug/ml; Gibco-BRL).

Enrichment and Cloning of Packing Lines by Affinity Column The retroviral producer lines were affinity enriched using MACS goat anti-rat IgG MicroBeads on the Mini-MACS system (Miltenyi, Auburn, Calif.). In brief, the transduced packing lines were reacted with 2E9 (10 ug per $10^6$ packing cells) on ice for 30 minutes, washed, applied to the anti-rat column, and eluted according to manufacturer's protocol. Cloning was done by limiting dilution. scFv expression on producer clones were monitored by flow cytometry (FACSCalibur, Becton Dickinson Immunocytometry Systems, San Jose, Calif.) using anti-idiotypic antibodies 2E9 or 1E12. Virus-containing supernatant was used to infect K562 cells, and gene transduction was measured by scFv surface expression.

Enrichment and Cloning of Packing Lines by FACS sorting Cell sorting was carried out using a Cytomation MoFlo digital cell sorter (Cytomation Inc., Fort Collins, Colo.), selecting for the brightest (0.1%) 2E9-reactive cells, and seeded into 96-well plates at 10 cells per well.

Peripheral Blood Mononuclear Cells (PBMC) Peripheral blood from normal volunteers and patients were obtained aseptically with informed consent according to the guidelines of the Institutional Review Board of Memorial Sloan-Kettering Cancer Center. PBMC were isolated by centrifugation on Ficoll (density, 1.077 g/ml) for 30 min at 25° C. and washed twice with PBS. PBMC ($10^6$/ml) were cultured in RPMI 1640 supplemented with 10% human AB serum (Gemini Bio-Products, Woodland, Calif.), 50 μM 2-mercaptoethanol, 2 μM L-glutamine, and 1% penicillin-streptomycin (Gibco-BRL), and activated with solid phase anti-CD3 (1 μg/ml; clone OKT3; PharMingen, San Diego, Calif.) and anti-CD28 (1 ug/ml; clone CD28.2; PharMingen) MoAbs for 3 days at 37° C. before retroviral transfection. (Koehne, 2000 #5893)

Retroviral Transduction Protocol PBMC or K562 were suspended at 1-5×$10^5$ cells/ml of freshly harvested supernatant from retroviral producer cells, containing 8-10 ug/ml hexadimethrine bromide (polybrene, Sigma-Aldrich), centrifuged at 1000×g at room temperature for 60 minutes, before culturing in 12-well tissue plates overnight. The viral supernatant was then aspirated and fresh IMDM (Gibco-BRL) medium containing 100 U/ml of IL2 and changed approximately every 5 days to maintain a cell count between 1-2×$10^6$ cells/ml. (Koehne, 2000 #5893) Transfected cells were cultured in wells coated with anti-idiotypic antibody 2E9, for 2 consecutive days each from weeks 3 to 7, and then transferred to plates freshly coated with 2E9 at every 3 weeks intervals.

Real-Time Quantitative PCR Real-time quantitative PCR for scFv gene copy number and RT-PCR for mRNA were performed on cryopreserved lymphocyte samples using ABI Prism 7700 Sequence Detection System (Applied Biosystems, Foster City, Calif.) as previously described. (Mora, 2001 #6436; Cheung, 2001 #5733) β-actin was the endogenous control for DNA, whereas glyceraldehyde-3-phosphate dehydrogenase (GAPDH) for mRNA. Primers and probe for scFv were designed using the Applications-based primer design software Primer Express (Applied Biosystems, ABI). The primers and probes for β-actin and GAPDH were from ABI.

```
8H9scFv
sense primer:                               (SEQ ID NO. 9)
5'- CAAATATGCTTCCCAATCCATCT-3' antisense primer:                           (SEQ ID NO. 10)
5'- ACTGAGAGTGAAATCTGACCCTGAT-3'

Probe:                                      (SEQ ID NO. 11)
FAM-5'-TCCCCTCCAGGTTCAGTGGCAGTG-3'-TAMRA β-actin
sense primer:                               (SEQ ID NO. 12)
5'- TCACCCACACTGTGCCCATCTACGA-3' antisense primer:                           (SEQ ID NO. 13)
5'- CAGCGGACCCGCTCATTGCCAATGG-3'

Probe:                                      (SEQ ID NO. 14)
FAM-5'-ATGCCC-TAMRA-CCCCCATGCCATCCTGCGTp-3'

GAPDH
sense primer:                               (SEQ ID NO. 15)
5'-GAAGGTGAAGGTCGGAGTC-3' antisense primer:                           (SEQ ID NO. 16)
5'-GAAGATGGTGATGGGATTTC-3'.

Probe:                                      (SEQ ID NO. 17)
VIC-5'CAAGCTTCCCGTTCTCAGCC-3'-TAMRA
```

DNA and mRNA were extracted from cryopreserved lymphocyte samples and processed as previously described. (Mora, 2001 #6436; Cheung, 2001 #5733) Every PCR run was in duplicates and included a 5-point standard to generate a standard curve for scFv and for its corresponding endogenous control, plus a no template control. scFv standard was prepared from purified plasmid DNA, while β-actin and GAPDH standards were purchased from ABI. For DNA samples, scFv copy number was normalized by the β-actin level. For cDNA samples, scFv transcript was normalized to that of GAPDH. The variation in the quantitation from experiment to experiment was within 15%. Western blotting was carried out on lysate of scFv-modified T-cells using murine monoclonal anti-zeta antibody (BD Biosciences, Pharmingen, San Diego, Calif.; clone 8D3, 1 ug/ml final dilution) and HRP conjugated goat-anti-mouse affinity purified antibody (Jackson Immunoresearch, 1:1000 final dilution) as previously described. (Maher, 2002 #6433)

Cytotoxicity Assay Neuroblastoma targets NMB-7 and LAN-1, or rhabdomyosarcoma target HTB-82 were labeled with $Na_2^{51}CrO_4$ (Amersham Pharmacia) at 100 uCi/$10^6$ cells at 37° C. for 1 hour. After the cells were washed, loosely bound $^{51}Cr$ was removed by washing. 5000 target cells/well were admixed with lymphocytes to a final volume of 200 μl/well. Following a 3 minute centrifugation at 200×g, the plates were incubated at 37° C. for 4 hours. Supernatant was harvested using harvesting frames (Skatron, Lier, Norway). The released $^{51}Cr$ in the supernatant was counted in a universal gamma-counter (Packard Bioscience, Meriden, Conn.). Percentage of specific release was calculated using the formula 100%×(experimental cpm−background cpm)/(10% SDS releasable cpm−background cpm), where cpm are counts per minute of $^{51}Cr$ released. Total release was assessed by lysis with 10% SDS (Sigma-Aldrich), and background release was measured in the absence of cells. The background was usually <30% of total for these cell lines.

ELISPOT Assays 96-well PVDF plates (MAHA 54510, Millipore, Bedford, Mass.) were coated with 100 ml of anti- IFNγ monoclonal antibody (10 µg/ml, Endogen, Woburn, Mass.) overnight at 4° C. The plates were washed with RPMI 1640 and then blocked for 1.5 hour at 37° C. with IMDM supplemented with glutamine (Gibco-BRL), penicillin, and streptomycin (Gibco-BRL), and 10% pooled human AB serum (Gemini). To transduced human lymphocytes ($10^5$/ml in medium containing 10% human serum, and 100 µl/well) tumor targets were added at various effector:target ratios and cultured for 26 hr at 37° C. in 5% $CO_2$. Plates were washed free of cells and reacted with biotinylated anti-IFNγ (2.0 µg/ml) for 3 hr at room temperature, before washing and reacting with a 1:1000 dilution of streptavidin-HRP conjugate (Zymed Laboratories, South San Francisco, Calif.) diluted in PBS containing 0.5% BSA for an additional 1-2 hr at room temperature. The colorimetric substrate was 3-amino-9-ethyl-carbazole (Sigma-Aldrich) at 0.33 mg/ml in 50 mM sodium acetate buffer (pH 5) containing 0.015% hydrogen peroxide. After incubation at room temperature for 8 min, the color reaction was stopped by rinsing the plates under running tap water and Elispots counted under a microscope.

Adoptive cell therapy of human xenograft in immune deficient mice CB-17 SCID-Beige mice were purchased from Taconic (Germantown, N.Y.). Two types of tumor models were used, a Winn assay (Wang, 1980 #6517) and an established tumor model. In the Winn assay, tumor cells ($10^6$ cells) were mixed with T-cells at various tumor-lymphocyte ratios and planted in 100 ul of Matrigel (BD BioSciences, Bedford, Mass.) subcutaneously. Following implantation, tumor sizes (product of orthogonal diameters) were measured. In established tumor model, tumor cells ($2 \times 10^6$ cells) alone were planted subcutaneously. Here, cell therapy was started in groups of 5 mice per cage when tumor diameter reached 0.8 cm, usually by 1-2 weeks of tumor implantation. Mice received 5 weekly intravenous CIR-gene modified lymphocyte injections by retroorbital route, $2 \times 10^6$ per injection together with 500 U of IL-2 ip. 50 ug of anti-idiotypic or control antibody was administered ip 3 days after each lymphocyte injection. Tumor sizes were measured twice a week. Experiments were carried out under an IACUC approved protocol and institutional guidelines for the proper, and humane use of animals in research were followed.

Statistical Analysis Data were calculated as Mean+/−SEM. Differences between treatment groups were tested for significance (<0.05) by student t-test.

Results

Construction of sc8H9-CD28-hTCR-ζ-pMSCVneo Using synthetic oligodeoxynucleotide primers 355S, 355A for the hCD8a leader-scFv-CD28, 365S, 365A for scFv8H9, and 379S, 379A for hTCR-ζ-chain, the gene hCD8-leader-8H9scFv-hCD28TM-hCD28cyto-TCRζ was constructed, sequence-verified and transfected into the amphotropic packaging line GP+envAM12, and selected in G418. Enrichment and cloning of producer lines by affinity chromatography and cell sorting. The retroviral producer lines were affinity-enriched using MACS goat anti-rat IgG microbeads on the MiniMACS system. Following each enrichment, viral supernatant from the producer line was used to infect the indicator cell line K562. Surface 8H9-scFv expression on both the producer lines and the transfected K562 (4 days after infection) were measured by immunofluorescence using anti-idiotypic antibody 2E9. With each successive affinity enrichment (FIGS. 7a and 7c) of producer line and subsequent successive subcloning (FIGS. 7b and 7d), the surface expression (mean fluorescence) of 8H9-scFv increased and became more homogeneous for the producer clones (FIGS. 7a and 7b) as well as indicator line K562 (FIGS. 7c and 7d). Table 1 summarized the length of time (in weeks) required to enrich for scFv-positive producer cell line.

Retroviral transduction of primary human peripheral blood mononuclear cells Following in vitro activation with anti-CD3 and anti-CD28, primary human PBMC were infected with the virus from producer line supernatant by centrifugation at 1000×g for 60 minutes at room temperature. Using PBMC from normal volunteers, the in vitro requirement of IL2 and anti-idiotypic antibody for lymphocyte expansion was studied (FIG. 8). On day 10 after gene transduction, 17-40% of cells became scFv-positive by FACS analysis. By day 15, 75-80% became positive and by day 24, 99% of the cells became positive. This clonal evolution to homogeneity was found in CD4+, CD8+ and the small CD56+ populations. IL-2 concentration of 50 to 100 U/ml appeared optimum, and anti-idiotypic MoAb 2E9 was absolutely necessary to maintain prolonged T-cell growth (FIG. 8). These experiments were repeated twice with similar results. In the presence of 100 U/ml of IL2 and solid-phase anti-idiotypic antibodies, PBMC from 4 patients with stage 4 neuroblastoma off chemotherapy and 4 separate specimens from two normal volunteers, were expanded in vitro following CIR-gene transduction (FIG. 9). Continual expansion ($10^3$ to $10^8$ fold) was achieved after 150-200 days of culture, with a doubling time ranging from 5 to 10 days. 8H9scFv average gene copy number, transcript level, and surface expression were studied in these samples (FIG. 10). The scFv-positive population enriched quickly during the first 20 days of culture in the absence of 2E9 (FIG. 10a). As expected, the gene copy number and transcript level also plateaued with similar kinetics (FIG. 10b). When the scFv-positive population became >95%, an average of 4.5 gene copies per cell (range 2-9) was detected, which remained relatively stable throughout the extensive length of in vitro culture. ScFv expression was typically >95% throughout 6 months of culture (FIG. 10a). By western blot analysis, the scFv-CD28-zeta chimeric protein was primarily a tetramer (MW-210 kD) under nonreducing conditions and a monomer of 54 kD in the presence of 2-mercaptoethanol. The proportion of CD8+ cells versus CD4+ cells increased steadily to >50% by day 40 of culture, and decreased slowly over 3-4 months. At concentrations of IL-2<50 U/ml, CD4+ cells outgrew the CD8+ population even faster (data not shown). T-cells expanded in the presence of anti-CD3, anti-CD28 and IL-2 (Koehne, 2002 #6442) were unable to kill HTB-82 cells in vitro (data not shown).

Transduced lymphocytes mediated non MHC-restricted antigen-specific cytotoxicity in vitro against neuroblastoma and rhabdomyosarcoma cell lines In vitro cytotoxicity against NMB-7 (FIG. 11a) and LAN-1 (FIG. 11b) neuroblastoma, or rhabdomyosarcoma HTB-82 (FIG. 11c) were efficient. Antigen-dependence was demonstrated by the total inhibition of cytotoxicties by MoAb 8H9 (FIG. 11) and anti-idiotypic antibody 2E9 (data not shown). Daudi cell line (FIG. 11D) was not killed because it was antigen-negative. This cytotoxicity was independent of target HLA expression or HLA types (data not shown). Unmodified lymphocytes from the same donor, cultured under the same conditions (100 U/ml of IL2), did not show antigen-specific killing (FIG. 11). Control (5F11scFv) CIR modified lymphocytes also did not show antigen-specific killing of HTB82 (data not shown). In Elispot assays, IFN-7 secretion was detected when transduced lymphocytes were stimulated with antigen-positive tumors (NMB7 and HTB82) but not antigen-negative controls (Daudi, data not shown).

Adoptive cell therapy of rhabdomyosarcoma xenograft in SCID mice. Human rhabdomyosarcoma is strongly reactive with 8H9, but not with 5F11 (anti-$G_{D2}$) antibodies.

5F11scFv-CIR contained the same CD28-TCR construct used for 8H9scFv-CIR. 8H9scFv-CIR gene-modified lymphocytes suppressed HTB82 tumor growth, when mixed at 1:0.5 (tumor to T-cell), 1:1 or 1:10 ratios at the time of tumor implantation (FIG. 12). While all the mice in control group (tumor alone) or irrelevant T-cell (5F11scFv-CIR gene-modified lymphocytes) group developed rapid tumor growth, in the presence of specific T-cells (8H9), tumor was completely suppressed. When anti-idiotype 2E9 was injected q 3 days×3 after tumor implantation, the anti-tumor effect was substantially reduced, in contrast to control antibody 1G8 or saline control. This inhibitory effect of 2E9 on the effector phase was consistent with in vitro findings (FIG. 11). However, when 8H9scFv-CIR gene-modified lymphocytes was tested in an established tumor model, the growth sustaining function of specific anti-idiotypic antibody became more apparent. Here experiments were initiated when tumors grew to around 0.8 cm diameter. Control groups were injected with either (1) no cells plus 2E9 ip, (2) 5F11scFv-CIR modified lymphocytes intravenously plus anti-idiotype 1G8 (specific for 5F11 idiotype) ip or (3) 8H9scFv-CIR modified lymphocytes intravenously plus A1G4 (irrelevant anti-idiotypic antibody) ip. Suppression of tumor growth was most significant with lymphocytes transduced with the 8H9scFv-CIR gene (o) (FIG. 8, p<0.05), and only if the specific anti-idiotype 2E9 was administered. 5F11scFv-CIR modified lymphocytes or 8H9scFv-CIR plus A1G4 did not show significant anti-tumor effect when compared to control. This in vivo effect of gene-modified lymphocytes was demonstrated in 3 separate experiment.

Discussion

We have demonstrated that primary human lymphocytes could be stably transduced with a scFv-CD28-ζ fusion gene carried by a retroviral vector to express surface scFv. Anti-idiotypic antibody directed at the scFv facilitated the cloning of the producer cell line and monitoring of gene expression. These CIR-gene modified lymphocytes could proliferate in the presence of anti-idiotypic antibody to undergo $10^6$ expansion in both CD4+ and CD8+ populations over a period of 6 months. These cells responded in an antigen-specific manner in vitro by cytokine release and tumor cytotoxicity. By virtue of their near 100% CIR expression, they were more efficient than T-cells activated in the presence of anti-CD3/anti-CD28 and IL2. They effectively inhibited tumor growth in a xenograft tumor model in a Winn assay as well as in an established subcutaneous tumor model where T-cells were injected intravenously. Gene transduction was successful whether lymphocytes were derived from normal volunteers or patients. Our data suggest that although the CIR alone permitted survival of transduced lymphocytes during the first 3 weeks, anti-idiotypic antibody was necessary for proliferation beyond this initial period. Several observations on the scFv-modified T-cells were novel: the chimeric immune receptor homodimerized to a tetrameric form, T-cells expressing CIR demonstrated growth and survival advantage, anti-idiotypic antibody could inhibit effector phase during tumor killing in vitro and in Winn assay, but enhanced tumor suppression in the established tumor model.

The use of retroviral vectors to transduce chimeric immune receptors into primary human lymphocytes has been limited by the low gene transfer efficiency when viral supernatant infections were carried out. Transfer rates into primary human T cells using amphotropic virus ranged from 1 to 12%. (Bunnell, 1995 #4550) Several strategies were explored to increase the transduction rates to 20-50%. These include: (1) using gibbon ape leukemia virus (GaLV strain SEATO) pseudotyped virions, (Miller, 1991 #3388; Lam, 1996 #4553; Krause, 1998 #3956) (2) coculturing producer and target cells, (Bonini, 1997 #4716) where the clinical safety was of some concern, (3) using phosphate depletion followed by centrifugation and incubation at 32° C., (Bunnell, 1995 #4550) (4) adding fibronectin CH296 to enhance virus/lymphocyte interactions. (Pollok, 1998 #4506) More recently, Eshhar et al described a dicistronic construct consisting of scFv-CD28-γ and green fluorescent protein (GFP), where the latter was used to monitor gene transduction and to enrich producer line. (Eshhar, 2001 #5665) In the inventor's study, we used anti-idiotypic antibody to select for high surface scFv-expressing producer lines with improved efficiency of gene transduction. More importantly, lymphocytes transduced by CD-28-ζ chimeric fusion receptors could survive and proliferate in the presence of the anti-idiotypic MoAb maintaining their monoclonality with respect to scFv expression, in both the CD4+ and CD8+ populations. These receptors mediated antigen-specific cytokine release and cytotoxicity that was non-MHC restricted. Whether NK cells (CD56+ population) could acquire similar abilities will need further studies, since CD28 signaling in these cells was only rarely documented. (Galea-Lauri, 1999 #5609) Using this anti-idiotypic antibody strategy with minor modifications, we have successfully extended these findings to the $G_{D2}$ antigen system (unpublished data). Recent studies have demonstrated the potential of CIR in retargeting EBV-specific cytotoxic T lymphocytes, (Rossig, 2002 #6479) a potential new source of effector cells that could persist and function long term after their transfer to cancer patients. We have also successfully transduced these scFv-CIR genes into EBV-specific cytotoxic T-cell populations (Koehne, 2000 #5893) to permit their in vitro clonal expansion of $10^6$-fold in 5 months (unpublished data).

The advantage of using anti-idiotypic antibody for affinity purification and for clonal expansion of gene-modified lymphocytes are many fold. Being immunoglobulins, their structure, stability, biochemistry are generally known. This is in contrast to natural antigens where each individual system has its unique and often difficult-to-predict properties. As surrogate antigens, anti-idiotypic MoAb are ideal for standardization and quality control, especially for initial clinical investigations of carbohydrate antigens or when the nature of the antigen is not fully understood. To prepare polyclonal CTLs specific for a tumor target, lymphocytes have to be pulsed periodically in vitro with the tumor cells. (Koehne, 2000 #5893) The possibility of tumor contamination raises safety and quality control issues. More importantly, TCR ligation usually leads to activation-induced cell death. (Lenardo, 1999 #6439; Beecham, 2000 #6440) In CIR technology, scFv-CD28-ζ and scFv-CD28-γ constructs recruit costimulation to sustain T-cell survival. (Alvarez-Vallina, 1996 #4698; Beecham, 2000 #6440; Maher, 2002 #6433; Eshhar, 2001 #5665; Haynes, 2002 #6477) In our studies, anti-idiotypic antibodies stimulated T-cell proliferation and survival. Another advantage of anti-idiotypic MoAb is its ability to mark the clonal population of target-specific lymphocytes. Although tetramers can mark TCR and T-cell clones, identity of the peptide antigen is required and tetramer technology is not widely available. Furthermore, anti-idiotypic MoAb can mark T-cell clones in vivo when radiolabeled, an option not yet possible with tetramers. Finally, the potential of anti-idiotypic MoAb to activate transduced lymphocytes in vivo is appealing, especially when tumor cells are poorly immunogenic, or when they are scarcely distributed. The observations of the inhibitory effect of anti-idiotype in the Winn assay were consistent with their in vitro inhibitory effects during the effector phase. However, in the established tumor model, anti-idiotype was able to enhance tumor suppression. Given its ability to sustain CIR-modified T-cell growth in vitro, a likely explanation was a similar supportive function in vivo in the established tumor model. One could speculate that anti-idiotype might also enhance the homing properties of these gene-modified T-cells. Clearly, a better understanding of in vivo homing properties and proliferative capacity of transduced cells in the presence or absence of anti-idiotype will be needed.

Previous studies suggest that the choice of the appropriate spacer (between scFv and signaling molecule), transmembrane domain and the signaling molecules were important. (Patel, 1999 #4695) That 8H9scFv-modified T-cells survive and proliferate in the presence of specific anti-idiotype and kill antigen-positive tumor cells argue strongly that the CD28 trans-membrane domain in this CIR design does not require a CD8 hinge, permitting effective interaction with soluble as well as cell-bound antigens. These results agreed with those recently reported by Maher et al. (Maher, 2002 #6433) It is of interest that in the absence of anti-CD3/CD28 antibody activation, gene-modified lymphocytes had consistent survival advantage during the first 3 weeks in culture, even without anti-idiotype. Since these fusion proteins can homodimerize, (Krause, 1998 #3956; Maher, 2002 #6433) signaling through spontaneous oligomerization may have provided initial survival advantage on gene-modified lymphocytes, although growth could not be sustained unless anti-idiotype is provided. Although the total increase in T cell number is comparable to anti-CD3/CD28 mediated in vitro expansion (Maus, 2002 #6438) the rate of increase is slower (2 to 3-fold), with significant cell loss during the first 3 weeks. It is possible that the transduction protocol can be improved to reduce direct toxicity from the viral supernatant. Signaling may also be improved by the addition of a hinge or the adoption of other trans-membrane domains. (Fitzer-Attas, 1998 #5955; Patel, 1999 #4695; Jensen, 1998 #4699) Moreover, using domains or molecules (wild type or genetically modified) further downstream in the T-cell activation pathway might potentially increase signaling, or even overcome the T-cell defects commonly found in cancer patients. (Eshhar, 1998 #5952)

The choice of tumor system and antigen target will likely determine the clinical success of CIR strategy. Primary lymphoid tumors such as B-cell lymphomas have distinct attributes. T-cells have an innate tropism to lymphoid tissues. These tumors also have unique tumor antigens with homogeneous expression that do not modulate from the cell surface (e.g. CD20). Furthermore, these B-cell tumors express costimulatory molecules. (Jensen, 1998 #4699) In contrast, most solid tumors lack these attributes. However, metastatic cancers in lymph nodes, blood and bone marrow are unique compartments where CIR technology may be applicable. Depending on the compartment, targeting of T-cells may require different chemokine receptors or adhesion molecules. For example, while L-selectin is required for homing to lymphoid organs, its role for trafficking to other metastatic organs such as marrow is less well defined. The precise evaluation of the quantity and persistence of these cells in vivo, as well as their distribution and function within tissues is likely to be critical. (Yee, 2001 #5674; Ma, 2002 #6437) In studies of T-cell therapy, this is of particular importance since many infused cells will undergo activation-induced death in vivo, (Lenardo, 1999 #6439; Beecham, 2000 #6440; Xiaoning, 1999 #5677) or immune elimination of gene-modified cells may occur, especially following repeated injections. (Riddell, 1996 #5963) The development of sensitive, accurate and reproducible methods to quantify gene-marked cells in peripheral blood and tissues are essential for defining the long-term fate of adoptively-transferred cells. While PCR and quantitative RT-PCR methods are ideal for studying tissues extracts, anti-idiotypic MoAb will provide useful a tool to enumerate individual scFv-positive cells in blood, marrow and tumor. In addition, noninvasive imaging methods using radiolabeled anti-idiotypic MoAb may also be possible. Similar to the marker gene HSV-tk that allows cells to be tracked and quantified by the substrate $^{131}$I-FIAU or $^{124}$I-FIAU, (Koehne, 2000 #5631) anti-idiotypic MoAb labeled with either $^{121}$I or $^{124}$I can also take advantage of instrumentation and software developed for SPECT and PET/microPET imaging, respectively. These tools can provide unprecedented precision and dynamic information on cell traffic in patient trials.

Retroviral vector MSCV carrying the gene for either 8HscFv-CD28, 8HscFv-CD28-ζ, or 5F11-scFv-CD28-ζ was transfected into packaging lines PG13 or GP+envAm12. The producer lines were then subcloned, affinity purified or FAC-sorted as detailed in Materials and Methods. The producer lines were analyzed for scFv expression by flow cytometry on day 4 after gene transduction.

Third Series of Experiments

ScFv-Modified Lymphocytes for Tumor Targeting

The plasticity of adult stem cells offers great promise in cell-based therapies. Hematopoietic stem cells give rise to all blood cells and have been used to treat serious blood disorders, malignant disease, and inherited diseases. These cells can differentiate into cardiac muscle cells, vascular cells, lung epithelia, neural cells, glial cells and other cell lineages. Developing tools to study both adult and embryonic stem trafficking in cellular therapies will provide a critical understanding of the real potentials and limitations of these approaches. While technical difficulties in gene modification of human stem cells have yet to be overcome, the human lymphocyte is a useful model to explore various in vivo imaging receptors, their targeting capacity, as well as the molecular biology and biochemistry of trace labeling methods.

Antibody-based targeting exploits the molecular specificity of the immune system. Utilizing single chain v-fragment (scFv) derived from monoclonal antibodies, chimeric immune receptors (CIR) can now be permanently transduced into primary human T-cells to redirect them to the specific antigen. In the last grant period we developed a technology based on anti-idiotypic antibodies to improve the rapid cloning of efficient producer lines for gene transduction. Using anti-idiotypic antibody as antigen surrogates, the propagation and expansion of these CIR-modified T-cells in vitro is highly reproducible. In this competitive renewal, we propose to compare the three imaging genes HSV1-tk, hNIS, and somatostatin receptor type 2 (SSTR2) to study T-cell trafficking. We will take advantage of the large experience in somatostatin receptors and ligands, plus the recent development of $^{68}$Ga for PET dosimetry studies. We will determine the biologic parameters that determine labeling of these cells, the radiobiological consequences, the minimum number of cells that can be detected at tumor sites, as well as the validation of quantitative methods of measurement models. We plan to test the hypothesis that substantial improvements in T-cell targeting efficiency is possible if CD4+ T-cells can be pretargeted to the tumor site, and if professional killer cells are used. The availability of a high-resolution animal scanner, the MSKCC MicroPET, plus the animal micro-CT will facilitate these studies. We will also benefit from prior developments under related DOE grants, which include 1) practical methods for production of $^{68}$Ga and $^{124}$I; 2) the quantitative PET imaging of positron-emitting radionuclides with complex spectra, such as $^{68}$Ga and $^{124}$I; and 3) a method for highly selective labeling of genetically modified tumor-specific immune cells, using the positron labeled tracer $^{124}$I-fluoroiodo-arabinosyl-uridine (FIAU).

Objectives

Although cell-therapy using stem cells and lymphocytes have great clinical potentials, their trafficking patterns and integration into tissues especially in real-time are not well understood. Noninvasive methods to help fill this knowledge gap remains a critical priority. Human T-lymphocytes are potent vehicles in tumor targeting. Retroviral vectors can permanently gene-modify their cell-surface receptors to target to specific tissues. As the sophisticated homing biology of T-lymphocytes becomes elucidated, clinical application of adoptive cell therapy has gained wider attention. We used scFv gene-modified T-lymphocyte as a cell-therapy model to study the pharmacokinetics of their survival and proliferation ex-vivo and in vivo after reinfusion. In the last grant period, we succeeded in using anti-idiotypic strategy to optimize gene transfer, survival and proliferation of T-cells ex vivo. We have shown that these cells can target to tumor sites to achieve tumor control in xenograft models. We propose to use somatostatin receptor type 2 (SSTR2) to study cellular biodistribution, and compare with HSV1-tk and sodium iodide transporter (hNIS). We will take advantage of recent advances in quantitative PET using $^{68}$Ga and $^{124}$I. We propose to test the hypothesis that successful pretargeting of T-cell subpopulation can recruit other lymphoid populations to improve homing to the target antigen and that using preprogrammed professional killer cells can further improve targeting efficiency.

Specific Aim 1: Comparison of marker genes for lymphoid cells in ex vivo and in vivo labeling
1.1 HSV1-tk
1.2 Somatostatin receptor subtype 2 (SSTR2)
1.3 Sodium iodide symporter Specific Aim 2: Pretargeting of CD4+ T-cells to improve adoptive cell therapy Specific Aim 3: Improving tumor homing and tumor cytotoxicity by using professional T-lymphocytes (CTL) and NK92 for CIR gene-modification
3.1 Cloned killer cell line
3.2 Professional cytotoxic T-lymphocytes (CTL)

Importance of the Research

The study of stem cell biology in vivo can potentially broaden our understanding of human cardiovascular, lung, blood, or neural development. The homing, proliferation and differentiation of stem cells in vivo are not fully understood and are likely to be influenced by the microenvironment. Studies of stem cell homing to sites of tissue injury or specific tissue or organ sites, and the mechanisms underlying the homing process will provide important information if stem cell therapy is to be successfully exploited for human diseases. Stem cell homing research can benefit from tools optimized for studying T-cell targeting to human tumors. We chose scFv-chimeric immune receptor directed at solid tumors to explore T-cell trafficking behavior, and propose noninvasive methods to track them in vivo.

Antigen-specific T-cells have been successfully used in adoptive therapies in patients for viral infections and cancer. These pioneering works have refined the practical issues of T-cell isolation, cloning, expansion and reinfusion. Adoptively transferred donor-derived Epstein-Bar virus (EBV) specific CTL can effectively eliminate B-cell proliferative disorders in the post-transplant period, a dramatic proof of principle for both efficacy and safety. After a 2-3 log expansion within the first month of infusion, these CTLs can be shown to survive for months, a property probably important for their in vivo efficacy. Successes in this EBV-lymphoma model is due to: (1) high CTL clonal frequency, characteristic of pathogen-based memory, (2) exquisite specificity to a viral antigen, (3) high levels of MHC and costimulator expression in lymphomas, and (4) innate ability of T-cells to home to lymphoid organs. Using retroviral vector gene transfers, it is now possible to modify durably the genetic makeup of T-lymphocytes. Targeting them to tumors is an enticing strategy since they can proliferate and expand clonally, potentially amplifying the anti-tumor response, as well the tumor to nontumor ratio of the delivered entity (either cells, cell-associated protein, secreted protein or viruses).

Using anti-idiotypic reagents, scFv chimeric immune receptors (CIR) consisting of scFv-CD28-ζ-chain have been transduced into primary human T-cells to produce readily expandable, long-lived and efficient clonal killer cell populations. Such CIRs genes joining tumor-selective ScFv to T-cell signal transduction molecules bypass MHC requirement while coupling antigen-specific tumor recognition with T-cell activation/survival. In this proposal we hypothesize that tumor targeting can be substantially improved if (1) CD4+ T cells can be successfully targeted first to recruit inflammatory populations including CD8+ T-lymphocytes and natural killer cells, and (2) the anti-tumor effect can be increased by employing preprogrammed professional killer T-cells. We propose to study the trafficking of whole or separated T-cell subpopulations in vivo after gene marking with human somatostatin receptor type 2 (SSTR2), human sodium iodide transporter (hNIS) or HSV1-tk. These lymphocytes can be imaged with [$^{66/67/68}$Ga]-DOTA-DPhe$^1$-Tyr$^3$-octreotide (DOTA-TOC), free $^{131}$I and $^{131}$I-labeled 2'-fluoro-2'-deoxy-1-b-D-arabinofuransyl-5-iodo-uracil ($^{131}$I-FIAU), respectively. Lymphocyte biodistribution and clonal expansion in vivo will be measured by positron emission tomography (PET) using [$^{66/68}$Ga]-DOTATOC, $^{124}$I and $^{124}$I-FIAU for the respective imaging genes. Using professional cytotoxic T-cells and cloned killer line NK92 instead of naïve T-cells for CIR gene transduction, we envision a substantial improvement in the efficiency of gene-modified T-cells by virtue of their preprogramming for tumor cytotoxicity, since they have been selected for their repertoire of lytic enzymes, death inducing peptides and adhesion molecules.

Background and Significance

Despite dose-intensive use of chemotherapy and radiotherapy, metastatic solid tumors have a dismal prognosis with cure rates of <20%.[1-3] Our inability to deliver specific therapy to minimal residual disease (MRD) compromises patient's chance of long-term cure.

Single chain Fv. The ability to condense the binding site by genetic fusions of variable region immunoglobulin genes to form scFv has greatly expanded the potential and development of antibody-based targeted therapies.[4-7] Using phage display libraries, scFv can now be cloned from cDNA libraries derived from rodents, immunized volunteers, or patients.[8-11] Construction of the scFv is the critical first step in the synthesis of various fusion proteins, including scFv-cytokine,[12] scFv-streptavidin,[13] scFv-enzyme,[14] scFv-toxins,[15] bispecific scFv (diabodies),[16] bispecific chelating scFv,[17] scFv-Ig,[12] tetravalent scFv,[16,18] and scFv-retargeted T-cells.[19]

Targeting lymphocytes to tumors. Using retroviral vector gene transfers, it is now possible to modify the genetic makeup of a cell permanently. Targeting lymphocytes to tumors is an attractive strategy. Lymphocytes execute complex tasks that antibodies are unable to perform, by communicating with and recruiting other inflammatory/immune cells or initiating tumor apoptosis. More importantly, they can proliferate and expand clonally. This latter property can potentially amplify the anti-tumor response, the tumor to nontumor ratio of the delivered entity (either cells, cell-associated protein, secreted protein or viruses), for both cancer imaging as well as therapy. Antigen-specific T-cells have been successfully used in adoptive therapies in patients for viral infections and cancer.[20-24] These pioneering work have refined the practical issues of T-cell isolation, cloning, expansion and reinfusion. Adoptively transferred donor-derived Epstein-Bar virus (EBV) specific CTL can effectively eliminate B-cell proliferative disorders in the post-transplant period, a dramatic proof of principle for both efficacy and relative safety.[22,23,25] After a 2-3 log expansion within the first month of infusion, these CTLs can be shown to survive for up to 18 months.[22,26] This success in the EBV-lymphoma model was due to: (1) high CTL clonal frequency, characteristic of pathogen-based memory, (2) exquisite specificity to a viral antigen, (3) high levels of MHC and costimulator expression in lymphomas, and (4) innate ability of T-cells to home to lymphoid organs.

Tools for tracking T-lymphocyte homing and their clonal expansion are limited. Previous models of lymphocyte homing have utilized lymphokine activated killer lymphocytes (LAK) or tumor infiltrating lymphocytes (TIL). In animal models, they generally showed tumor-specific localization. Although short-term labeling with chromium ($^{51}Cr$) is routine for isotope release cytotoxicity assays, it failed when applied to WBC trafficking studies. Attempts to incorporate radiolabeled metabolites and metabolite analogs (including 2-fluororo-deoxyglucose (FDG), amino acids, and nucleotides,[27,28] to radioiodinate cell membrane lipids/proteins, to induce phagocytosis of $^{99m}Tc$- or $^{111}In$-labeled colloids,[29,30] to trap intracellular radioactive divalent cations (e.g. $^{55}Co$ and $^{57}Co$),[31] or to tag with radiolabeled MoAb,[32-34] have met with limited success. Although $^{111}In$-labeled WBCs are routinely used to detect sites of infection and inflammation,[35] and in research studies of white cell homing properties,[36] high specific activity can interfere with lymphocyte functions possibly accounting for the low % ID/gm in recent studies of tumor-sensitized lymphocytes,[37] or TIL[38] cells. More importantly, $^{111}In$ labeling is currently only possible ex vivo. No imaging agent is available to study T-cell kinetics and biodistribution over an extended period of time.

There were several limitations in these early studies of lymphocyte imaging. Only a small proportion of cells are actually labeled. In the case of $^{99m}Tc$, its relatively short physical half-life (6 hr) limits imaging to less than 1 day post-injection. More seriously, these labeling methods are antigen non-specific; i.e. all cells exposed to the labeling agent are labeled regardless of their ability to bind to the tumor target. That may partly explain the suboptimal targeting of <0.02% injected cell dose per gram. The CTL precursor frequency against human tumors (e.g. melanoma) in peripheral blood mononuclear cells (PBMC) even after in vitro stimulation with IL-2/IL4 is generally low (0.1% to 0.0030).[39] In EBV-lymphoma, unstimulated peripheral blood CTL precursor frequency is less than 0.05% and is ineffective until in vitro EBV-restimulation to 0.8-4%.[40] The low CTL precursor frequency may account for many of the past failures in the studies of T-lymphocyte homing to tumors. Increasing the level of radiolabeling has limited success since more than 20 uCi $^{111}In/10^8$ cells is known to damage white cell functions.[41]

T-bodies can redirect lymphocyte against human tumors. Adoptive cell therapy using ex vivo expanded tumor-selective T-cells can effect dramatic remissions of virally induced malignancies, a process critically dependent on clonal frequency, where rapid exponential expansion of specific CTL is required.[23,25] T-cells proliferate when activated (e.g. anti-CD3). However, apoptosis occurs unless a costimulatory signal (e.g. anti-CD28) is present.[42] However, human tumor targets often lack costimulatory molecules (e.g. CD80), or overstimulate inhibitory receptors (e.g. CTL4) such that the CD28 pathway is derailed. In addition, many tumors down-regulate major histocompatibility complex (MHC) molecules to escape engagement by the T-cell receptor (TCR). Through genetic engineering, chimeric immune receptors (CIR) linking tumor-selective scFv to T-cell signal transduction molecules (e.g. TCR-ζ chain and CD28) will activate lymphocytes following tumor recognition, triggering the production of cytokines and tumor lysis.[19,43-49] T-cell can also be genetically engineered to secrete cytotoxic cytokines,[50] toxins,[51] or to metabolize prodrugs.[52,53] Genetically engineered T cells for adoptive immunotherapy of cancer is gaining wider attention. To date, clinical experience with gene-modified T cells has been limited, and most studies are unpublished (Table 1).[49] Although preclinical models generally utilized CD8+ CTLs, most clinical trials are utilizing unseparated T cells, preselected with co-expressed drug marker, or administered in bulk without selection to avoid targeting of microbial drug resistance genes. Most of these infusions have been relatively well-tolerated.

TABLE 1

Clinical trials using T-cells gene modified with CIR[49]

| Date | Phase | Disease | Antigen | Structure | Location | Investigator |
|---|---|---|---|---|---|---|
| 1995 | I | HIV | gp120 | CD4-ζ | NIH | Walker |
| 1996 | I | Ovarian CA | FBP | sFv-γ | NCI | Hwu |
| 1997-1998 | II | HIV | gp120 | CD4-ζ | Multi | Hege |
| 1997 | I | AdenoCA | TAG72 | sFv-ζ | Stanford | Hege |
| 1998 | I | AdenoCA | CEA | sFv-ζ | Harvard | Junghans |
| 2000 | I | Lymphoma | CD19 | sFv-ζ | City of Hope | Jensen |
| 2001 | I | Neuroblastoma | L1 | sFv-ζ | City of Hope | Jensen |
| 2002 | I | Renalcell | CAG250 | sFv-ζ | den Hoed CC | Bolhuis |
| 2002 | I | Melanoma | GD3 | sFv-ζ | Harvard | Junghans |

However, significant technologic gaps remain: (1) Gene transduction into primary human lymphocytes is inefficient, (2) Antigen specific T-cells cannot be easily enriched and expanded, (3) Optimal T-cell activation may require multiple signals, and (4) Demonstration of anti-tumor effect of these human T-cells in established tumor models has been difficult and so far unsuccessful in patients.[49] T-cell activation requires two simultaneous signals,[54] one signal provided through the TCR[55] and a second one is a costimulatory signal.[56] T-cells get their second signal from their CD28 molecules which recognize B7 on APCs and tumor cells, stimulating IL-2 production; otherwise apoptosis or anergy will occur in response to the TCR signal alone.[56] Primary T-cells transduced with the anti-GD2 scFv-ζ-chain or scFv-γ-chain CIRs were able to kill antigen-positive tumors selectively.[48] However, cell cultures could not be maintained for longer than 8 weeks even upon stimulation with antigen-positive tumor cells. In addition, T-cell function when measured by interferon-γ release decreased substantially during in vitro culture to 25% over 2 weeks. The inability of Fv-ζ receptors alone to activate resting T cells was demonstrated in a transgenic mouse model.[57] On the other hand, when an anti-tumor scFv-CD28 CIR was used,[58] a functional co-stimulatory signal was achieved. CIR with multidomains was recently described, where the intracellular domain of CD28 was ligated to the 5' end of TCR-ζ chain and introduced into Jurkat cells and primary human lymphocytes, with the expected "two signals" when scFv was triggered by tumor cells.[59,60] IL-2 production was 20 times more than CIR with ζ-chain only. Primary mouse CD8+ T lymphocytes expressing the scFv-CD28-ζ receptor secreted Tc1 cytokines, induced T-cell proliferation, and inhibited established tumor growth and metastasis in vivo, a process shown to be critically dependent on IFN-γ secretion.[61] Not all T-cell mediated immune responses are CD28-dependent, and in humans about 50% of CD8+ T cells are CD28-negative.[56,62] During CD28 costimulation, while CD4+ cells responded with sustained proliferation, CD8+ T-cells grew for a limited period only accompanied by an increase in apoptosis.[63] Other costimulatory molecules include members of the TNFR superfamily,[64,65] CD30[66] and OX40[67] for Th2, as well as CD27[68] and 4-1BB for Th1.[69] It is possible that while chimeric receptors containing CD28 will enhance CD4+ T-cell proliferation, those incorporating costimulatory molecules such as 4-1BB could enhance CD8+ T cell and other subpopulations to expand in vitro and possibly in vivo.

Progress Report

CIR gene modified professional killer cells: CTL and NK92 NK92, CD56+ cell line established from the peripheral blood of a 50-year-old male with rapidly-progressing non-Hodgkin's lymphoma (large granular lymphocytic) whose marrow was diffusely infiltrated with large granular lymphocytes (LGL),[87] kills a broad spectrum of leukemia-lymphoma and virally infected cell lines in vitro.[88] Its remarkable tumor cytotoxicity is probably due to its unique repertoire of activating NK receptors (NKp30, NKp46, 2B4, NKGD, E, CD28) with few inhibitory receptors (NKGA/B, low levels of KIR2DL4, ILT-2) commonly expressed on normal NK cells (Table 4).[89] In addition, NK92 expresses high levels of molecules involved in the perforin-granzyme cytolytic pathway as well as additional cytotoxic effector molecules including tumor necrosis factor (TNF)-superfamily members FasL, TRAIL, TWEAK, TNF-alpha, indicating the ability to kill via alternative mechanisms. NK92 cells can be expanded in vitro with IL-2 with a doubling time of 24 to 36 h. IL2 was also successfully transduced into NK92 which then proliferate independently of IL-2 for >5 months, with concurrent increase in both in vitro and in vivo cytotoxicity.[90] NK92 has been used for ex vivo purging of malignant BCR-ABL-positive CD34+ progenitor cells from stem cell autografts of CML patients.[91] In phase I clinical trials, children and adults with late stage malignancies have received repeated irradiated NK92 transfusions up to $9 \times 10^9$ cell dose without adverse reactions.[88] Patients had no evidence of anti-NK92 immune response. However, NK92's lytic activity against solid tumor targets is less predictable. 8H9-scFv-CD28-ζ has also been transduced into NK92 cells, and the high expressors sorted and cloned using anti-idiotype strategy as described for primary T-lymphocytes. These gene-modified NK92 cells can efficiently kill an expanded spectrum of tumor lines in vitro as well as suppressing human tumor xenografts in vivo.

Gene expression profile of CIR-modified T-cells and NK92 An analysis of inflammatory chemokines, cytokines and receptors, as well as interleukins and receptors gene expression among CIR-modified NK92 as well as CIR-modified T-cells (cultured for 70 days, 99.7% scFv-positive, 50% CD4+ and 50% CD8+, harvested during their exponential growth) was undertaken. The GEArray Q series cDNA expression arrays (SuperArray, Bethesda, Md.) were used for these assays. In brief, cDNA probes using 5 ug each of T cell RNA from CIR-gene modified blood lymphocytes, versus fresh and cultured control lymphocytes, were synthesized with biotin-16-UTP. Hybridization at 60° C. was carried out in a hybridization chamber with constant rotation overnight. After several washes, chemiluminescent detection was performed at room temperature. A 1:10,000 dilution of alkaline phosphatase-conjugated streptavidin was placed on the membrane after a 40 minute blocking step. After several washes, CDP-Star chemiluminescent substrate was added. The membrane was placed between two transparencies, and developed on X-ray film for 10 seconds. Data analysis of the image was based on SuperArray software (Eisen Lab, LBNL, UCB, CA) and GEArray Analyzer (SuperArray). Four gene chips were used: human inflammatory cytokine and receptor, human interleukin and receptor, human extracellular matrix and adhesion molecules, human cytokines and receptors. Experiments were repeated at least once. Gene expression values were normalized to that of GAPDH and values from multiple chips were averaged. CIR modified T-lymphocytes displayed remarkably similar profiles of interleukin plus receptor (Tables 5 and 6, minus=negative, W=weak, Y=strong expression) and chemokine plus receptor (Tables 7 and 8) as compared to cultured T-lymphocytes without CIR gene modification, consistent with the expectation that CIR gene transduction did not substantially change the phenotypes necessary for their immune functions. Furthermore, both gene-modified T and NK92 cells expressed common chemokines including RANTES, and a broad spectrum of interleukins (e.g. IL4, table 4) and interleukin receptors (e.g. IL15R, table 6) with potential importance in amplifying the anti-tumor response. In contrast to low/absent CCR7 (thereby allowing T-cell to recirculate instead of docking in lymph nodes), CCR5 highly expressed for both 8H9s-scFv-CD28-ζ modified T and NK92 cells (Table 8). Since IL7 receptor was not detected among either T-cells or NK92, while IL15 receptor was expressed by both, IL15 may be useful for enhancing the survival of CD8+ T-cells both in vitro and in vivo. Also of note was the low level or absence of IL-2 and IFN-γ when the cells were harvested while off anti-idiotypic antibody.

Transduction of HSV1-tk into primary human T-cells HSV1-tk is a therapeutic gene, a marker gene, as well as a suicide gene. In order to examine the migration of genetically altered antigen-specific T lymphocytes to tumors after adoptive transfer in vivo, we exploited the capacity of transduced T cells expressing HSV-TK to selectively phosphorylate and trap in cells and incorporate into DNA radiolabeled thymidine analog 2'-fluoro-2' deoxy-1-D-arabinofuransyl-5-iodouracil (FIAU) (FIG. 7). Gamma camera images and autoradiographs showed selective tumor localization of $^{131}$I-FIAU-labeled HSV1-tk-transduced EBV-specific, HLA-matched allogeneic donor T cells in preclinical models, achieving 1-2% injected per gram of tumor, and tumor-to-normal tissue activity ratio >100:1. In contrast to conventional cell labeling methods which are non-selective; FIAU labeled only those lymphocytes with the HSV1-tk transgene, yielding a highly purified and highly target-specific lymphocyte population. In addition, HSV1-tk transduced primary human PBLs were sensitive to ganciclovir (0.01-0.1 uM) in vitro and in preclinical models (20 mg/kg bid×7 days). The ability of EBV-specific HSV1-tk transduced T-cells to home and kill subcutaneous EBV lymphoma xenografts was completely removed by ganciclovir treatment, thus allowing these gene-modified T-cells to be safely removed when necessary.

The cell-level dosimetry of lymphocytes labeled by incubation ex vivo with radioiodinated FIAU was critical since [$^{131}$I]-FIAU could interfere with T cell function. In this model, the FIAU uptake (i.e. labeling) of the lymphocytes is expressed as the accumulation ratio (AR=cpm per gram of cells/cpm per ml of medium). The absorbed dose to the lymphocyte nucleus to reference (r) time $T_r$, $D_n(T_r)$, is calculated as the sum of the medium (m)-to-nucleus (n) dose, $D(n \leftarrow m)$, and the nucleus-to-nucleus dose, $D(n \leftarrow n)$. $D(n \leftarrow m)$ was equated with the mean non-penetrating (np) radiation (i.e. β) dose, $D_{np}$, from radioiodine in the medium (assuming the presence of the widely dispersed unit density cells would not significantly perturb the electron flux and therefore the dose from radioiodine otherwise uniformly distributed in the medium) and $D(n \leftarrow n)$ was calculated assuming instantaneous cell uptake of [$^{131}$I]-FIAU and using the recently published MIRD cell S factors.[92]

$$D_n(T_r) = D(n \leftarrow m) + D(n \leftarrow n) \approx D_{np} + D(n \leftarrow n)$$
$$= \Delta_{np} \cdot T^*[A]_m/\rho + S(n \leftarrow n) \cdot [A]_m \cdot M_c \cdot$$
$$\sum_{i=1}^{r} AR_i \cdot \int_{T_i}^{T_{i+1}} e^{-\lambda_p t}/\rho$$

where $\Delta_{np} = 0.405$ gm-rad/$\mu$Ci-hr for $^{131}I$, $T^* =$ time of incubation of the cells with $^{131}I$-$FIAU \approx 2$ hr, $T_i =$ time from the start of the incubation in the [$^{131}I$]-$FIAU$-containing medium, $T_r =$ reference time from the start of the incubation in the [$^{131}I$]-$FIAU$-containing medium for which the dose is calculated $\equiv 60$ hr (typical in vivo imaging time post-injection), $[A]_m =$ activity concentration in medium ($\mu$Ci/ml), $\rho =$ mass density $= 1$ gm/ml for both medium and cells, $S(n \leftarrow n) =$ the nucleus-to-nucleus $S$ factor (i.e. dose per unit cumulated activity $= 1.43 \times 10^{-7}$ rad/$\mu$Ci-hr for $^{131}I$ $AR_i =$ accumulation ratio at the time $T_i$ from the start of the incubation in the [$^{131}I$]-$FIAU$-containing medium $M_c =$ mass of cell $\equiv 1 \times 10^{-9}$ gm/cell as measured for $T$ lymphocytes $\lambda_p =$ the physcial decay constant of radioiodine $= 0.0036$ hr$^{-1}$ for $^{131}I$.

Based on the forgoing dosimetry model and as presented graphically in the FIG. 15, the lymphocyte nucleus absorbed dose was calculated as a function of activity concentration in the medium and the accumulation ratio. To study the effect on T-cell function, [$^{131}$I]-labeled FIAU was incubated with HSV1-tk transduced T cells at 11 Ci/ml at 37° C. for 40 to 120 min in increasing activity concentrations of [$^{131}$I]-FIAU from 1.1 to 56 μCi/ml, washed and transferred to fresh ([$^{131}$I]-FIAU-free) medium for 72 hr, and then used in a 51Cr-release immune cytotoxicity assay (low effector:target cell ratio=5). There was no demonstrable diminution in immune function up to an absorbed dose (at the reference time of 60 hr) of 1,200 cGy. At greater doses (>1,900 cGy), there was a dose-dependent decrease in immune function.

Radioactive gallium labeled somatostatin analogue DOTA-DPhe$^1$-Tyr$^3$-octreotide (DOTATOC Table 9) for positron emission tomography imagine Radionuclide labeled somatostatin analogues selectively target somatostatin receptor (SSTR)-expressing tumors as a basis for diagnosis and treatment of these tumors. Recently, a DOTA-functionalized somatostatin analogue, DOTATOC has been developed. This compound has been shown to be superior to the other somatostatin analogues as indicated by its uniquely high tumor-to-nontumor tissue ratio. DOTATOC can be labeled with a variety of radiometals including gallium radioisotopes. Gallium-66 is a positron emitting radionuclide ($T_{1/2}$=9.5 hr; βy$^+$=56%) that can be produced in carrier free form by a low-beam energy cyclotron. SSTR targeting characteristics of $^{66}$Ga-DOTATOC were studied in nude mice implanted with AR42J rat pancreas tumor, and compared with $^{67}$Ga- and $^{68}$Ga-labeled DOTATOC. The labeling procedure gave labeling yield ranged from 85-95% and radiochemical and chemical purity was >95%. In-vitro competitive binding curves and in vivo competitive displacement studies with an excess of unlabeled peptide indicates that there is specific binding of the radioligand to SSTR. Animal biodistribution data and serial micro-PET™ images demonstrated rapid tumor uptake and rapid clearance from the blood and all tissues except kidney. Maximum % ID/g values for tumor were 10.0+0.7, 13.2+2.1 and 9.8+1.5 for $^{66}$Ga-, $^{67}$Ga-, and $^{68}$Ga-DOTATOC, respectively. Calculated tumor, kidney and bone marrow doses for $^{66}$Ga-DOTATOC based on biodistribution data were 178, 109 and 1.2 cGy/MBq, respectively. $^{68}$Ga labeled DOTATOC can be used for PET diagnosis and quantitative imaging-based dosimetry of SSTR positive tumors. $^{66}$Ga-DOTATOC may also be used in higher doses for ablation of these tumors. However, kidney is the critical organ for toxicity (tumor/kidney ratio=1.64).[93]

Background and Statement of Work

Specific Aim 1: Comparison of marker genes for lymphoid cells in ex vivo and in vivo labeling: HSV1-tk, Somatostatin receptor subtype 2 (SSTR2) and hNIS 1.1 Herpes Simplex virus I thymidine kinase (HSV1-tk), In vivo methods for monitoring gene-modified cells have exploited the sensitivity of gamma-camera (SPECT) or PET imaging to detect intravenous radiolabeled compounds that localize to the products of transferred genes. These genes include enzymes that metabolize drugs (Herpes Simplex Virus-1 thymidine-kinase [HSV1-tk]), transport drugs across cell membranes (sodium-iodide symporter [NIS]), and ligand-binding surface receptors (type 2 somatostatin receptor [SSTR2][94-96] and the type 2 dopamine receptor).[97,98] HSV1-tk gene transfer can be detected by both gamma and PET imaging using radiolabeled prodrugs (e.g. $^{124}$I-FIAU) that become entrapped in the cell after phosphorylation by the kinase [99-103] Given the limitations of in vitro radiochemical cell labeling, a marker gene that does not interfere with T-cell function is critical for biodistribution studies of adoptively transferred T-cells. Each of these three marker genes have their merits and disadvantages.

|  | HSV1-gk | SSTR2 | NIS |
|---|---|---|---|
| Human origin | N | Y | Y |
| Substrate availability | + | +++ | ++++ |
| Substrate safety record | ± | safe | safe |
| PET capability | Y | Y | Y |
| Suicide function | Y | N | N |
| Cellular retention | Y | Y | N |
| Distribution | cytoplasmic | membrane | membrane |

-continued

|  | HSV1-gk | SSTR2 | NIS |
|---|---|---|---|
| Tissue specificity | Y | tumors; some normal tissues | thyroid/ stomach/ salivary gland |

Key advantages of HSV1-tk include its suicide function and its specificity (i.e. not found in human solid tumors). However, there are several limitations: (1) To label HSV1-tk-gene modified lymphocytes in vivo may need high concentrations of FIAU is needed. The safety of iodine-labeled FIAU especially at high doses is unknown, while unlabeled FIAU itself has been linked to severe hepatic toxicity in clinical trials. (2) Iodine-labeled FIAU requires special and expensive radiochemistry, (3) Nuclear location of metabolized radiolabeled FIAU can damage cellular DNA, limiting the absolute amount of radioiodine per lymphocyte. (4) HSV1-tk is a foreign protein, potentially antigenic and allergenic. (5) HSV1-tk is an intracellular protein, the expression of which is hard to quantitate in live cells. (6) Suicide with ganciclovir requires cell division and can be compromised because of HSV1-tk gene deletions.[104]

1.2 Human type 2 somatostatin receptor (SSTR2) SSTR2[94-96] is a membrane receptor that can be imaged with radiolabeled peptide ligands including $^{99m}$Tc-P829 [Neo-Tect, Amersham Health, Princeton, N.J., FDA approved],[105] $^{188}$Rh-P829, $^{99m}$Tc-P2045, and $^{111}$In-octreotide [Mallinckrodt] which is FDA-approved for total body imaging. We chose SSTR2 because it has been used extensively in clinical imaging with readily available radiolabeled ligands. In addition, a number of optimization strategy has already been designed, including intravenous L-lysine to reduce renal uptake. There are 6 SSTRs: types 1, 2A and 2B, 3, 4, and 5, all belonging to the 7-transmembrane domain family of receptors associated with G-proteins. Human type 2 has high affinity for octreotide, types 1 and 4 have low affinity,[106,107] and types 3 and 5 have intermediate affinity.[108-110] Types 2A and 2B are alternate splice variants where type 2A has a longer intra-cytoplasmic carboxy terminus than type 2B. SSTR2 expression has been reported in human lymphoid and leukemia cell lines, human peripheral blood lymphocytes especially when activated with PHA.[111] SSTR2 is the dominant receptor subtype expressed by inflammatory cells including T-cells.[112] Somatostatin and its analogs specific for SSTR2 enhance adhesion of T-cells to fibronectn.[113] 111In-pentetreotide (octreotide) was used for predicting impending cardiac allograft rejection before endomyocardial biopsy becomes positive.[114] The inhibitory effect of somatostatin on lymphocyte proliferation[115] is mediated by SSTR-5.[116] When a panel of octreotide ligands were screened for their binding affinity and specificity (Table 9), Gallium labeled-DOTATOC was chosen for our studies because of its high affinity and specificity towards SSTR2 preferentially over SSTR5 which can interfere with the proliferation of gene-modified T lymphocytes.

1.3 Na$^+$/I$^-$ Symporter (NIS) Both rat and human NIS, a membrane-bound glycoprotein which is responsible for the thyroid gland's ability to concentrate iodide up to 40-fold with respect to plasma, was recently cloned,[117,118] and its genomic structure analyzed.[119] hNIS has 643 amino acid and a proposed secondary structure containing 13 transmembrane helices. NIS was upregulated with trans-retinoic acid in breast cancer cell line MCF7.[120] Prostate cell lines transfected with hNIS linked to a PSA promoter became sensitive to radioiodine therapy.[121,122], Adenovirus-mediated[123] or retrovirus-mediated[124] transfer of rat NIS into human carcinoma lines and human glioma cell lines[125] enabled rapid perchlorate-sensitive radioiodine uptake, in some cases to >200 fold. Xenografted tumors injected intratumorally with this adenovirus became iodine-avid accumulating 11% ID/gm. Prostate cancer (LNCaP) transfected ex vivo with the hNIS retained 25-30% of the total radioiodine with a biologic half-life of 45 h (30-60 h) and produced tumor shrinkage.[122] The slow efflux of iodide from NIS transduced cells can be partly explained by their lack of the efflux pump pendrin,[126,127] found exclusively in the thyroid but not other normal tissues.

Advantages and limitations of SSTR2 and hNIS to track T-cells are several fold. (1) Their radioligands are commercially available and inexpensive. (2) The safety and toxicities of the ligands are well known. (3) The bound ligands, unlike nucleotides, do not persist in DNA. (4) If transduced into T-cells, both hNIS and SSTR2 are human-derived and less likely to be antigenic or allergenic. (5) Clinical pharmacokinetics of the radioligands are well characterized, (6) SSTR2 and hNIS are surface proteins easily monitored with fluorescent or radiolabeled peptides or monoclonal antibodies, allowing high expressors to be potentially enriched by affinity column or flow cytometry. (7) Since it is naturally expressed by some activated T-lymphocytes, SSTR2 appears compatible with normal T-cell biology.

Neither NK92 nor CIR-gene modified T-cells expressed SSTR2 or showed spontaneous uptake of $^{111}$In-Octreotide; thus SSTR2 gene transduction is necessary for imaging purposes. Surface receptor SSTR2 versus enzyme HSV1-tk approach have recently been compared in vitro and in vivo. Although uptake was equally good in vitro, in vivo imaging with HSV1-tk appeared inferior to SSTR2.[96] We expect radiometal labeled peptides to be rapidly endocytosed following binding to SSTR2, and become trapped intracellularly, unlike radioiodine which is metabolized and released. One major disadvantage of SSTR2 is its presence in a large spectrum of neuroendocrine tumors; here T-cell trafficking and tumors may not be easily distinguishable. Nevertheless, most sarcomas[128] and high risk (in contrast to low risk) neuroblastoma[129] have low expression of SSTR2. hNIS has a clear advantage over SSTR2 since few tumors except thyroid and possibly breast cancers express this protein. Although NIS can be transfected into human cells to express functional protein, the cellular consequences of the ectopic ion channel or iodine accrual on the human lymphocytes are unknown. There is also the concern on the membrane trafficking of the symporter. Although the leader sequence in the pVector would enhance membrane localization of the transgene, the rate of symporter turnover could affect the amount of radioiodine uptake. The efflux of iodide and consequently the short cellular half life can also be a limitation, especially if repeated imaging studies are needed. Nevertheless, this is a surmountable issue since radioactive iodine can always be readministered. Ironically this efflux could be an advantage, since radioactive iodide is rapidly excreted and less likely to damage lymphocyte function. It is conceivable that if retention of the iodide is needed, NK92 line can first be transfected with thyroid peroxidase enzyme to ensure organification.[130] One unique advantage of HSV1-tk is its suicide function that kills transduced cells in the presence of ganciclovir. Nevertheless, hNIS-transduced lymphocytes can potentially be killed by high dose of $^{131}$I or $^{124}$I, as demonstrated in NIS-gene modified tumor cell lines[120,122-125] and the thyroid gland.

General Plan of Work:
Comparison of HSV1-tk, hNIS and SSTR2 in gene marking of cloned killer lymphocytes

| Marker Gene | Ligand or substrate | |
|---|---|---|
| | Gamma | PET |
| HSV1-tk | $^{131}$I-FIAU | $^{124}$I-FIAU |
| hNIS | $^{131}$I | $^{124}$I |
| SSTR2 | $^{111}$In- DOTATOC Or $^{67}$Ga-DOTATOC | $^{68}$Ga-DOTATOC |

NK92 is a cloned killer cell line with well established characteristics (see Progress Report). EGFP (green fluorescence protein) was previously transduced into these cell lines and cloned, now used as our indicator line. Gene transduction will be carried out in two separate steps. First we use pDisplay vector from Invitrogen (Carlsbad, Calif.) to transduce either the SSTR2 or hNIS into NK92 cells as previously described.[96] A light chain 5' Igκ leader sequence for membrane localization plus a hemagglutinin (HA) tag will be inserted upstream of the SSTR2 and hNIS genes.[131,132] A stop codon will also be introduced into the 3' end to prevent expression in addition to the carboxy-terminal tail of SSTR2 or hNIS.[132] Since the binding domain for somatostatin is in the carboxyl end of SSTR2 between domains III and VII, amino terminal tag is not expected to interfere with receptor internalization.[132] Full length SSTR2 cDNA (type A)[133] was obtained from Dr. S Dorosio, U. of Iowa. Full length hNIS cDNA (2335 bp) was kindly provided by Dr. S. Jhiang of Ohio State University, Columbus, Ohio. Using anti-HA antibody (pDisplay vector), high expressors will be selected by affinity chromatography or cell sorting, and cloned in vitro. HSV1-tk was previously successfully transduced into NK92 using a discistronic vector, and selected with NGF (low affinity receptor) (see Progress Report). We have shown that NK92 can undergo multiple gene transductions and cloned without loosing its in vitro growth and cytotoxicity properties.

Specific Methods:
Saturation binding studies with $^{66/67/68}$Ga-DOTATOC Fresh cell membrane suspension (50 ug) on ice in 10 mM HEPES (pH 7.6, 20 μg/mL bacitracin, 5 mM MgCl$_2$ pH 7.6) is mixed in triplicates with increasing concentrations of $^{67}$Ga-DOTATOC (5 pM-5 nM) either with or without 1 μM octreotide. The mixtures are placed on an orbital shaker for 45 minutes at room temperature before being diluted with 1 mL of ice cold saline buffer (150 mM NaCl, 10 mM Tris pH 7.4). The suspension is then rapidly (with vacuum) filtered over glass fibre filters (Whatman GF/C, presoaked in 1% BSA) and the tubes washed twice with ice cold saline (2×4 mL). The glass fiber filters were then removed before being counted with an automatic NaI(Tl) counter. For each data point, triplicates were performed. Specific binding is defined at the total binding minus the non-specific binding (i.e. in the presence of 1 μM octreotide). The data is then analyzed by saturation curve analysis. An analogous method was previously used to determine the binding affinity of DOTATOC for individual SSTRs expressed by transfected CHO cells (Table 9).

Kinetics of [$^{66/67/68}$Ga]-DOTATOC uptake and cellular dosimetry of indicator killer line NK92 SSTR2 gene modified lymphoid cells will be incubated in the presence of [$^{66/67/68}$Ga]-DOTATOC. Following incubation, cells will be washed twice with ice-cold medium and radioactivity measured in a γ-counter, and normalized to cell number. The human neuroblastoma cell line SKNSH transfected with hSSTR2 (kindly provided by Dr. S. Dorosio of U. of Iowa, IA) is used as a positive control. The time-dependent activity concentration in the cells will be calculated. To study cellular damage on NK92 or T-lymphocytes, cells are labeled by incubation for 2 hr with increasing radioligand concentrations, washed and transferred to fresh nonradioactive medium for 72 hr, and an aliquot tested in vitro for cytotoxicity in $^{51}$Cr-release (at low E:T ratio) and IFN-(production. The rest of the NK92 are grown in fresh medium for 3 days, and their cell viability and cell number assayed. We want to confirm our previous results that cellular viability and immune function are not affected at absorbed doses (at 60 hr) of <=1,200 cGy. In addition to checking for immune functions, we will also establish a dose response curve for the level of radioactivity uptake and inhibition of lymphocyte proliferative capacity in a standard MTT assay.

Internalization and shedding of [$^{66/67/68}$Ga]-DOTATOC following SSTR2 receptor binding Internalization studies will be carried out using a modification of previously published methods.[134] Following [$^{66/67/68}$Ga]-DOTATOC binding at 4° C. (on ice) and unbound ligands removed by washing, cells are incubated at 0° C. or 37° C. for various time periods. Free ligand in the supernatant and PBS wash are counted in a γ-counter. Remaining [$^{66/67/68}$Ga]-DOTATOC on the cell surface are acid stripped by incubation with a buffer containing 0.05 M glycine HCl and 0.05 M acetic acid (pH 2.8-3) and 150 mmol NaCl for 5 min at 0° C.[135] The fraction of internalized ligand is calculated from the remaining radioactivity divided by the initially bound radioactivity.

Total cpm=free+acid-stripped+internalized

Cell bound=acid-stripped+internalized

% internalized=100*internalized/total cpm

% cell bound=100*cell bound/total cpm

% free=100*free/total cpm $^{66/67/68}$Ga Labeling of DOTATOC$^{66}$Ga is produced by the cyclotron on site at Memorial Sloan-Kettering Cancer Center. $^{67}$Ga is commercially available. Five microliters of carrier-free $^{67}$Ga (930 mCi/mL, 0.05 M HCl) is added to 40 HL of 0.3 mM NH$_4$OAc (pH 7) and 4 μL of 1 mM DOTATOC. The reaction mixture is placed in a water bath at 100° C. for 15 minutes before a 1 μL portion is removed and diluted to 2 mL with 4 mM DTPA (pH 4.0). Fifty microliters of this solution is then analyzed by HPLC using C18 column (4 μm, 3.9×150 mm) and an eluant of 1.2 mL/min 20 mM NH$_4$OAc (pH 4), 0-60% acetonitrile gradient over 15 minutes. Typically incorporation rates are in excess of 99.5%.

$^{68}$Ga is eluted from a SnO$_2$ based $^{68}$Ga/$^{68}$Ge generator in 5 ml of 1 M HCl. The concentration of HCl is increased to 5 M and the solution extracted with 2×1.5 mL diisopropyl ether. The ether fractions are pooled and evaporated under a stream of nitrogen. The concentrated $^{68}$Ga (3-4 mCi) is then dissolved in 50 μl, of 0.3 M NH$_4$OAc and added to 3 μL of 1 mM DOTATOC. The mixture is heated at 100° C. before a 1 μL portion is removed and diluted to 1 mL with 4 mM DTPA (pH 4.0). The diluted solution is spotted onto two 10×1 cm ITLC-SG strips and developed in either 4 mM DTPA (pH 4.0) or 1 M NH$_4$OAC (pH7, 50% MeOH). In the pH4 TLC system the $^{68}$Ga-DOTATOC remains at the origin with any colloidal $^{68}$Ga(OH)$_3$ and $^{68}$Ga-DTPA migrates with the solvent front. In the pH7 system, colloidal $^{68}$Ga(OH)$_3$ remains at the origin and $^{68}$Ga-DOTATOC and $^{68}$Ga-DTPA move with the solvent front. Typically incorporation rates are in excess of 99.5%.

Kinetics of radioiodide uptake in NIS transfected cells and cellular dosimetry of NK92 hNIS Gene modified NK92 and T-lymphocytes will be incubated in the presence of carrier-free Na$^{125}$I (Amersham Pharmacia Biotech) and 10 µM NaI (to give a specific activity of 20 mCi/mmol), with or without 30 µM KClO$_4$. Following incubation, cells are washed twice with ice-cold medium and radioactivity measured in a γ-counter, and normalized to cell number. The rat thyroid cell line FRTL-5 (from ATCC) is used as a positive control. [$^{131}$I]-labeled labeled FIAU is incubated with HSV1-tk-transduced-NK92. The time-dependent activity concentration in the cells will be expressed as the accumulation ratio (see Progress Report). Next, the NK92 cells or lymphocytes are labeled by incubation for 2 hr with increasing radioligand concentrations, washed and transferred to fresh nonradioactive medium for 72 hr, and an aliquot then used in a $^{51}$Cr-release immune cytotoxicity assay (at low E:T ratio). Another aliquot will be allowed to propagate in fresh medium for 3 days, and their cell viability and cell number measured. We will confirm our previous results that cellular viability and immune function are not affected at absorbed dose (at 60 hr) of at least 1,200 cGy. Since iodide is not sequestered in the nucleus, we expect the maximum tolerated dose to be higher for hNIS, which should improve scintigraphic imaging in vivo. A dose response curve for cytotoxicity will be constructed.

Iodide efflux assay The dose-dependent release of activity from NK92 or lymphocytes will also be evaluated as a function of post-labeling time. At various time after the incubation of the effector cells in $^{131}$I containing medium and transferring to [$^{131}$I]-free medium, the activity remaining in the cells and leaking into the medium are assayed. The content of $^{131}$I in the supernatant is measured by γ-counter. After the last time point, the cells are extracted with 400 µl ethanol to count residual radioactivity. The rat cell line FRTL-5 is used as a positive control.

Western Blot analysis Postnuclear membrane fractions will be prepared and western blot analysis performed using a rabbit anti-SSTR2 antibody (BioTrend, Chemicals, Destin, Fla.), using a murine monoclonal anti-NIS antibody (kindly provided by Dr. J. Struck of Brahms, Berlin, Germany), or anti-HSV1-tk antibody (Dr. Tjuvajev, MSKCC, NY) and horseradish peroxidase-conjugated anti-mouse IgG (Jackson Research Laboratories), and signal visualized by chemiluminescence. Quantitative analysis is performed using the NIH IMAGE program (http://rsb.info.nih.gov/nih-image/).

FACS analysis Cells expressing the HA-tagged SSTR2 can be monitored with anti-HA antibody (12CA5, Boerhinger-Mannheim, Indianapolis, Ind., or HB-66, ATCC, Rockville, Md.) or rabbit anti-SSTR antibody (Santa Cruz Biotechnology, Santa Cruz, Calif.). Cells expressing SSTR2 are first reacted with specific antibody or IgG control, washed and then reacted with FITC-goat anti-rabbit (if primary antibody is rabbit) or FITC-goat anti-mouse (if primary antibody is mouse monoclonal) affinity purified antibody (Jackson). Propidium iodide (10 µg/ml) is used to mark damaged cells, and excluded from the analysis. SKNSH neuroblastoma cell line will be used as the positive control for SSTR2 expression. The fluorescence of 5000-10000 cells/tube is assayed using the FACSCalibur cytofluorometer (Becton Dickinson). Cells expressing HA tag can be monitored with anti-HA antibody. Alternatively, hNIS without HA can be monitored with the MoAb from Brahms, Germany.

Quantitative measurement of T-cells in tissue sections In order to determine quantitatively the number of lymphocytes trafficking to the tumor site, we plan to perform 2 kinds of experiments: (1) extracting single cells from tumors and (2) by radiotracer technique. Single cell suspensions are prepared from a known weight of tumor using collagenase enzyme mixtures. After ficoll-gradient to remove debris and dead cells, the number of gene-marked lymphocytes are quantitated by flow cytometry using EGFP (NK92 only), anti-idiotypic antibody and marker-gene specific antibodies: anti-HA (for SSTR2), anti-hNIS, and anti-NGFR(HSV1-tk) antibodies. To avoid collagenase/protease modification of surface proteins fresh frozen tissue sections will also be analyzed by direct fluorescence (EGFP, NK92), or indirect immunofluorescene using specific antibodies. The relationship between cell dose injected and the number of T-cells/gm of tumor will be determined. Quantitative autoradiography can also be performed although they need to be correlated with histology. For cells carrying HSV1-tk gene, they can be labeled with $^{131}$I-FIAU, or SSTR2 gene with $^{111}$In or $^{67}$Ga-DOTATOC, and hNIS labeled with $^{125}$ for radiotracer experiments.

Imaging and quantitative measurement of tumor infiltrating T-cells SCID mice xenografted with human tumors are injected i.p. with 2 ml of 0.9% NaI solution to block thyroid uptake of radioactive iodide. Gamma camera imaging and SPECT are performed with a dual-headed ADAC Genesys gamma camera (ADAC, Milpitas, Calif.) equipped with a HEHR collimator. Sequential images are obtained at 1, 4, 18-24 h after cell injection. PET images can provide highly accurate quantitation of radiolabeled cell distribution within the body. The PET protocol consists of scanning at 1, 4, 18 hr post infusion. For ex vivo labeling $^{66}$Ga-DOTAOTC (T–½=9.5 h) or $^{124}$1 can be used. For in vivo labeling, shorter half life isotope such as $^{68}$Ga (T–½=68 min) will also be tested. Images will be reconstructed and attenuation corrected. Transaxial and sagittal slices will be studied in order to ascertain the uniformity of the radiolabel distribution. With micro CT fusion, for each time point, the specific activity of isotope per volume plotted over time can be calculated. Time activity graphs will be decay corrected for isotope in order to obtain a biological clearance curve.

Cell labeling in vivo after homing to tumor sites To test the concept of imaging scFv-CIR modified lymphocytes, animals are treated with NaI i.p. to block the thyroid uptake. No-carrier-added $^{131}$I,$^{124}$I (for hNIS),$^{131}$I-FIAU or $^{124}$I-FIAU (for HSV1-tk) and $^{111}$In-DOTATOC or $^{66/67/68}$Ga-DOTATOC will be injected iv at 24 h, 48 h, or 72 h after T-cell injection, depending on when the maximal homing occurs from biodistribution experiments. Tumors in mice will be imaged by gamma (planar or SPECT) or PET where appropriate. Biodistribution studies at various time points will be done by tissue counting. Tissues will also be analyzed (direct and indirect fluorescence plus QAR.

Retroviral dicistronic construct Although imaging gene and CIR can be separately introduced into established killer lines like NK92, for primary human T-cells, both marker and CIR genes have to be transduced simultaneously. We utilize the bicistronic vector that contains the CIR, internal ribosome entry-site sequence (IRES), and SSTR2 or hNIS or HSV1-tk. Both SSTR2 and hNIS genes (with their leader or tag sequences from the pDisplay vector from Invitrogen, Carlsbad, Calif.) are first PCR amplified with appropriate primers (to make SalI-SSTR2-NotI) to swap with HSV1-tk in pIRES. Zeta chain will be inserted into MCS of pIRES using the fragment Xho1-zeta-Mlu1. After digestion with Xho1 and Not1, the ζ-IRES-HSV1-tk is swapped with ζ-chain in the scFv-CD28-ζ construct using Xho1 and blunt end ligation.

Anti-idiotype enrichment of viral producer line by cell sorting Building on initial successes with anti-idiotype enrichment of producer line, we will FACS sort the producer line to clone out the brightest 0.1% (following surface staining of producer line with anti-idiotypic antibody). This sorting can be repeated until there is no added improvement in mean fluorescence. The producer line is then subcloned using NK92 as indicator cells, and screened for scFv, SSTR2 (using anti-HA antibody) or hNIS (using anti-HA or MoAb specific for hNIS) gene expression by flow cytometry. Subcloning is repeated until a stable clonal producer line is obtained. The most efficient producer clone is selected for cell banking. We plan to use NK92 instead of K562 as indicator line because NK92 is relatively easy to transfect and clone and has great clinical potential. Previously we used centrifugation to effect viral attachment and infection of human lymphocytes (see Progress Report). We plan to further improve the efficiency of retroviral infection by using fibronectin fragment CH-296 (Takara Shuzo, Otsu, Japan), to augment gene transfer by interaction between VLA-4 on T-lymphocytes and FN adhesion site CS-1,[136] in conjunction with centrifugation.[137,138] In those reports, gene transduction increased from 12% to 18% with centrifugation and to 24% when centrifugation plus fibronectin was used.[138] The kinetics of surface SSTR2 expression and cytoplasmic HSV1-tk expression will be monitored. Day 40 scFv-modified lymphocytes will be analyzed for CD4 CD8, CD56, scFv, SSTR2 (or HSV1-tk) expression. After further expansion in culture, they will be analyzed for their iodine uptake and efflux. Protein expression can be confirmed by western blot and mRNA by Tagman quantitative RT-PCR[139] based on the known genomic/cDNA structure of SSTR2 and the fusion sequence of scFv-CD28-ζ. Gene copy number based on quantitative PCR method will also be used as previously described.[140]

Statistical analysis. Data are expressed as the mean±SEM. Statistical significance of differences is determined by conducting a paired Student's t-test.

Results In picking the winner (HSV1-tk, SSTR2, hNIS), the following criteria will be used:
1. maximal specific activity without damaging cellular function
2. maximal half-life (retention within cell)
3. maximal % ID/gm of ex vivo labeled lymphoid cells at 24 and 72 hours in tumor xenograft versus normal organs (liver, spleen and lung); for NK92 which grows as sc xenograft in SCID mice. Also considered is maximal % ID/gm of intravenous radiolabeled DOTATOC, radioiodine or radioiodinated FIAU.

HSV1-tk (~1 kp) gene transduction using IRES vector and its expression in human T-cells are now routine.[141] Although both hNIS (~2 kp) and SSTR2 have been transduced by retroviral vector into mammalian cells, efficiency of the IRES construct can vary. It is conceivable that the efficiency of gene transfer and gene expression could also vary between cloned line NK92 and primary human T lymphocytes. We plan to quantitate the gene copy number by real time PCR, mRNA by RT-PCR and correlate them with protein expression by flow cytometry and western blots. In vivo biodistribution of gene-modified NK92 cells and lymphocytes will be verified using immunostaining of mouse tissues and tumors employing biotinylated anti-idiotypic reagents. Alternatively, quantity of human lymphocytes in mouse tissues can also be measured by sensitive real time PCR (of transduced genes) as well as RT-PCR for mRNA using mouse Ǝ-actin and mouse GAPDH, respectively, to calculate relative copy number. We also plan to validate in vivo cell-imaging studies using radiolabeled anti-idiotypic reagents. Although anti-idiotypic reagents offer another alternative to marker genes for imaging T-cells, these reagents are not widely available as octreotide (already licensed by the FDA for total body imaging) and could be difficult to implement clinically.

In adoptive cell therapies, gene-marking allows precise evaluation of the quantity and persistence of these cells in vivo, as well as their distribution and function within tissues.[142] In studies of T cell therapy, this is of particular importance since many infused cells will undergo activation-induced death in vivo. [143] or immune elimination of gene-modified cells may occur, especially following repeated injections.[144] The development of sensitive, accurate and reproducible methods to quantify gene-marked cells in peripheral blood and tissues are essential for defining the long-term fate of transferred cells. Such pharmacokinetic information is crucial if understanding and optimization are to be pursued. We want to take advantage of instrumentation and software developed for SPECT and PET/micro-PET imaging. These tools will give unprecedented precision and dynamic information in future patient trials.

Specific Aim 2 Pretargeting of CD4+ T-Cells to Improve Adoptive Cell Therapy

The fate of CIR gene-modified T-cells in vivo remains unknown in most cases. Influx of inflammatory cells following local increase in vascular permeability during complement activation and release of anaphylatoxins is well known. An active process of recruitment may be equally if not more important in cellular immunity. The importance of recruitment by CD4+ T cells, chemokines and cytokines, as well as the myriad of adhesion molecules involved in lymphocyte rolling, adhesion, diapedesis, and movement within the tumor microenvironment have been previously emphasized.[145] Distinct roles for Th1 and Th2 for tumor eradication in vivo have recently been proposed. [146] While Th1 cells induce a marked lymphocyte infiltration into the tumor mass and eradicate tumor mass via cellular immunity and memory CTL, Th2 cells induce inflammatory responses and tumor necrosis through IL-4 recruitment of eosinophils and neutrophils. Th1 cells express high levels of P-selectin, and exhibit strong LFA-1/ICAM-1 dependent cell-cell interactions and Th2 cells interact with extracellular matrix through the integrins. Th1 cells are probably the lymphocytes responding actively to tumor cells and producing cytokines, which in turn recruit other effector cells including CD8+ T cells, NKT or NK cells into the tumor tissue. In contrast, Th2 cells, unable to enter tumor tissue because of their defect of adhesion, may accumulate on the endothelium and induce tumor necrosis via TNF-0 and/or release of reactive oxygen intermediates from eosinophils and macrophages to damage tumor vessels.

T cells homing depends on chemokines and receptors, clearly illustrated in allograft and graft rejection models.[147] CCR4, CXCR3, CCR5, and CCR7 are some of the key chemokine receptors for T-cell trafficking. CCR4 is the major trafficking receptor for systemic memory T cells. A pivotal role for CCR5 in T-cell migration to tumor sites induced by interleukin 12 treatment was recently reported. [148] CXCR3 is present on activated lymphocytes including CTL and NK cells.[149] Th1 cytokines and CXC3 chemokines can direct infiltration of adoptively transferred CD8+ T cells into the tumor site. CCR7, the lymph node-homing receptor, is expressed on CD4+ or CD8+ mature T cells. This is important since metastatic solid tumors often spread to marrow, bone, lung and liver. CCR7 downregulation may permit these cells to home to nonlymphoid metastastic sites. T-cells also play an important role in recruitment by using chemokines. RANTES enhances Th1 and CD8+CTL responses,[150] while CTLs can in turn release IL-8, MIP, RANTES, and IP-10.[151]

General Plan of Work:

Enrichment of CD4+ T-cells. In order to prepare sufficient numbers of T-cells for in vivo biodistribution studies, cultured CIR-gene modified T-cells (>95% scFv positive) will be purified into CD4+ and CD8+ populations by affinity chromatography using MiniMac System (Miltenyi).

Homing studies on separated CD4+ and CD8+ populations. Following CIR transduction and affinity purification, CD4+ cells will be checked by flow cytometry for surface phenotype and cytoplasmic cytokines, plus gene expression by microarrays. In addition, their antigen specific immune function will be checked in ELISPOT assays (IFN-γ). CD8+ cells will be analyzed likewise and their cytotoxicity confirmed in $^{51}$Cr release assay. The misdistribution of [CIR+ imaging]-gene modified CD4+ and CD8+ T-cells will be studied in mice with and without tumor xenografts. PET will be used for imaging and quantitative dosimetry. At specific time points, mice will undergo necropsy and tissues harvested for gamma counting. CD4+ T-cells with CIR but no imaging gene will also be tested in the pretargeting model. Indicator cells (both NK92 and T-lymphocytes) carrying the imaging gene, with or without CIR, will be tested for their homing response to pretargeted CD4+ T-cells either by (1) radiolabeling in vitro before administration iv, or (2) radiolabeling in vivo after they have had time to home to the tumor sites.

Quantitation by PET will be validated with tissue extraction and analysis by flow cytometry (quantitation of scFv+ cells). Here, single cell suspensions will be prepared from tumors and organs (blood, spleen, liver, and lymph nodes) by mechanical disruption and coarse filtering. Live cells will be marked by propidium iodide and their CD3, scFv, CD4 and CD8 expression quantified. Tumor cells will be marked with anti-gp58 (MoAb 8H9) or anti-GD2 (MoAb 3F8) antibodies. Number of T cells will be expressed as percent of total cells and per gram tumor or tissue weight for comparisons. In addition, total DNA and RNA will also be tested for scFv gene copy number and scFv transcript number using PCR and RTPCR, and normalized to mouse ∃-actin and mouse GAPDH, respectively. Again these will provide independent validation for the quantitation techniques described above.

Specific Methods:

Phenotypic characterization In addition to gene array analysis (chemokine and receptors, interleukin and receptors) on the CD4+ and CD8+ cells, their surface and cytoplasmic phenotype will also be studied by FACS analysis at select time points during in vitro culture. These markers include CD4, CD8, CD25, CD45RO, CD69, VLA-4, LFA-1a, LFA-1-b, L-selectin, CCR4, CCR5, CXCR3, CRTH2, CCR7, cytoplasmic granzyme B, IL-2, IL-4, and IFN-(. Specific antibodies are obtained from the NIH AIDS Resource Program as well from commercial sources: anti-CCR3 (R&D systems, Minneapolis, Minn.), anti-CXCR3 (R&D), anti-CCR5 (Pharmingen, San Diego, Calif.), anti-CCR4 (Dr. Chantry, Icos Corporation, Bothell, Wash.) and anti-CCR7 (Pharmingen). Four color fluorescence will be performed: APC-anti-CD3, PerCP-anti-CD8, FITC-2E9 (anti-idiotype) and PE-antibody (specific for adhesion molecules, cytokines, and chemokine receptors). Appropriate controls will be included for channel compensation.

Intracellular cytokine expression For the detection of cytoplasmic cytokines, cells are first cultured in the presence of brefeldin A (Sigma), stained with PerCP-anti-CD4 MoAb, fixed with 4% paraformaldehyde, and treated with permeabilizing solution (50 mM NaCl, 5 mM EDTA, 0.02% NaN3, 0.5% Triton X-100, pH 7.5) before staining with PE-conjugated anti-IL4, and FITC conjugated anti-IFN-g for 45 min on ice. The percentage of cells expressing cytoplasmic IL-4 (Th2) or IFN-((Th1) is determined by flow cytometry.

Results We test the hypothesis that pretargeting of CD4+ T-cells can increase the homing efficiency of subsequent injections of NK cells and lymphocytes. Although NK92 is used as an indicator cell in our experiments, their broad anti-tumor activity and preliminary clinical applications are encouraging evidence of its clinical utility. Since the current limitation of adoptive cell therapy using killer cell lines like NK92 remains suboptimal in efficiency in tumor targeting, the ability of CD4+ T-cells to facilitate this tumor-homing property can potentially improve their anti-tumor efficacy, which we will test in xenografted SCID mice. Our studies will also attempt to characterize the ability of CD4+ T cells (armed with CIR) to recruit untargeted NK cells and untargeted T-lymphocytes (i.e. without CIR), and if this recruitment translates into significant anti-tumor effect. It is also possible that other human white cell populations as well as stem cells can be studied in this homing model. Although the SCID mice provide a model to test human T-cell homing, it has inherent limitations. For example, tumor stroma is mostly mouse-derived, not made up of human stromal cells, and thus are missing certain chemokines and cytokines that can positively or negatively modulate the T-cell homing properties. In addition, SCID xenografts are generally made up of mouse-derived vasculature, and as such will not interact with human lymphocytes or inflammatory cells in a physiological manner. Nevertheless, these tests will allow us to validate the imaging gene technique especially when applied in quantitative PET imaging of gene-modified T-cells. A noninvasive technique to quantitate lymphocyte trafficking will undoubtedly require much further refinement, and likely necessitates using human patients. Positive results from these studies will provide the rationale for further developments in their clinical translation.

Interpretations and implications The biology of chemokine receptors and adhesion molecules in directing T cell traffic is a rapidly advancing field. As the science of cytotherapy becomes more sophisticated, purer subpopulations of lymphocytes with defined functions will become available for in vivo studies. Understanding the cellular cascade in orchestrating tumor targeting will provide crucial information for diagnostic and therapeutic manipulations. Reliable methods to trace label these cells without damaging their cellular function are still technologic gaps in cytotherapy.

Specific Aim 3 Improving Tumor Homing and Tumor Cytotoxicity by Using Professional T-Lymphocytes (CTL) and NK92 for CIR Gene-Modification General Plan of Work:

In both specific aims 1 and 2, we propose to use NK92 as our indicator line. NK91 is a cloned professional NK killer cell line. They have potential clinical utility in adoptive cell therapy in early human trials. Antigen specific CTLs, when highly enriched, are also efficient killing machines ideal for adoptive cell therapy. More importantly, these enrichment steps can also remove substantial numbers of alloreactive T cells, such that allogeneic CTLs may be safe to use. This is particularly relevant when one considers the paucity of healthy T cells in patients after intensive chemotherapy available for gene-modification. EBV-specific T cells can be selected early after in vitro sensitization, while alloreactive T cells are substantially depleted by this approach,[85] enriching the auto/allo ratio by 39-fold. Indeed these EBV-specific T cells can be continually boosted periodically with EBV-infected cells in vitro, and maintain their ability to home to and kill specifically EBV-lymphomas in vivo.[141] The specificity of these CTLs is exquisite, since allogeneic EBV-lymphomas are not killed.

Viral antigen-specific T cells have been successfully used in adoptive therapies in patients.[20-23] Adoptively transferred donor-derived EBV-specific T cells can effectively eliminate B-cell proliferative disorders in the post-transplant period: a dramatic proof of principle for adoptive T-cell approach in cancer therapy, emphasizing their efficacy and relative safety.[22,23,25] When genetically tagged with the neomycin resistance gene using a retroviral vector,[26] these CTLs can be shown to last for up to 18 months.[22] The persistence of these EBV-specific CTLs probably reflects a continual antigenic challenge from dormant EBV virus residing in the body after primary infection. Recently, Rossig et al have shown that these CTLs can be gene modified with scFv-CIR.[152] We have also demonstrated that complex scFv-CD28-. chimeric gene can be transduced into these CTLs whereupon continual clonal expansion>$10^5$ fold for many months (Progress Report).

We propose to arm EBV-specific professional CTLs with scFv-CIR. As CTLs they are effective and safe, both in vitro and in vivo. They can be gene-modified using retrovirus. They mount effective amnanestic CTL response. And most importantly, using rapid in vitro selection,[85] alloreactivity can be eliminated. This approach will enable allogeneic CTLs to be used for scFv-based T cell therapy. EBV-specific CTLs from designated normal donors will greatly increase the efficacy and success of gene-modified T cells. More importantly, there is no chance of contamination by tumor cells if allogeneic T cells are used.

Specific Methods:

Production and culture of EBV-lymphoblastic cell lines PBMCs at a concentration of $1 \times 10^6$/mL will be incubated for 24 hours after isolation by Ficoll-Hypaque density centrifugation with the EBV containing supernatant of the marmoset cell line 95-8 in the presence of 0.5 ug phytohemagglutinin (PHA)-16 (Murex-Diagnostik, Norcross, Ga.) in RPMI 1640 (GIBCO, Life Technologies, Grand Island, N.Y.), 10% heat-inactivated fetal calf serum (FCS), 10 U/mL penicillin, 10 ug/mL streptomycin, and 1% L-glutamine. After 24 hours, cells are washed and recultured in EBV-containing medium without PHA in 24-well plates at a concentration of $1 \times 10^6$/mL. Cells are then fed fresh RPMI 1640 with 10% FCS, L-glutamine, penicillin, and streptomycin twice a week and expanded according to the growth and cell number. The cells are finally characterized by fluorescence-activated cell sorter (FACS) analysis using CD3, CD 19, and CD20 monoclonal antibodies (Becton Dickinson). Aliquots of the immortalized B-lymphoblastoid cell lines (BLCLs) are frozen and the remaining cells maintained in culture. Homozygous BLCLs for the HLA-A and HLA-B alleles, generously provided by Dr. B. Dupont of MSKCC are maintained in the same medium. PHA blasts are generated by culturing $1 \times 10^6$/mL PBMC with 0.5 ug/mL PHA-16 for 3 days. The cells were washed and further cultured for 4 days in the presence of 5 IU/mL interleukin (IL-2) (Collaborative Biomedical Products, Bedford, Mass.).

Generation and culture of EBV-specific CTLs PBMCs are isolated by Ficoll-Hypaque density centrifugation of anticoagulated whole blood. T lymphocytes are positively selected by staining with an anti-CD3 phycoerythrin monoclonal antibody (Becton Dickinson) on a MoFlo cell sorter (Cytomation, Fort Collins, Colo.), achieving a purity of more than 98%. EBV-specific CTLs are generated by stimulating $1 \times 10^6$/mL CD3+ cells with $2.5 \times 10^4$/mL autologous BLCLs, which are irradiated with 60 Gy in Iscove's modified Dulbecco's medium supplemented with 10% heat-inactivated human AB serum (Gemini, Calabasas, Calif.), 35-ug/mL transferrin, 5-ug/mL insulin, $2 \times 10^{-5}$M ethanolamine, 1 ug/mL palmitic acid, 1 ug/mL linoleic acid, and 1 ug/mL oleic acid (all from Sigma) for 6 days in 25-cm² flasks. Cells are then washed, recultured at a concentration of $1 \times 10^6$/mL, and restimulated with $2 \times 10^5$/mL BLCL at day 7. Cells are either prepared for gene transfer on day 8 (early gene transfer) or kept in culture with restimulations weekly at an effector-to-target ratio of 5:1. After the third restimulation, T cells are prepared for gene transfer on day 23 (late gene transfer). A total of 5 IU of IL-2 (Collaborative Biomedical Products) are added for the first time at day 10 to the cultures and 2 to 3 times weekly thereafter. For generation of alloreactive cells, donor T cells are stimulated with fully mismatched allogeneic EBV BLCL. These cells are now routinely generated in the Bone Marrow Transplantation Research Laboratory at MSKCC under the supervision of Dr. G. Koehne, co-investigator.

Gene transfer We have shown (see Progress Report) that EBV-specific CTLs can be easily gene-modified using our strategy developed for primary T-cells. EBV-activated T cells (day 5, day 8, or day 23 of culture) or anti-CD3/anti-CD28-immobilized monoclonal antibody stimulated cells are placed in fibronectin-coated wells according to the technique described by Pollok et al[137] 5 ug/mL of fibronectin fragments (TaKaRa Biomedicals, Shiga, Japan) are coated on nontissue culture treated plates for 2 hours at room temperature in 6-well plates. Plates were blocked with 1% human serum albumin for at least 30 minutes and washed twice with PBS. Cells are plated at a concentration of $10^6$/mL for 24 hours. Viral supernatant is added and spun for 60 min at 1000 rpm at room temperature. Fifty percent of the supernatant is replaced with fresh medium containing 10% heat-inactivated human AB serum and 10 IU/mL IL-2. Cells will be maintained in culture at a concentration of $10^6$/mL to $1.5 \times 10^6$/mL.

Flow cytometric analysis Monitoring of the gene expression of scFv of T lymphocytes will be performed by 2-color flow cytometry using FACScan (Becton Dickinson) by labeling the cells with an anti-scFv-idiotype monoclonal antibody on ice for 45 minutes. FITC-goat anti-rat antibody is added for 15 minutes as secondary antibody. After blocking with normal mouse serum (ICN/CAPPEL, Aurora, Ohio) for 10 minutes, anti-CD3 phycoerythrin (Becton Dickinson) is added for 15 minutes. Cells are washed twice with PBS after each step and before analysis. Phenotyping of specific CTL lines is performed by gating lymphocytes using forward sight scatter and sideward sight scatter. Cells are stained with anti-CD3, anti-CD4, and anti-CD8 for T-cell subpopulations. Although cells have been purified initially for T lymphocytes, the transduced cells will be reanalyzed for the presence of natural killer (NK) cells, defined as CD3-CD16+CD56+, using anti-CD16 and anti-CD56 monoclonal antibodies (Becton Dickinson).

Cell purification by affinity chromatography Gene-modified cells are prepared for purification using affinity purification on MiniMAC columns as described in the previous section.

Cytotoxicity assay Cytolytic activity of effector cells is assayed against $^{51}$Cr-labeled targets in standard 4-hour release assays. Target cells include autologous BLCLs, HLA class I mismatched allogeneic BLCLs, and K562 for major histocompatibility complex (MHC)-unrestricted lysis as a parameter for NK cell lysis and PHA blasts. For each donor HLA class I allele, a BLCL expressing the HLA-A and HLA-B allele homozygously can be included to determine the HLA restriction of the EBV-specific CTLs. Briefly, $1 \times 10^6$ target cells are incubated with 3700 kBq $^{51}$Cr for 1 hour, washed 3 times, and plated in 96 wells. Cytotoxicity is analyzed using $0.8 \times 10^5$ effector cells: $4 \times 10^3$ target cells per well in a total volume of 200 uL, at an effector-to-target ratio of 20:1. All targets are plated in triplicate. After an incubation of 4 hours, supernatants are harvested and the specific cytotoxicity determined using a microplate scintillation counter (Packard Instruments, Downer's Grove, Ill.). The percentage of specific lysis is calculated as 100%×(experimental release−spontaneous release)/(maximum release−spontaneous release). Maximum release is obtained by adding 100 uL of 5% Triton X-100 to the 100 uL medium containing target cells. Spontaneous release is consistently below 15% of maximum release in all assays.

Comparison of professional killer versus naïve T-lymphocyte in tumor targeting and therapy In order to test if CIR-gene modified professional killer cells are indeed superior in CIR technology, we compare them with CIR-gene modified naïve T-cells as follows:
1. In vitro cytotoxicity ($^{51}$Cr release and IFN-(release) against tumor cell lines
2. In vivo anti-xenograft activity at various T-cell doses
3. Quantitative difference in homing measured in % injected dose/gm over time (for lymphocytes labeled ex vivo or labeled in vivo) by quantitative PET, tissue counting, immunohistochemistry, and PCR/RT-PCR
4. Qualitative difference in CD4+ T-cells in their ability to recruit either IR-modified T-cells, measured by quantitative PET, tissue counting, immunohistochemistry, and PCR/RT-PCR.
5. Qualitative difference in CD8+ T-cells in their ability to respond to pretargeted CD4+ cells, measured by quantitative PET, tissue counting, immunohistochemistry, and PCR/RT-PCR.

Results We expect the use of professional CTLs to greatly increase the efficiency, specificity, and utility of CIR-modified T cells, as recently reported.[152] Since these cells are selected for EBV with minimal alloreactivity the possibility of using healthy tumor-free allogeneic lymphocytes will increase the chance of full T cell potential in vivo, a close analogy to adoptive allogeneic T cell therapy of EBV-lymphoma. Issues in using autologous T cells, such as immunosuppression by cancer and by chemo-radiotherapy, defective T cell signaling, and tumor contamination are no longer limiting factors. Clearly, allogeneic cells will be rejected by normal hosts even if they are HLA-matched. Fortunately, in patients with solid tumors undergoing high dose therapy, their immune system is often incapacitated, albeit temporarily. In addition, combination of cyclosporin plus mycophenolate mofetil has been quite effective in suppressing graft versus host disease as well as allo-sensitization in preliminary animal studies and early patient trials.[153] We expect the immediate post-chemotherapy period in patients with solid tumors to be relatively immunosuppressed to allow allogeneic T-cells to survive as least for a brief period of weeks to exert its antitumor effect. With immunologic recovery, these gene-modified cells will be eliminated, together with the risk of them becoming cancerous or causing long term autoimmunity. Autologous T cells would have recovered enough by then to allow autologous EBV-specific CTLs to be used. Whether committed EBV-CTLs have shorter life spans than naive T cells after CIR gene-modification remain to be determined. It is likely to expect these preprogrammed professional killer cells (EBV-specific CTL), being preselected in their priming period to express the appropriate repertoire of adhesion molecules (ICAM and selectins), cytokine/interleukins (e.g. IL2, IL4, IL12) and receptors (IL2R, IL7R, IL15R), chemokines (RANTES, IP10) and receptors (CCR5, CXCR3, CCR4), to show better anti-tumor activity than primary T-cells.

Interpretations and Implications The identification of an optimal gene design in the allogeneic setting will increase the likelihood of clinical benefit of CIR technology. The ability to produce large clonal populations of tumor specific T-cells from normal donors for lymphocyte therapy will increase the chance of its successful clinical translation.

TABLE 4

NK92 surface phenotype by FACS

| NK Phenotype | |
| --- | --- |
| CD56 | +++ |
| CD16 | − |
| CD3 | − |
| CD4 | − |
| CD8 | − |
| CD2 | ++ |
| CD7 | +++ |
| CD25 (IL2Ra) | + |
| CD122 (IL-2Rb) | ++ |
| Cell adhesion molecules (CAM) Ig superfamily | |
| CD54 (ICAM-1) | +++ |
| CD102 (ICAM-2) | ++ |
| CD50 (ICAM-3) | + |
| Integrins B1 | |
| CD29 (B1 integrin B chain) | ++ |
| CD49d (VLA-4 a chain) | +++ |
| CD49e (VLA-5 a chain) | − |
| B2 | |
| CD18 (B2 integrin B chain) | +++ |
| CD11a (LFA-1 a chain) | +++ |
| CD11b (Mac-1 a chain) | − |
| CD11c (p150/95 a chain) | + |
| Other CAM | |
| CD44H | +++ |
| CD44R1 | ++ |
| CD58 (LFA-3) | +++ |
| NKregulatory Receptors | |
| CD158a | − |
| CD158b | − |
| KIR70 | − |
| CD94 | ++ |
| NKG2A | +++ |
| Miscellaneous | |
| CD28 | ++ |
| CD152 (CTLA-4) | − |
| CD80 | + |
| CD86 | ++ |
| C95 (Fas) | + |
| FasL | −/+ |
| CD69 | ++ |
| CD34 | − |
| CD43 | +++ |
| CD48 | +++ |

TABLE 5

8H9-scFv-CD28-zeta

| | T-cells | NK92 |
| --- | --- | --- |
| IL1A | — | — |
| IL1B | W | — |
| FIL1(ε) | W | W |
| FIL1 | — | — |
| FIL1(ζ) | Y | Y |
| IL-1H1 | — | — |
| IL2 | — | — |

TABLE 5-continued

| 8H9-scFv-CD28-zeta | | |
|---|---|---|
| | T-cells | NK92 |
| IL3 | W | W |
| IL4 | W | — |
| IL5 | W | — |
| IL6 | Y | W |
| IL7 | W | Y |
| IL8 | — | W |
| IL9 | Y | Y |
| IL10 | — | W |
| IL11 | Y | Y |
| IL12A | Y | W |
| IL12B | — | — |
| IL13 | W | — |
| IL14 | W | W |
| IL15 | Y | Y |
| IL16 | W | W |
| IL17 | W | W |
| IL17B | W | W |
| IL17C | — | W |
| IL17E | Y | Y |
| IL17F | Y | Y |
| IL18 | — | — |
| IL19 | Y | Y |
| IL20 | — | — |
| IL21 | Y | Y |
| IL22 | Y | Y |
| IL23A | Y | Y |
| IL24 | W | W |
| IL26 | — | — |

TABLE 6

| 8H9-scFv-CD28-zeta | | |
|---|---|---|
| | T-cells | NK92 |
| IL1R1 | W | W |
| IL1R2 | W | Y |
| IL1RL1 | — | — |
| IL1RL2 | — | — |
| IL1RAP | W | W |
| IL1RAPL1 | W | W |
| IL1RAPL2 | — | W |
| IL1RN | W | — |
| IL1HY1 | — | — |
| IL2RA | W | W |
| IL2RB | W | W |
| IL2RG | Y | Y |
| IL3RA | — | — |
| IL4R | — | — |
| IL5RA | — | — |
| IL6R | — | W |
| IL6ST | — | — |
| IL7R | — | — |
| IL8RA | — | — |
| IL8RB | — | — |
| IL9R | W | W |
| IL10RA | Y | Y |
| IL10RB | W | W |
| IL11RA | W | W |
| IL12RB1 | W | W |
| IL12RB2 | — | W |
| IL13RA1 | W | — |
| IL13RA2 | W | — |
| IL15RA | W | W |
| IL17R | Y | Y |
| IL18R1 | — | — |
| IL18BP | W | Y |
| IL18RAP | — | — |
| IL20RA | W | W |
| IL21R | Y | Y |
| IL22R | W | Y |
| IL22RA2 | Y | Y |

TABLE 7

| 8H9-scFv-CD28-zeta | | |
|---|---|---|
| | T-cells | NK92 |
| ENA-78 | W | — |
| Eotaxin | W | — |
| GCP-2 | Y | Y |
| I-TAC (IP9) (SCYB11) | — | — |
| lymphotactin | Y | Y |
| MCP-1 (SCYA2) | — | — |
| MCP-2 | — | — |
| MCP-3 | — | — |
| MCP-4 | — | — |
| MDC | Y | Y |
| MIP-1 delta | W | Y |
| MIP-1a | Y | Y |
| MIP-1b | Y | Y |
| MIP-2 (SCYA21) | W | W |
| MIP-3a | — | — |
| MPIF-1 | Y | Y |
| MPIF-2 | — | — |
| P10 (IP 10) | — | — |
| PARC | W | Y |
| SCYA19 | Y | Y |
| SCYA5 (RANTES) | Y | Y |
| SCYB13 | Y | Y |
| SCYC2 | Y | Y |
| SCYE1 | W | Y |
| SDF1 | Y | Y |
| SDF2 | Y | Y |
| TARC (SCYA17) | Y | Y |

TABLE 8

| 8H9-scFv-CD28-zeta | | |
|---|---|---|
| | T-cells | NK92 |
| CCR1 | W | W |
| CCR2 | Y | Y |
| CCR3 | — | — |
| CCR4 | Y | Y |
| CCR5 | Y | Y |
| CCR6 | W | — |
| CCR7 | W | W |
| CCR8 | W | — |
| CCR9 | W | W |
| CX3CR1 | — | — |
| CXCR4 | W | Y |
| CXCR5 (BLR1) | — | — |
| XCR1 | Y | Y |

TABLE 9

IC50 values (nM) for Octreotide analogs against $^{125}$I-SST-14

| | SSTR | | | | |
|---|---|---|---|---|---|
| Peptide | 1 | 2 | 3 | 4 | 5 |
| Octreotide | >1000 | 2 | 187 | >1000 | 22 |
| DTPA-Octreotide | >1000 | 12 | 387 | >1000 | 299 |
| DOTA-Octreotide | >1000 | 14 | 27 | >1000 | 103 |
| DOTA-Tyr3-Octreotide | >1000 | 14 | 880 | >1000 | 393 |
| Y-DOTA-Tyr3-Octreotide | >1000 | 11 | 389 | >1000 | 114 |
| Ga-DOTA-Tyr3-Octreotide | >1000 | 2.5 | 613 | >1000 | 73 |
| In-DTPA-Octreotide | >1000 | 22 | 182 | >1000 | 237 |
| Y-DOTALAN | >1000 | 23 | 290 | >1000 | 16 |
| Re0-P829 | >1000 | 2.5 | 1.5 | >1000 | 2 |

REFERENCES

1. Crist W, Gehan E A, Ragab A H, et al: The third intergroup rhabdomyosarcoma study. J Clin Oncol 13:610-630, 1995

2. Weigel B J, Breitfeld P P, Hawkins D, et al: Role of High-Dose Chemotherapy With Hematopoietic Stem Cell Rescue in the Treatment of Metastatic or Recurrent Rhabdomyosarcoma. Am J Pediatr Hematol Oncol 23:272-276, 2001
3. Ruymann F B, Grovas A C: Progress in the diagnosis and treatment of rhabdomyosarcoma and related soft tissue sarcomas. Cancer Invest 18:223-41, 2000
4. Huston J S, Levinson D, Mudgett-Hunter M, et al: Protein engineering of antibody binding sites: recovery of specific activity in an anti-digoxin single-chain Fv analogue produced in *Escherichia coli*. Proceedings of the National Academy of Sciences of the United States of America 85:5879-83, 1988
5. Bird R E, Hardman K D, Jacobson J W, et al: Single-chain antigen-binding proteins. Science 242:423-426, 1988
6. Winter G, Milstein C: Man-made antibodies. Nature 349:293-299, 1991
7. George A J T, Spooner R A, Epenetos A A: Applications of Monoclonal Antibodies in Clinical Oncology. Immunology Today 15:559-561, 1994
8. Winter G, Griffiths A D, Hawkins R E, et al: Making antibodies by phage display technology. Annual Review of Immunology 12:433-55, 1994
9. Raag R, Whitlow M: Single-chain Fvs. FASEB Journal 9:73-80, 1995
10. Burton D R, Barbas III C G: Human antibodies from combinatorial libraries. Advances in Immunology 57:191-280, 1994
11. Cai X, Garen A: Anti-melanoma antibodies from melanoma patients immunized with genetically modified autologous tumor cells: selection of specific antibodies from single-chain Fv fusion phage libraries. Proceedings of the National Academy of Sciences of the United States of America 92:6537-41, 1995
12. Shu L, Qi C F, Schlom J, et al: Secretion of a single-gene-encoded immunoglobulin from myeloma cells. Proceedings of the National Academy of Sciences of the United States of America 90:7995-9, 1993
13. Kipriyanov S M, Bretling F, Little M, et al: Single-chain antibody streptavidin fusions: tetrameric bifunctional scFv-complexes with biotin binding activity and enhanced affinity to antigen. Human Antibodies Hybridomas 6:93-101, 1995
14. Michael N P, Chester K A, Melton R G, et al: In vitro and in vivo characterisation of a recombinant carboxypeptidase G2::anti-CEA scFv fusion protein. Immunotechnology 2:47-57, 1996
15. Wikstrand C J, Hale L P, Batra S K, et al: Monoclonal antibodies against EGFRvIII are tumor specific and react with breast and lung carcinomas and malignant gliomas. Cancer Research 55:3140-8, 1995
16. Alt M, Muller R, Kontermann R E: Novel tetravalent and bispecific IgG-like antibody molecules combining single-chain diabodies with the immunoglobulin γ1 Fc or CH3 region. FEES Letters 454:90-94, 1999
17. DeNardo S J, DeNardo G L, DeNardo D G, et al: Antibody phage libraries for the next generation of tumor targeting radioimmunotherapeutics. Clinical Cancer Research 5:3213s-3218s, 1999
18. Santos A D, Kashmiri S V, Hand P H, et al: Generation and characterization of a single gene-encoded single-chain-tetravalent antitumor antibody. Clinical Cancer Research 5:3118s-3123s, 1999
19. Eshhar Z, Waks T, Gross G, et al: Specific activation and targeting of cytotoxic lymphocytes through chimeric single chains consisting of antibody-binding domains and the gamma or zeta subunits of the immunoglobulin and T-cell receptors. Proceedings of the National Academy of Sciences of the United States of America 90:720-4, 1993
20. Riddell S R, Watanabe K S, Goodrich J M, et al: Restoration of viral immunity in immunodeficient humans by the adoptive transfer of T cell clones. Science 257:238-241, 1992
21. Walter E A, Greenberg P D, Gilbert M J, et al: Reconstitution of cellular immunity against cytomegalovirus in recipients of allogeneic bone marrow by transfer of T-cell clones from the donor. N Engl J Med 333:1038-1044, 1995
22. Heslop H E, Ng C Y C, Li C, et al: Long-term restoration of immunity against epstein-barr virus infection by adoptive transfer of gene-modified virus-specific T lymphocytes. Nature Med 2:551-555, 1996
23. Papadopoulos E B, Ladanyi M, Emanuel D, et al: Infusions of donor leukocytes to treat Epstein-Barr virus-associated lymphoproliferative disorders after allogeneic bone marrow transplantation. N Engl J Med 330:1185-1191, 1994
24. Rosenberg S, Lotze M, Muul L, et al: A progress report on the treatment of 157 patients with advanced cancer using lymphokine-activated killer cells and interleukin-2 or high-dose interleukin-2 alone. N Engl J Med 316:889-897, 1988
25. Heslop H E, Rooney C M: Adoptive cellular immunotherapy for EBV lymphoproliferative diseases. Immunological Reviews 157:217-222, 1997
26. Rooney C M, Smith C A, Ng C Y C: Use of gene-modified virus-specific T lymphocytes to control Epstein-Barr virus-related lymphoproliferation. Lancet 345:9, 1995
27. Botti Cea: Comparison of three different methods for radiolabelling human activated T lymphocytes. Eur J Nucl Med 24:497-504, 1997
28. Melder RJea: A method for labeling cells for positron emission tomography (PET) studies. J Immunol Methods 175:79-87, 1994
29. McAfee J G, Thakur M L: Survey of radioactive agents for in vitro labeling of phagocytic leukocytes II. Particles. J Nucl Med 17:488-492, 1976
30. Puncher M R, Blower P J: Labelling of leucocutyes with-colloidal technetium-99m-SnF2: an investigating of the labelling process of autoradiography. Eur J Nucl Med 22:101-107, 1995
31. Korf Jea: Divalent cobalt as a label to study lymphocyte distribution using PET and SPECT. J Nucl Med 39:836-841, 1998
32. Harwood SJea: Use of technetium antigranulocyte monoclonal antibody Fab' fragments for the detection of osteomyelitis. Cell Biophys 25:99-107, 1994
33. Kipper S L: The role of radiolabeled leukocyte imaging in the management of patients with acute appendicitis. Q J Nucl Med 43:83-92, 1999
34. Welling Mea: Detection of experimental infections with 99 mTc-labeled monoclonal antibodies against TNF-alpha and interleukin-8. Nucl Med Biol 24:649-655, 1997
35. Coleman R, Datz F: Detection of inflammatory disease using radiolabeled cells, in Diagnostic Nuclear Medicine, M. Sandler, et al., Editors. Baltimore, Md., Williams & Wilkins, 1996
36. Albright JWea: Effects of aging on the dynamics of lymphocyte organ distribution in mice: use of a radioiodinated cell membrane probe. Mech Ageing Dev 101:197-211, 1998

37. Mukherji Bea: Imaging pattern of previously in vivo sensitized and interleukin-2 expanded autologous lymphocytes in human cancer. Int Rad Appl Instrum G 15:419-427, 1988
38. Fisher Bea: Tumor localization of adoptively transferred indium-111 labeled tumor infiltrating lymphocytes in patients with metastatic melanoma. J Clin Oncol 7:250-261, 1989
39. Coulie P G, Somville M, Lehmann F, et al: Precursor frequency analysis of human cytolytic T lymphocytes directed against autologous melanoma cells. Int J Cancer 50:289-297, 1992
40. Lacerda J F, Ladanyi M, Louie D C, et al: Human epstein-barr virus (EBV)-specific cytotoxic T lymphocytes home preferentially to and induce selective regressions of autologous EBV-induced B cell lymphoproliferations in xenografted C.B-17 Scid/Scid mice. J. Exp. Med. 183: 1215-1228, 1996
41. Wagstaff J, Gibson C, Thatcher N: A method for following human lymphocyte traffic using indium 111 oxine labelling. Clinical Experimental Immunology 43:435-442, 1981
42. Daniel P T, Kroidl A, Cayeux S, et al: Costimulatory signals through B7.1/CD28 prevent T cell apoptosis during target cell lysis. J Immunol 159:3808-3815, 1997
43. Stancovski I, Schindler D G, Waks T, et al: Targeting of T lymphocytes to Neu/HERe-expressing cells using chimeric single chain Fv receptors. J Immunol 151:6577-6582, 1993
44. Moritz D, Wels W, Mattern J, et al: Cytotoxic T lymphocytes with a grafted recognition specificity for ERBB2-expressing tumor cells. Proc. Natl. Acad Sci, USA 91:4318-4322, 1994
45. Wels W, Moritz D, Schmidt M, et al: Biotechnological and gene therapeutic strategies in cancer treatment. Gene 159: 73-80, 1995
46. Hwu P, Shafer G E, Treisman J, et al: Lysis of ovarian cancer cells by human lymphocytes redirected with a chimeric gene comosed of an antibody variable region and the Fc-receptor gamma-chain. J. Exp. Med. 178:361-369, 1993
47. Eshhar Z, Waks T, Bendavid A, et al: Functional expression of chimeric receptor genes in human T cells. J Immunol Methods 248:67-76, 2001
48. Rossig C, Bollard C M, Nuchtern J G, et al: Targeting of G(D2)-positive tumor cells by human T lymphocytes engineered to express chimeric T-cell receptor genes. Int J Cancer 94:228-36, 2001
49. Ma Q, Gonzalo-Daganzo R M, Junghans R P: Genetically engineered T cell as adoptive immunotherapy of cancer, in Giaccone G, Schilsky, R, Sondel, P. (ed): Cancer Chemotherapy and Biological Response Modifiers. Amsterdam, Elsevier Science B.V., 2002
50. Rosenberg S A: Cell transfer therapy: clinical applications, in DeVita V T J, Hellman S, Rosenberg S A (eds): Biologic therapy of cancer (ed second). Philadelphia, J.B.Lippincott Company, 1995, pp 487-506
51. Yang A-G, Chen S-Y: A new class of antigen-specific killer cells. Nat Biotechnol 15:46-51, 1997
52. Culver K W, Ram Z, Wallbridge S, et al: In vivo gene transfer with retroviral vector-producer cells for treatment of experimental brain tumors. Science 256:1550, 1992
53. Wei M X, Tamiya T, Chase M: Experimental tumor therapy in mice using the cyclophosphamide-activating cytochrome P450 2B1 gene. Hum Gene Ther 5:969, 1994
54. Zier K, Gansbacher B, Salvadori S: Preventing abnormalities in signal transduction of T cells in cancer: the promise of cytokine gene therapy. Immunology Today 17:39-45, 1996
55. Leeuwen J E M, Samelson L E: T cell antigen-receptor signal transduction. Curr Opin Immunol 11:242-248, 1999
56. Watts T H, DeBenedette M A: T cell co-stimulatory molecules other than CD28. Curr Opin Immunol 11:286-293, 1999
57. Brocker T: Chimeric Fv-zeta or Fv-epsilon receptors are not sufficient to induce activation or cytokine production in peripheral T cells. Blood 96:1999-2001, 2000
58. Krause A, Guo H F, Tan C, et al: Antigen-dependent CD-28 signaling enhances survival and proliferation in genetically modified activated human primary T lymphocytes. J. Exp. Med. 188:619-626, 1998
59. Finney H M, Lawson A D G, Bebbington C R, et al: Chimeric receptors providing both primary and costimulatory signaling in T cells from a single gene product. J Immunol 161:2791-2797, 1998
60. Maher J, Brentjens R J, Gunset G, et al: Human I-lymphocyte cytotoxicity and proliferation directed by a single chimeric TCRzeta/CD28 receptor. Nat Biotechnol 20:70-5, 2002
61. Haynes N M, Trapani J A, Teng M W L, et al: Single-chain antigen recognition receptors that co-stimulate potent rejection of established experimental tumors. Blood:2002-04-1041, 2002
62. Lenschow D J, Walunas T L, Bluestone J A: CD28/B7 system of T cell costimulation. Annu Rev Immunol 14:233-258, 1996
63. Laux I, Khoshnan A, Tindell C, et al: Response differences between human CD4(+) and CD8(+) T-cells during CD28 costimulation: implications for immune cell-based therapies and studies related to the expansion of double-positive T-cells during aging. Clin Immunol 96:187-97, 2000
64. Gruss H J, Dower S K: Tumor necrosis factor ligand superfamily: involvement in the pathology of malignant lymphomas. Blood 85:3378-404, 1995
65. Smith C A, Farrah T, Goodwin R G: The TNF receptor superfamily of cellular and viral proteins: activation, costimulation, and death. Cell 76:959-62, 1994
66. Del Prete G, De Carli M, Almerigogna F, et al: Preferential expression of CD30 by human CD4+ T cells producing Th2-type cytokines. FASEB Journal 9:81-6, 1995
67. Flynn S, Toellner K M, Raykundalia C, et al: CD4 T cell cytokine differentiation: the B cell activation molecule, OX40 ligand, instructs CD4 T cells to express interleukin 4 and upregulates expression of the chemokine receptor, Blr-1. Journal of Experimental Medicine 188:297-304, 1998
68. Sugita K, Torimoto Y, Nojima Y, et al: The 1A4 molecule (CD27) is involved in T cell activation. Journal of Immunology 147:1477-83, 1991
69. Kim Y J, Kim S H, Mantel P, et al: Human 4-1BB regulates CD28 co-stimulation to promote Th1 cell responses. European Journal of Immunology 28:881-90, 1998
70. Cheung N K V, Kushner B H, Cheung I Y, et al: Anti-GD2 antibody treatment of minimal residual stage 4 neuroblastoma diagnosed at more than 1 year of age. J Clin Oncol 16:3053-3060, 1998
71. Yeh S D, Larson S M, Burch L, et al: Radioimmunodetection of neuroblastoma with iodine-131-3F8: Correlation with biopsy, iodine-131-metaiodobenzylguanidine (MIBG) and standard diagnostic modalities. J Nucl Med 32:769-776, 1991

72. Cheung N K, Neely J E, Landmeier B, et al: Targeting of ganglioside G(-D2) monoclonal antibody to neuroblastoma. J Nucl Med 28:1577-1583, 1987
73. Cheung N K, Landmeier B, Neely J, et al: Complete tumor ablation with iodine 131-radiolabeled disialoganglioside GD2 specific monoclonal antibody against human neuroblastoma xenografted in nude mice. J. Natl. Cancer Inst. 77:739-745, 1986
74. Cheung N K, Kushner B H, LaQuaglia M, et al: N7: A novel multi-modality therapy of high risk neuroblastoma (NB) in children diagnosed over 1 year of age. Med Pediatr Oncol 36:227-230, 2001
75. Cheung N K: Monoclonal antibody based therapy for neuroblastoma. Current Oncology 2:547-553, 2000
76. Thomson B, Hawkins D, Felgenhauer J, et al: RT-PCR evaluation of peripheral blood, bone marrow and peripheral blood stem cells in children and adolescents undergoing VACIME chemotherapy for Ewing's sarcoma and alveolar rhabdomyosarcoma. Bone Marrow Transplant 24:527-33, 1999
77. Athale U H, Shurtleff S A, Jenkins J J, et al: Use of Reverse Transcriptase Polymerase Chain Reaction for Diagnosis and Staging of Alveolar Rhabdomyosarcoma, Ewing Sarcoma Family of Tumors, and Desmoplastic Small Round Cell Tumor. Am J Pediatr Hematol Oncol 23:99-104, 2001
78. Mackall C, Berzofsky J, Heiman L J: Targeting tumor specific translocations in sarcomas in pediatric patients for immunotherapy. Clin Orthop:25-31, 2000
79. Modak S, Kramer K, Humayun G, et al: Monoclonal antibody 8H9 targets a novel cell surface antigen expressed by a wide spectrum of human solid tumors. Cancer Research 61:4048-4054, 2001
80. Guo H F, Rivlin K, Dubel S, et al: Recombinant anti-ganglioside GD2 scFv-streptavidin fusion protein for tumor pretargeting. Proceedings of the American Association for Cancer Research 37:469, 1996
81. Cheung N K, Canete A, Cheung I Y, et al: Disialoganglioside GD2 anti-idiotypic monoclonal antibodies. International Journal of Cancer 54:499-505, 1993
82. Thanavala Y M, Brown S E, Howard C R, et al: A surrogate hepatitis B virus antigenic epitope represented by a synthetic peptide and an internal image antiidiotype antibody. Journal of Experimental Medicine 164:227-236, 1986
83. Wagner U, Schlebusch H, Kohler S, et al: Immunological responses to the tumor-associated antigen CA125 in patients with advanced ovarian cancer induced by the murine monoclonal anti-idiotype vaccine ACA125. Hybridoma 16:33-40, 1997
84. Reinhold U, Liu L, Ludtke-Handjery H-C, et al: Specific lysis of melanoma cells by receptor grafted T cells is enhanced by anti-idiotypic monoclonal antibodies directed to scFv domain of the receptor. Journal of Investigative Dermatology 112:744-750, 1999
85. Koehne G, Gallardo H F, Sadelain M, et al: Rapid selection of antigen-specific T lymphocytes by retroviral transduction. Blood 96:109-117, 2000
86. Mizoguchi H, O'Shea J J, Longo D L, et al: Alterations in signal transduction molecules in T lymphocytes from tumor-bearing mice. Science 258:1795-1798, 1992
87. Gong J H, Maki G, Klingemann H G: Characterization of a human cell line (NK-92) with phenotypical and functional characteristics of activated natural killer cells. Leukemia 8:652-8, 1994
88. Tonn T, Becker S, Esser R, et al: Cellular immunotherapy of malignancies using the clonal natural killer cell line NK-92. J Hematother Stem Cell Res 10:535-44, 2001
89. Maki G, Klingemann H G, Martinson J A, et al: Factors regulating the cytotoxic activity of the human natural killer cell line, NK-92. J Hematother Stem Cell Res 10:369-83, 2001
90. Nagashima S, Mailliard R, Kashii Y, et al: Stable transduction of the interleukin-2 gene into human natural killer cell lines and their phenotypic and functional characterization in vitro and in vivo. Blood 91:3850-61, 1998
91. Maki G: Ex vivo purging of stem cell autografts using cytotoxic cells. J Hematother Stem Cell Res 10:545-51, 2001
92. Goddu S, Howell R, Bouchet L, et al: MIRD Cellular S Factors. Self-absorbed dose per unit cumulated activity for selected radionuclides and monoenergetic electrons and alpha particle emitters incorporated into different cell compartments. Reston, Va. Soc Nucl Med:183, 1997
93. Ugur O, Kothari P J, Finn R D, et al: Ga-66 labeled somatostatin analogue DOTA-DPhe1-Tyr3-octreotide as a potential agent for positron emission tomography imaging and receptor mediated internal radiotherapy of somatostatin receptor positive tumors. Nucl Med Biol 29:147-57, 2002
94. Rogers B E, Zinn K R, Buchsbaum D J: Gene transfer strategies for improving radiolabeled peptide imaging and therapy. Q J Nucl Med 44:208-23, 2000
95. Zinn K R, Chaudhuri T R, Buchsbaum D J, et al: Simultaneous evaluation of dual gene transfer to adherent cells by gamma-ray imaging. Nucl Med Biol 28:135-44, 2001
96. Zinn K R, Chaudhuri T R, Krasnykh V N, et al: Gamma camera dual imaging with a somatostatin receptor and thymidine kinase after gene transfer with a bicistronic adenovirus in mice. Radiology 223:417-25, 2002
97. Gambhir S S, Herschman H R, Chemy S R, et al: Imaging transgene expression with radionuclide imaging technologies. Neoplasia 2:118-38, 2000
98. Yu Y, Annala A J, Barrio J R, et al: Quantification of target gene expression by imaging reporter gene expression in living animals. Nat Med 6:933-7, 2000
99. Tjuvajev J G, Stockhammer G, Desai R, et al: Imaging the expression of transfected genes in vivo. Cancer Res 55:6126-6132, 1995
100. Alauddin M M, Conti P S, Mazza S M, et al: 9-[(3-[18F]-fluoro-1-hydroxy-2-propoxy)methyl]guanine ([18F]-FHPG): a potential imaging agent of viral infection and gene therapy using PET. Nucl Med Biol 23:787-92, 1996
101. Tjuvajev J G, Finn R, Watanabe K, et al: Noninvasive imaging of herpes virus thymidine kinase gene transfer and expression: a potential method for monitoring clinical gene therapy. Cancer Res 56:4087-4095, 1996
102. Gambhir S S, Barrio J R, Wu L, et al: Imaging of adenoviral-directed herpes simplex virus type 1 thymidine kinase reporter gene expression in mice with radiolabeled ganciclovir. J Nucl Med 39:2003-11, 1998
103. Gambhir S S, Barrio J R, Phelps M E, et al: Imaging adenoviral-directed reporter gene expression in living animals with positron emission tomography. Proc Natl Acad Sci USA 96:2333-8, 1999
104. Garin M I, Garrett E, Tiberghien P, et al: Molecular mechanism for ganciclovir resistance in human T lymphocytes transduced with retroviral vectors carrying the herpes simplex virus thymidine kinase gene. Blood 97:122-9, 2001
105. Virgolini I, Leimer M, Handmaker H, et al: Somatostatin receptor subtype specificity and in vivo binding of a novel tumor tracer, 99 mTc-P829. Cancer Res 58:1850-9, 1998

106. Kluxen F W, Bruns C, Lubbert H: Expression cloning of a rat brain somatostatin receptor cDNA. Proc Natl Acad Sci USA 89:4618-22, 1992
107. Bell G I, Reisine T: Molecular biology of somatostatin receptors. Trends Neurosci 16:34-8, 1993
108. Panetta R, Greenwood M T, Warszynska A, et al: Molecular cloning, functional characterization, and chromosomal localization of a human somatostatin receptor (somatostatin receptor type 5) with preferential affinity for somatostatin-28. Mol Pharmacol 45:417-27, 1994
109. O'Carroll A M, Lolait S J, Konig M, et al: Molecular cloning and expression of a pituitary somatostatin receptor with preferential affinity for somatostatin-28. Mol Pharmacol 42:939-46, 1992
110. Yamada Y, Reisine T, Law S F, et al: Somatostatin receptors, an expanding gene family: cloning and functional characterization of human SSTR3, a protein coupled to adenylyl cyclase. Mol Endocrinol 6:2136-42, 1992
111. Tsutsumi A, Takano H, Ichikawa K, et al: Expression of somatostatin receptor subtype 2 mRNA in human lymphoid cells. Cell Immunol 181:44-9, 1997
112. Elliott D E, Li J, Blum A M, et al: SSTR2A is the dominant somatostatin receptor subtype expressed by inflammatory cells, is widely expressed and directly regulates T cell IFN-gamma release. Eur J Immunol 29:2454-63, 1999
113. Talme T, Ivanoff J, Hagglund M, et al: Somatostatin receptor (SSTR) expression and function in normal and leukaemic T-cells. Evidence for selective effects on adhesion to extracellular matrix components via SSTR2 and/or 3. Clin Exp Immunol 125:71-9, 2001
114. Aparici C M, Narula J, Puig M, et al: Somatostatin receptor scintigraphy predicts impending cardiac allograft rejection before endomyocardial biopsy. Eur J Nucl Med 27:1754-9, 2000
115. van Hagen P M, Krenning E P, Kwekkeboom D J, et al: Somatostatin and the immune and haematopoetic system; a review. Eur J Clin Invest 24:91-9, 1994
116. Atiya A, Malik M, Une S, et al: Immunomodulatory activities of the somatostatin receptor subtype analogues on human peripheral blood lymphocytes. Transplant Proc 29:2151, 1997
117. Smanik P A, Liu Q, Furminger T L, et al: Cloning of the human sodium iodide symporter. Biochem Biophys Res Comm 226:339-345, 1996
118. Dai G, Levy O, Carrasco N: Cloning and characterization of the thyroid iodide transporter. Nature 379:458-460, 1996
119. Smanik P A, Ryu K Y, Theil K S, et al: Expression, exon-intron organization, and chromosome mapping of the human sodium iodine symporter. J Endocrinol 138:3555-3558, 1997
120. Kogai T, Schultz J J, Johnson L S, et al: Retinoic acid induces sodium/iodide symporter gene expression and radioiodide uptake in the MCF-7 breast cancer cell line. PNAS (USA) 97:8519-8524, 2000
121. Spitzweg C, Zhang S, Bergert E R, et al: Prostate-specific antigen (PSA) promoter-driven androgen-inducible expression of sodium iodide symporter in prostate cancer cell lines. Cancer Res 59:2136-2141, 1999
122. Spitzweg C, O'Connor M K, Bergert E R, et al: Treatment of prostate cancer by radioiodine therapy after tissue-specific expression of the sodium iodide symporter. Cancer Res 60:6526-6530, 2000
123. Boland A, Ricard M, Opolon P, et al: Adenovirus-mediated transfer of the thyroid sodium/iodine symporter gene into tumors for a targeted radiotherapy. Cancer Res 60:3484-3492, 2000
124. Mandell R B, Mandell L Z, Link Jr C R: Radioisotope concentrator gene therapy using the sodium/iodide symporter gene. Cancer Res 59:661-668, 1999
125. Cho J-Y, Xing S, Liu X, et al: Expression and activity of human Na+/I-symporter in human glioma cells by adenovirus-mediated gene delivery. Gene Therapy 7:740-749, 2000
126. Scott D A, Wang R, Kreman T M, et al: The prendred syndrome gene encodes a chloride-iodide transport protein. Nat Genet. 21:440-443, 1999
127. Royaux I E, Suzuki K, Mori A, et al: Pendrin, the protein encoded by the Pendred syndrome gene (PDS), is an apical porter of iodide in the thyroid and is regulated by thyroglobin in FRTL-5 cells. J Endocrinol 141:839-845, 2000
128. Reubi J C, Waser B, Schaer J C, et al: Somatostatin receptor sst1-sst5 expression in normal and neoplastic human tissues using receptor autoradiography with subtype-selective ligands. Eur J Nucl Med 28:836-46, 2001
129. Orlando C, Raggi C C, Bagnoni L, et al: Somatostatin receptor type 2 gene expression in neuroblastoma, measured by competitive RT-PCR, is related to patient survival and to somatostatin receptor imaging by indium-111-pentetreotide. Med Pediatr Oncol 36:224-6, 2001
130. Carrasco N: Iodide transport in the thyroid gland. Biochim Biophys Acta 1154:65-82, 1993
131. Koller K J, Whitehorn E A, Tate E, et al: A generic method for the production of cell lines expressing high levels of 7-transmembrane receptors. Anal Biochem 250:51-60, 1997
132. Kundra V, Mannting F, Jones A G, et al: Noninvasive monitoring of somatostatin receptor type 2 chimeric gene transfer. J Nucl Med 43:406-12, 2002
133. Rogers B E, McLean S F, Kirkman R L, et al: In vivo localization of [(111)In]-DTPA-D-Phe1-octreotide to human ovarian tumor xenografts induced to express the somatostatin receptor subtype 2 using an adenoviral vector. Clin Cancer Res 5:383-93, 1999
134. Kwa H B, Wesseling J, Verhoeven A H, et al: Immunoscintigraphy of small-cell lung cancer xenografts with anti neural cell adhesion molecule monoclonal antibody, 123C3: improvement of tumour uptake by internalisation. Br J Cancer 73:439-46, 1996
135. Matzku S, Brocker E B, Bruggen J, et al: Modes of binding and internalization of monoclonal antibodies to human melanoma cell lines. Cancer Res 46:3848-54, 1986
136. Williams D A: Retroviral-fibronectin interactions in transduction of mammalian cells. Ann NY Acad Sci 872:109-114, 1999
137. Pollok K E, Hanenberg H, Noblitt T W, et al: High-efficiency gene transfer into narmal and adenosine deaminase-deficient T lymphocytes is mediated by transduction on recombinant fibronectin fragments. J Virol 72:4882-4892, 1998
138. Fehse B, Schade U M, Li Z, et al: Highly-efficient gene transfer with retroviral vectors into human T lymphocytes on fibronectin. British Journal of Haematology 102:566-574, 1998
139. Cheung I Y, Cheung N K V: Quantitation of marrow disease in neuroblastoma by real-time reverse transcription-PCR. Clin Cancer Res 7:1698-1705, 2001

140. Mora J, Cheung N K V, Juan G, et al: Neuroblastic and schwannian stromal cells of neuroblastoma are derived from a tumoral progenitor cell. Supported in part by ASCO YIA 2000, 2000
141. Koehne G, Zanzonico P, Gallardo H F, et al: Noninvasive imaging of human radiolabeled antigen-specific donor T lymphocytes after adoptive immunotherapy in SCID-mice. Blood 96, 2000
142. Yee C, Riddell S R, Greenberg P D: In vivo tracking of tumor-specific T cells. Curr Opin Immunol 13:141-146, 2001
143. Xiaoning R T, Ogg G S, Hansasuta P, et al: Rapid death of adoptively transferred T cells in acquired immunodeficiency syndrome. Blood 93:1506-1510, 1999
144. Riddell S R, Elliott M, Lewinsohn D A, et al: T-cell mediated rejection of gene-modified HIV-specific cytotoxic T lymphocytes in HIV-infected patients. Nat Med 2:216-223, 1996
145. Campbell J J, Butcher E C: Chemokines in tissue-specific and microenviornment-specific lympocyte homing. Current Opinion in Imnunology 12:336-341, 2000
146. Nishimura T, Iwakabe K, Sekimoto M, et al: Distinct role of antigen-specific T helper type I (Th1) and Th2 cells in tumor eradication in vivo. J. Exp. Med. 190:617-627, 1999
147. Cascieri M A, Springer M S: The chemokine/chemokine-receptor family: potential and progress for therapeutic intervention. Current Opinion in Chem Bio 4:420-427, 2000
148. Uekusa Y, Yu W G, Mukai T, et al: A pivotal role for CC chemokine receptor 5 in T-cell migration to tumor sites induced by interleukin 12 treatment in tumor-bearing mice. Cancer Res 62:3751-8, 2002
149. Agostini C, Facco M, Siviero M, et al: CXC chemokines IP-10 and mig expression and direct migration of pulmonary CD8+/CXCR3+ T cells in the lungs of patients with HIV infection and T cell alveolitis. Am J Respir Crit. Care Med 162:1466-1473, 2000
150. Kim J J, Nottingham L K, Sin J I, et al: CD8 positive T cells influence antigen-specific immune responses through the expression of chemokines. J Clin Invest 102:1112-1124, 1998
151. Price D A, Klenerman P, Booth B L, et al: Cytotoxic T lymphocytes, chemokines and antiviral immunity. Immunology Today 20:212-216, 1999
152. Rossig C, Bollard C M, Nuchtern J G, et al: Epstein-Barr virus-specific human T lymphocytes expressing antitumor chimeric T-cell receptors: potential for improved immunotherapy. Blood 99:2009-16, 2002
153. Yu C, Seidel K, Nash R A, et al: Synergism between mycophenolate mofetil and cyclosporine in preventing graft-versus-host disease among lethally irradiated dogs given DLA-nonidentical unrelated marrow grafts. Blood 91:2581-7, 1998
154. Cheung N K, Guo H F, Modak S, Cheung I Y. Anti-idiotypic antibody facilitates scFv chimeric immune receptor gene transduction and clonal expansion of human lymphocytes for tumor therapy. 2002 (submitted)
155. Cheung N K, Guo H F, Modak S, Cheung I Y. Anti-idiotypic antibody as the surrogate antigen for cloning scFv and its fusion proteins. 2002 (submitted)
156. Cheung N K V, Guo H F, Modak S, Larson S M. Single chain Fv-streptavidin substantially improved therapeutic index in multi-step targeting directed at disialoganglioside GD2. 2002 (in preparation)

What is claimed is:

1. A method for inducing proliferation in a population of lymphocytes, comprising the steps of:
   (a) introducing an expressable gene sequence encoding a chimeric single chain antibody (scFv) coupled to a transmembrane domain and a signaling domain into a lymphocyte, wherein the scFv comprises the heavy and light chain variable regions of monoclonal antibody 8H9, and the transmembrane domain is derived from the transmembrane domain of CD28; and
   (b) exposing the lymphocyte to an anti-idiotypic antibody that will bind to the chimeric scfv expressed on the surface of the lymphocyte, thereby inducing proliferation of the lymphocyte.

2. The method of claim 1, wherein the lymphocyte is a peripheral blood lymphocyte.

3. The method of claim 1, wherein the lymphocyte is a T cell or NK cell.

4. The method of claim 3, wherein the T cell is a CD4$^+$ T cell or CD8$^+$ T cell.

5. The method of claim 1, wherein the lymphocyte is obtained from a cancer patient.

6. The method of claim 1, wherein the signaling domain is derived from the signaling domain of TCR-ζ chain.

7. The method of claim 1, wherein the anti-idiotypic antibody is used ex vivo to activate a lymphocyte.

* * * * *